(12) United States Patent
Gassman et al.

(10) Patent No.: US 11,393,565 B2
(45) Date of Patent: Jul. 19, 2022

(54) MEDICAL FLUID DELIVERY SYSTEM INCLUDING A MOBILE PLATFORM FOR PATIENT ENGAGEMENT AND TREATMENT COMPLIANCE

(71) Applicants: BAXTER INTERNATIONAL INC., Deerfield, IL (US); BAXTER HEALTHCARE SA, Glattpark (CH)

(72) Inventors: Christopher Daniel Gassman, Deerfield, IL (US); Derek Wiebenson, Deerfield, IL (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 0 days.

(21) Appl. No.: 17/215,979

(22) Filed: Mar. 29, 2021

(65) Prior Publication Data
US 2021/0217502 A1 Jul. 15, 2021

Related U.S. Application Data

(60) Division of application No. 16/561,273, filed on Sep. 5, 2019, now Pat. No. 10,964,417, which is a
(Continued)

(51) Int. Cl.
*G16H 10/60* (2018.01)
*G16H 20/17* (2018.01)
(Continued)

(52) U.S. Cl.
CPC ....... *G16H 10/60* (2018.01); *G06K 19/06028* (2013.01); *G06K 19/06037* (2013.01); *G16H 20/17* (2018.01); *G16H 80/00* (2018.01)

(58) Field of Classification Search
CPC ......... G16H 10/40; G16H 10/60; G16H 80/00
See application file for complete search history.

(56) References Cited

U.S. PATENT DOCUMENTS

| 4,464,172 A | 8/1984 | Lichtenstein |
| 5,151,082 A | 9/1992 | Gorsuch et al. |
(Continued)

FOREIGN PATENT DOCUMENTS

| CN | 1950125 | 4/2007 |
| CN | 1960775 | 5/2007 |
(Continued)

OTHER PUBLICATIONS

Manns et al., The acu-menTM: A new device for continuous renal replacement therapy in actue renal failure, Kidney International, 1998, pp. 268-274, vol. 54.
(Continued)

*Primary Examiner* — Kevin Kim
(74) *Attorney, Agent, or Firm* — K&L Gates LLP

(57) ABSTRACT

A patient platform for patient engagement and treatment compliance is disclosed. In an example, a home therapy machine of a patient is configured to transmit treatment information and a clinician database is configured to store a medical record and a registration file identifying the home therapy machine and a personal device of the patient as registered devices. The registration file also identifies whether the personal device installed an application for viewing the treatment information. A server is configured to store the treatment information to the medical record, receive an indication that the treatment information is to be displayed at the personal device, and determine from the registration file if the application is installed on the personal device. If the application is not installed, the server converts
(Continued)

the treatment information to text message or Short Messaging Service ("SMS") format for transmission.

20 Claims, 28 Drawing Sheets

Related U.S. Application Data continuation-in-part of application No. 15/386,913, filed on Dec. 21, 2016, now Pat. No. 10,589,014.

(60) Provisional application No. 62/727,305, filed on Sep. 5, 2018.

(51) Int. Cl.
*G16H 80/00* (2018.01)
*G06K 19/06* (2006.01)

(56) References Cited

U.S. PATENT DOCUMENTS

| | | | |
|---|---|---|---|
| 5,247,434 | A | 9/1993 | Peterson et al. |
| 5,486,286 | A | 1/1996 | Peterson et al. |
| 5,732,401 | A | 3/1998 | Conway |
| 5,764,923 | A | 6/1998 | Tailman et al. |
| 5,788,851 | A | 8/1998 | Kenley et al. |
| 5,867,821 | A | 2/1999 | Ballantyne et al. |
| 5,919,154 | A | 7/1999 | Toavs et al. |
| 5,933,136 | A | 8/1999 | Brown |
| 6,230,142 | B1 | 5/2001 | Benigno et al. |
| 6,471,382 | B2 | 10/2002 | Eichhorn |
| 6,685,831 | B2 | 2/2004 | Rainer |
| 7,044,927 | B2 | 5/2006 | Mueller et al. |
| 7,072,769 | B2 | 7/2006 | Fletcher-Haynes et al. |
| 7,185,282 | B1 | 2/2007 | Naidoo et al. |
| 7,801,598 | B2 | 9/2010 | Zhu et al. |
| 7,801,746 | B2 | 9/2010 | Moll et al. |
| 7,890,341 | B2 | 2/2011 | McNally et al. |
| 8,062,513 | B2 | 11/2011 | Yu et al. |
| 8,095,390 | B2 | 1/2012 | Bluemler et al. |
| 8,178,040 | B2 | 5/2012 | Brauer |
| 8,257,582 | B2 | 9/2012 | Yu et al. |
| 8,267,308 | B2 | 9/2012 | Devergne et al. |
| 8,315,654 | B2 | 11/2012 | Balschat et al. |
| 8,321,044 | B2 | 11/2012 | Plahey et al. |
| 8,543,420 | B2 | 9/2013 | Darby et al. |
| 8,632,485 | B2 | 1/2014 | Schlaeper et al. |
| 8,676,660 | B2 | 3/2014 | Yu et al. |
| 8,679,075 | B2 | 3/2014 | Lurvey |
| 8,698,741 | B1 | 4/2014 | Wang et al. |
| 8,769,625 | B2 | 7/2014 | Wang |
| 8,823,500 | B2 | 9/2014 | Heath |
| 8,836,519 | B2 | 9/2014 | Wright et al. |
| 8,906,240 | B2 | 12/2014 | Crnkovich et al. |
| 8,926,550 | B2 | 1/2015 | Plahey et al. |
| 9,081,382 | B2 | 7/2015 | Doyle et al. |
| 9,178,891 | B2 | 11/2015 | Wang et al. |
| 9,250,216 | B2 | 2/2016 | Wright et al. |
| 9,333,286 | B2 | 5/2016 | Wright et al. |
| 9,408,958 | B2 | 8/2016 | Wang et al. |
| 9,517,295 | B2 | 12/2016 | Wilt et al. |
| 9,727,696 | B2 | 8/2017 | Case et al. |
| 10,380,321 | B2 | 8/2019 | Kamen et al. |
| 10,391,221 | B2 | 8/2019 | Raiford et al. |
| 2002/0040282 | A1 | 4/2002 | Bailey |
| 2002/0082728 | A1 | 6/2002 | Mueller |
| 2002/0087361 | A1 | 7/2002 | Benigno et al. |
| 2002/0103453 | A1 | 8/2002 | Burbank et al. |
| 2002/0147423 | A1 | 10/2002 | Burbank et al. |
| 2003/0220598 | A1 | 11/2003 | Busby |
| 2004/0115132 | A1 | 1/2004 | Brown |
| 2004/0111294 | A1 | 6/2004 | McNally |
| 2004/0172222 | A1 | 9/2004 | Simpson et al. |
| 2005/0021370 | A1 | 1/2005 | Riff et al. |
| 2005/0055242 | A1 | 3/2005 | Bello et al. |
| 2005/0277890 | A1 | 12/2005 | Stewart et al. |
| 2005/0277911 | A1 | 12/2005 | Stewart et al. |
| 2007/0112603 | A1 | 5/2007 | Kauthen et al. |
| 2008/0040151 | A1 | 2/2008 | Moore |
| 2008/0154177 | A1 | 6/2008 | Moubayed et al. |
| 2008/0828900 | | 7/2008 | Plahey et al. |
| 2008/0215627 | A1 | 9/2008 | Higgins et al. |
| 2008/0268413 | A1 | 10/2008 | Leichner |
| 2009/0164248 | A1 | 6/2009 | Hunt |
| 2010/0010428 | A1 | 1/2010 | Yu et al. |
| 2010/0137693 | A1* | 6/2010 | Porras .............. G16H 20/40 705/2 |
| 2011/0004351 | A1 | 1/2011 | Kelly et al. |
| 2011/0087501 | A1 | 4/2011 | Severin |
| 2011/0172744 | A1 | 7/2011 | Davis et al. |
| 2011/0257891 | A1 | 10/2011 | Akonur |
| 2012/0029937 | A1 | 2/2012 | Neftel |
| 2012/0041777 | A1 | 2/2012 | Case et al. |
| 2012/0081225 | A1 | 4/2012 | Waugh |
| 2012/0138533 | A1 | 6/2012 | Curtis |
| 2012/0182939 | A1 | 7/2012 | Rajan et al. |
| 2012/0212455 | A1 | 8/2012 | Kloeffel |
| 2012/0238851 | A1 | 9/2012 | Kamen |
| 2012/0289928 | A1 | 11/2012 | Wright et al. |
| 2013/0018355 | A1 | 1/2013 | Brand et al. |
| 2013/0020237 | A1 | 1/2013 | Wilt et al. |
| 2013/0037485 | A1 | 2/2013 | Wilt et al. |
| 2013/0133036 | A1 | 5/2013 | Wang |
| 2013/0138452 | A1 | 5/2013 | Cork |
| 2013/0191513 | A1 | 7/2013 | Kamen et al. |
| 2013/0310735 | A1 | 7/2013 | Yu et al. |
| 2013/0211206 | A1 | 8/2013 | Sands et al. |
| 2013/0297330 | A1 | 11/2013 | Kamen et al. |
| 2013/0317753 | A1 | 11/2013 | Kamen et al. |
| 2013/0317837 | A1 | 11/2013 | Ballantyne et al. |
| 2014/0012595 | A1 | 1/2014 | Fox et al. |
| 2014/0039447 | A1 | 2/2014 | Wright et al. |
| 2014/0091022 | A1 | 4/2014 | Raiford et al. |
| 2014/0098209 | A1 | 4/2014 | Neff |
| 2014/0188516 | A1 | 7/2014 | Kamen et al. |
| 2014/0222450 | A1 | 8/2014 | Gray et al. |
| 2014/0266983 | A1 | 9/2014 | Christensen |
| 2014/0267003 | A1 | 9/2014 | Wang et al. |
| 2014/0289812 | A1 | 9/2014 | Wang et al. |
| 2014/0298171 | A1 | 10/2014 | Wang et al. |
| 2014/0299544 | A1 | 10/2014 | Wilt et al. |
| 2014/0345386 | A1 | 11/2014 | Wright et al. |
| 2015/0018758 | A1 | 1/2015 | John |
| 2015/0112264 | A1 | 4/2015 | Kamen |
| 2015/0154364 | A1 | 6/2015 | Biasi et al. |
| 2015/0196699 | A9 | 7/2015 | Wilt et al. |
| 2015/0253860 | A1 | 9/2015 | Merics et al. |
| 2016/0021191 | A1 | 1/2016 | Wang et al. |
| 2016/0030655 | A1 | 2/2016 | Wright et al. |
| 2016/0055303 | A1 | 2/2016 | Keller |
| 2016/0058933 | A1 | 3/2016 | Ballantyne et al. |
| 2016/0206800 | A1 | 7/2016 | Tanenbaum et al. |
| 2016/0239637 | A1 | 8/2016 | Miller |
| 2016/0261974 | A1 | 9/2016 | Arrizza |
| 2016/0310653 | A1 | 10/2016 | Wang et al. |
| 2016/0356874 | A1 | 12/2016 | Wang et al. |
| 2017/0000938 | A1 | 1/2017 | Wilt et al. |
| 2017/0011175 | A1 | 1/2017 | Cocks et al. |
| 2017/0220769 | A1 | 8/2017 | Miller et al. |
| 2018/0036469 | A1 | 2/2018 | Crnkovich et al. |
| 2018/0040123 | A1 | 2/2018 | Neff |
| 2018/0063693 | A1* | 3/2018 | Chakraborty ......... H04W 8/005 |
| 2019/0116226 | A1 | 4/2019 | Arrizza |
| 2019/0154744 | A1 | 5/2019 | Mackinder |
| 2019/0160227 | A1 | 5/2019 | Li |

FOREIGN PATENT DOCUMENTS

| | | |
|---|---|---|
| CN | 101606157 | 12/2009 |
| CN | 101611409 | 12/2009 |
| EP | 0611228 | 8/1994 |
| EP | 1195708 | 4/2002 |
| EP | 1 235 614 | 9/2002 |

(56) References Cited

FOREIGN PATENT DOCUMENTS

| EP | 2368588 | 9/2011 |
|---|---|---|
| WO | 9014850 | 12/1990 |
| WO | 94/24929 | 11/1994 |
| WO | 99/46657 | 7/1999 |
| WO | 99/52025 | 10/1999 |
| WO | 2001/37786 | 5/2001 |
| WO | 2002/078783 | 10/2002 |
| WO | 2004/069095 | 8/2004 |
| WO | 2004/070546 | 8/2004 |
| WO | 2004/070548 | 8/2004 |
| WO | 2004/070549 | 8/2004 |
| WO | 2004/070556 | 8/2004 |
| WO | 2004/070557 | 8/2004 |
| WO | 2004/070562 | 8/2004 |
| WO | 2004/070994 | 8/2004 |
| WO | 2004/070995 | 8/2004 |
| WO | 2005/101279 | 10/2005 |
| WO | 2010056712 | 5/2010 |
| WO | 2015183981 | 12/2015 |
| WO | 2016196325 | 12/2016 |

OTHER PUBLICATIONS

Supplementary International Search Report for Application No. PCT/US2013/040967 dated Jun. 19, 2014.
Letter from Mexican associate regarding office action for MX/a/2007/014394 dated Mar. 12, 2013.
European office action for Application No. 11 075 130.2-1651 dated Sep. 23, 2013.
European office action for Application No. 11 075 130.2-1651 dated Oct. 6, 2014.
Patent Examination Report No. 1—Australia, dated Aug. 18, 2015, Patent Application No. 2013263015—7 pages.
Wang, Samuel J. et al. User-Definable Medication Favorites for an Outpatient Electronic Medical Record System. Proc AMIA Symp. 2001 : 1055.
Opposition against EP 2368588 (EP Application 11075130.2) mailed May 13, 2016, 30 pages.
Office Action issued in U.S. Appl. No. 15/088,966, dated Jun. 20, 2016, 17 pages.
Office Action issued in U.S. Appl. No. 15/135,837, dated Aug. 12, 2016, 17 pages.
Office Action issued in U.S. Appl. No. 13/828,900, dated Aug. 8, 2016, 28 pages.
Office Action issued in U.S. Appl. No. 13/828,900, dated Jan. 25, 2016, 28 pages.
Office Action issued in CN Application 201380031530.6 dated Aug. 1, 2016, 12 pages.
Office Action issued in AU Application 2013263015 dated Aug. 16, 2016, 6 pages.
Office Action issued in U.S. Appl. No. 15/135,810, dated Jun. 28, 2016, 18 pages.
4008H Hemodialysis Machine Operation Instructions, Software Version 4.2, Fresenius Medical Care.
Tsavdaris, et al., "Monitoring and Supporting Home Maemodialysis using Telematic Services", Decision Support Systems Laboratory, National Technical University of Athens, Wire Communications Laboratory, University of Patras.
B. Agroyannis, et al. "Telemedicine technology and applications for home hemodialysis", The International Journal of Artificial Organs, vol. 22/No. 10, 1999/ pp. 679-683.
Contents, The International Journal of Artificial Organs, vol. 22/No. 10—1999/pp. 657-722.
Proceedings of the 19th Annual International Conference of the IEEE Engineering in Medicine and Biology Society, Oct. 30—Nov. 2, 1997, Chicago, IL USA.
Notice of opposition to a European patent, Patent No. EP 1 235 614, dated May 8, 2013.
Opposition Statement, Patent No. EP 1 235 614 B, dated May 8, 2013.
Notice of opposition to a European patent, Patent No. EP2368588, dated Jun. 14, 2016.
Reexamination Certificate, U.S. Pat. No. B1 5,211,849, Certificate Issued May 27, 1997.
Decision on Opposition, European Patent No. 1 235 614 dated Jul. 30, 2015.
Non-Final Office Action dated Jun. 20, 2016 in U.S. Appl. No. 15/088,966.
Final Office Action dated Nov. 25, 2016 in U.S. Appl. No. 15/088,966.
Non-Final Office Action dated Jun. 28, 2016 in U.S. Appl. No. 15/135,810.
Final Office Action dated Jan. 4, 2017 in U.S. Appl. No. 15/135,810.
Non-Final Office Action dated Aug. 12, 2016 in U.S. Appl. No. 15/135,837.
Final Office Action dated Feb. 3, 2017 in U.S. Appl. No. 15/135,837.
Mexican Office Action dated Dec. 14, 2016 in corresponding Mexican Application No. MX/a/2014/013920.
Chinese Office Action dated Feb. 21, 2017 in corresponding Chinese Application No. 201380031530.6.
New Zealand Office Action dated Mar. 10, 2017 in corresponding New Zealand Application No. 702249.
Canadian Office Action dated Feb. 24, 2017 in corresponding Canadian Application No. 2,873,621—4 pages.
Letter from Mexican associate regarding office action for MX/a/2007/014394 dated Mar. 12, 2012.
Agroyannis et al., "Telemedcine technology and application for home hemodialysis", Contents, The International Journal of Artificial Organs, vol. 22/No. 10—1999/pp. 657-722.
Reexamination Certificate, U.S. Pat. No. B1 5,211,849, Certificate dated May 27, 1997.
International Search Report—PCT/US2017/067662 dated Jun. 13, 2018—9 pages.
Written Opinion of the International Searching Authority—PCT/US2017/067662 dated Jun. 13, 2018—18 pages.
URL:https://hsc.com/Blog/Android-Labs-Bluetooth-HID-device-implementation-your-phone-as-a-mouse-voice-control—Jan. 28, 2015—XP055588550—6 pages.
URL:https://en.wikipedia.org/w/index.php?title=USB_human_interface_device_class&oldid=81482617—Dec. 11, 2017—XP055588361—5pages.
URL:https://web.archive.org/web/20150508052012/https://hsc.com/Blog/Android-Labs-Bluetooth-HID-device-implementation-your-phone-as-a-mouse-voice-control—4 pages.

* cited by examiner

| Patient # | Device Type | Device ID. | Machine ID | Treatment/Medical Information |
|---|---|---|---|---|
| DCM31913 | Apple® S9 | 312.xxx.xxxx | HC09123 | March 12 Treatment Data |
| | | | | March 12 Medical Information |
| | | | | March 13 Treatment Data |
| | | | | March 13 Medical Information |
| GAM41215 | Lite | 847.xxx.xxxx | CL12378 | April 20 Treatment Data |
| | | | | April 22 Treatment Data |
| | | | | April 22 Medical Information |

FIG. 13

MEDICAL FLUID DELIVERY SYSTEM INCLUDING A MOBILE PLATFORM FOR PATIENT ENGAGEMENT AND TREATMENT COMPLIANCE

PRIORITY CLAIM

This application claims priority to and the benefit as a divisional application of U.S. patent application Ser. No. 16/561,273, filed Sep. 5, 2019, now U.S. Pat. No. 10,964,417, which is a non-provisional application of U.S. Provisional Patent Application No. 62/727,305, filed Sep. 5, 2018, the entire contents of which are hereby incorporated by reference and relied upon. U.S. patent application Ser. No. 16/561,273 also claims priority to and the benefit as a continuation-in-part application of U.S. patent application Ser. No. 15/386,913, filed Dec. 21, 2016, now U.S. Pat. No. 10,589,014, the entire contents of which are hereby incorporated by reference and relied upon.

BACKGROUND

Engaging a patient outside of a medical environment for an extended period is currently a virtually impossible task. Similar to beginning a gym membership or buying a treadmill, many patients typically begin strong. For example, at first patients are readily engaged with a medical treatment (e.g., a medical fluid delivery treatment) that is self-administered in the patients' homes. For treatment, patients have to connect themselves to a medical fluid delivery machine (or containers that contain a renal failure treatment fluid) to cleanse their blood from a build-up of toxins. Part of the treatment may include tasks that the patients have to perform such as weighing themselves, taking their blood pressure, and/or recording information related to their treatment. The information recorded by patients is oftentimes reviewed by clinicians to ensure the treatment is progressing as prescribed. Clinicians also review the recorded data to determine whether an adjustment to the treatment is needed.

Overtime, many patients become less enthusiastic with the treatments as they lose their novelty and become just another obligation. As one can imagine, patients would rather engage in more exciting, relaxing, or stimulating activities compared to a self-administered medical treatment. While patients continue the treatments, they sometimes begin to omit performing the additional tasks that go along with the treatments. Omitting the additional tasks and becoming less enthused with treatments has the potential to create gaps in clinical oversight for the ongoing treatment. As patients become further disengaged from the treatments, they may begin to skip treatments or forgo them altogether, risking their health in the process.

SUMMARY

A medical fluid data transfer system including a mobile platform is disclosed herein. The medical fluid data transfer system is configured to improve engagement and/or treatment compliance with a patient through interactions provided through a patient's portable device (e.g., a cellular phone, smartphone, tablet computer, etc.). Specifically, the medical fluid data transfer system provides a patient increased feedback and control (without feeling overwhelmed), which causes the patient to feel as though they are in control of their own treatment rather than following instructions from a clinician. For example, a personal mobile communication device of the medical fluid data transfer system may display treatment information and/or a patient's vital sign data. The personal mobile communication device may also enable a patient to switch between different prescribed treatments or programs without having to directly program a medical fluid delivery machine. Patients that feel in control are more likely to stay engaged with their treatment.

The example medical fluid data transfer system also reduces data gathering burdens on the patient by automating the process. For example, a personal mobile communication device enables a patient to capture treatment data or vital sign data for automatic transmission to a centralized clinician database. Patients may enter data directly into a personal mobile communication device, receive the data electronically from a connected machine, or record the data using a camera. The data is transmitted within the medical fluid data transfer system to a database that stores the data in a patient medical record.

Additionally, the example medical fluid data transfer system provides a gateway to clinicians to enable a patient to communicate with a clinician in real-time regarding any concerns or questions about a medical fluid delivery treatment. In some embodiments, the medical fluid data transfer system also provides patient access to educational or training material. As such, the example medical fluid data transfer system is configured to connect a patient to needed or requested assistance for staying engaged and/or compliant with a treatment.

The medical fluid data transfer system and methodology of the present disclosure is applicable, for example, to fluid delivery for: plasmapheresis, hemodialysis ("HD"), hemofiltration ("HF") hemodiafiltration ("HDF"), and continuous renal replacement therapy ("CRRT") treatments. The medical fluid data transfer system described herein is also applicable to peritoneal dialysis ("PD"), intravenous drug delivery, and nutritional fluid delivery. These modalities may be referred to herein collectively or generally individually as medical fluid delivery or treatment.

The above modalities may be provided by a medical fluid delivery machine that houses components needed to deliver medical fluid, such as one or more pumps, valves, heaters if needed, online medical fluid generation equipment if needed, sensors, such as any one, or more, or all of pressure sensors, conductivity sensors, temperature sensors, air detectors, blood leak detectors, and the like, user interfaces, and control units, which may employ one or more processors and memory to control the above-described equipment. The medical fluid delivery machine may also include one or more filters, such as a dialyzer or hemofilter for cleansing blood and/or an ultrafilter for purifying water, dialysis fluid, or other fluid.

The medical fluid delivery machine and the medical fluid data transfer system and methodology described herein may be used with home-based machines. For example, the systems may be used with home HD, HF or HDF machines, which are operated at the patient's convenience. One such home system is described in U.S. Pat. No. 8,029,454 ("the '454 patent"), issued Oct. 4, 2011, entitled "High Convection Home Hemodialysis/Hemofiltration And Sorbent System", filed Nov. 4, 2004, assigned to the assignees of the present application. Other such home systems are described in U.S. Pat. No. 8,393,690 ("the '690 patent"), issued Mar. 12, 2013, entitled "Enclosure for a Portable Hemodialysis System", filed Aug. 27, 2008. The entire contents of each of the above references are incorporated herein by reference and relied upon.

As described in detail below, the medical fluid data transfer system and methodology of the present disclosure may operate within an encompassing platform system that may include many machines comprising many different types of devices, patients, clinicians, doctors, service personnel, electronic medical records ("EMR") databases, a website, a resource planning system handling data generated via the patient and clinician communications, and business intelligence. The medical fluid data transfer system and methodology of the present disclosure operates seamlessly within the overall system and without contravening its rules and protocols.

In light of the disclosure herein and without limiting the disclosure in any way, in a first aspect of the present disclosure, which may be combined with any other aspect listed herein unless specified otherwise, a machine-accessible device having instructions stored thereon that are configured, when executed, to cause a machine to populate patient medical records of a clinical system by operating a camera to record images, operating a display interface, operating a connection interface configured to connect to a clinician database, the clinician database configured to store patient medical records, and operating a processor to obtain medical information. The processor is operated to obtain medical information by displaying, via the display interface, a user interface with fields to be populated with medical information, and after selection of a data field of the user interface, providing graphically via the display interface, a first option to enter medical information from an image and a second option to enter medical information via text entry. If the first option is selected, the processor receives a recorded image from the camera, the recorded image including a medical device or a screen of a medical device, extracts text from the image, enables a selection, via the display interface, of at least a portion of the text from the image, and writes the selected text from the image into the data field of the user interface as the medical information. If the second option is selected, the processor enables text entry of the data field, via the display interface, as the medical information. The processor is also operated to obtain medical information by, after a send instruction is received, transmitting the medical information written to the data field to a patient medical record stored in the clinician database.

In accordance with a second aspect of the present disclosure, which may be used in combination with any other aspect listed herein unless stated otherwise, the machine-accessible device further comprises instructions stored thereon that are configured, when executed, to cause the machine to operate the processor to determine a data template for the extracted text on the image, process the extracted text using the data template to group the extracted text into fields, and enable a selection of at least one of the fields to write the selected text from the image into the data field of the user interface.

In accordance with a third aspect of the present disclosure, which may be used in combination with any other aspect listed herein unless stated otherwise, the data template is configured to specify a context for the extracted text in relation to text positions within the image.

In accordance with a fourth aspect of the present disclosure, which may be used in combination with any other aspect listed herein unless stated otherwise, the machine-accessible device further comprises instructions stored thereon that are configured, when executed, to cause the machine to operate the processor to determine the data template based on at least one of (i) a selection, via the user interface, of a medical device type, (ii) information scanned from an identifier located on the medical device, and (iii) a label within the extracted text, or (iv) a relative placement of the extracted text.

In accordance with a fifth aspect of the present disclosure, which may be used in combination with any other aspect listed herein unless stated otherwise, the identifier located on the medical device includes at least one of a quick-response ("QR") code, a barcode, a serial number, or a hardware number located on a housing of the medical device or the screen of the medical device.

In accordance with a sixth aspect of the present disclosure, which may be used in combination with any other aspect listed herein unless stated otherwise, the medical device includes at least a renal failure therapy machine, an infusion pump, an oxygen sensor, a respiratory monitor, a glucose meter, a blood pressure monitor, an ECG monitor, a weight scale, and a heart rate monitor.

In accordance with a seventh aspect of the present disclosure, which may be used in combination with any other aspect listed herein unless stated otherwise, the data field of the user interface is configured to receive at least one of blood pressure measurement data, pulse data, weight data, glucose data, temperature data, renal failure manual exchange data, subjective data, or consumable data regarding a consumable item.

In accordance with an eighth aspect of the present disclosure, which may be used in combination with any other aspect listed herein unless stated otherwise, the consumable item includes at least one of a filter, a blood line set, a dialysate concentrate container, a blood anticoagulant container, a medication container, a disposable cassette, a sorbent cartridge, and a water purification container.

In accordance with a ninth aspect of the present disclosure, which may be used in combination with any other aspect listed herein unless stated otherwise, the machine is a personal mobile communication apparatus.

In accordance with a tenth aspect of the present disclosure, which may be used in combination with any other aspect listed herein unless stated otherwise, a method for populating a patient medical record of a clinical database using recorded images includes transmitting to a personal device, a first message prompting a patient to use a camera of the personal device to record a first image of a medical device, and receiving, from the personal device, the first image. The method also includes determining from the first image, via a processor, first medical information indicative of a type or model of the medical device, determining, via the processor, a data template and a second message associated with the determined type or the model of the medical device, and transmitting, via the processor, the second message to the personal device prompting the patient to use the camera to record a second image of a screen of the medical device. The method further includes receiving, via the processor from the personal device, the second image, extracting, via the processor, text from the second image, and processing, via the processor, the extracted text using the data template to group the extracted text into fields. The method moreover includes writing, via the processor, at least some of the text from at least one of the fields to the patient medical record.

In accordance with an eleventh aspect of the present disclosure, which may be used in combination with any other aspect listed herein unless stated otherwise, the method further includes determining, via the processor, a correspondence between one of the fields to a record field in the patient medical record, and writing, via the processor, the at least some of the text from the field to the record field in the patient medical record.

In accordance with a twelfth aspect of the present disclosure, which may be used in combination with any other aspect listed herein unless stated otherwise, the method further includes determining, via the processor, a treatment time from the patient medical record, and transmitting, via the processor, the first message before the treatment time.

In accordance with a thirteenth aspect of the present disclosure, which may be used in combination with any other aspect listed herein unless stated otherwise, the method further includes receiving, in the processor from the personal device, a treatment message indicative that a patient is to begin a treatment, and transmitting, via the processor, the first message before the treatment is to begin.

In accordance with a fourteenth aspect of the present disclosure, which may be used in combination with any other aspect listed herein unless stated otherwise, the first image is received in the processor via a first text message or first Short Messaging Service ("SMS") message and the second image is received in the processor via a second text message or second SMS message.

In accordance with a fifteenth aspect of the present disclosure, which may be used in combination with any other aspect listed herein unless stated otherwise, the method further includes converting, via the processor, the at least some of the text from at least one of the fields to a Health-Level-7 ("HL7") format before writing to the patient medical record.

In accordance with a sixteenth aspect of the present disclosure, which may be used in combination with any other aspect listed herein unless stated otherwise, the method further includes comparing, via the processor, the at least some of the text from at least one of the fields to a predetermined range, and writing, via the processor, the at least some of the text from at least one of the fields if the at least some of the text from at least one of the fields is within the predetermined range.

In accordance with a seventeenth aspect of the present disclosure, which may be used in combination with any other aspect listed herein unless stated otherwise, a system for transmitting information to a patient includes a home therapy machine of the patient configured to transmit treatment information, and a clinician database configured to store the medical record and a registration file identifying the home therapy machine and a personal device of the patient as registered devices and identifying whether the personal device installed an application for viewing the treatment information and the medical information. The system also includes a clinician server communicatively coupled to the clinician database, the home therapy machine, and the personal device. The clinician server is configured to store the treatment information and the medical information to the medical record, receive an indication that at least some of the treatment information and the medical information is to be displayed at the personal device, and determine from the registration file if the application is installed on the personal device. If the application is installed, the clinician server is configured to convert the at least some of the treatment information and the medical information to an application format for display within the application, and transmit the converted at least some of the treatment information and the medical information to the personal device. If the application is not installed, the clinician server is configured to convert the at least some of the treatment information and the medical information to text message or Short Messaging Service ("SMS") format, and transmit the converted at least some of the treatment information and the medical information to the personal device via one or more text message or SMS message.

In accordance with an eighteenth aspect of the present disclosure, which may be used in combination with any other aspect listed herein unless stated otherwise, the application format includes at least one of an Extensible Markup Language ("XML") format or an HyperText Markup Language ("HTML") format.

In accordance with a nineteenth aspect of the present disclosure, which may be used in combination with any other aspect listed herein unless stated otherwise, the indication that at least some of the treatment information and the medical information is to be displayed at the personal device includes at least one of a message from the application or a text/SMS message from the personal device.

In accordance with a twentieth aspect of the present disclosure, which may be used in combination with any other aspect listed herein unless stated otherwise, the registration file is included within the medical record.

In accordance with a twenty-first aspect of the present disclosure, which may be used in combination with any other aspect listed herein unless stated otherwise, the home therapy machine is configured to store a prescription with two programs, each of the programs providing parameters to operate the home therapy machine to perform a treatment, and the clinician server is configured to receive a program message from the personal device indicative of a change to a second program from a first program, and transmit a program instruction to the home therapy machine to change to the second program from the first program.

In a twenty-second aspect of the present disclosure, any of the structure and functionality disclosed in connection with FIGS. 1 to 33 may be combined with any other structure and functionality disclosed in connection with FIGS. 1 to 33.

In light of the present disclosure and the above aspects, it is therefore an advantage of the present disclosure to provide an improved medical fluid delivery system.

It is another advantage of the present disclosure to provide improved patient lifestyle.

It is a further advantage of the present disclosure to provide improved clinician or caregiver efficiency.

It is still another advantage of the present disclosure to provide improved machine efficiency.

It is still a further advantage of the present disclosure to provide improved patient compliance.

It is yet another advantage of the present disclosure to provide a medical fluid data transfer system and methodology that may be applied to different types of medical fluid delivery machines.

It is yet a further advantage of the present disclosure to provide a medical fluid data transfer system and methodology that enables communication between a medical fluid delivery machine and multiple people, such as a patient and clinician or patient and primary caregiver.

Moreover, it is an advantage of the present disclosure to reduce waste of disposable sets and other ancillary soft goods due to discards, which occur often when machine timers expire.

The advantages discussed herein may be found in one, or some, and perhaps not all of the embodiments disclosed herein. Additional features and advantages are described herein, and will be apparent from, the following Detailed Description and the figures.

BRIEF DESCRIPTION OF THE FIGURES

FIG. 13 illustrates an example patient data structure stored on a clinician database of the medical fluid data transfer system of FIG. 10, according to an example embodiment of the present disclosure.

DETAILED DESCRIPTION

Figure 1:
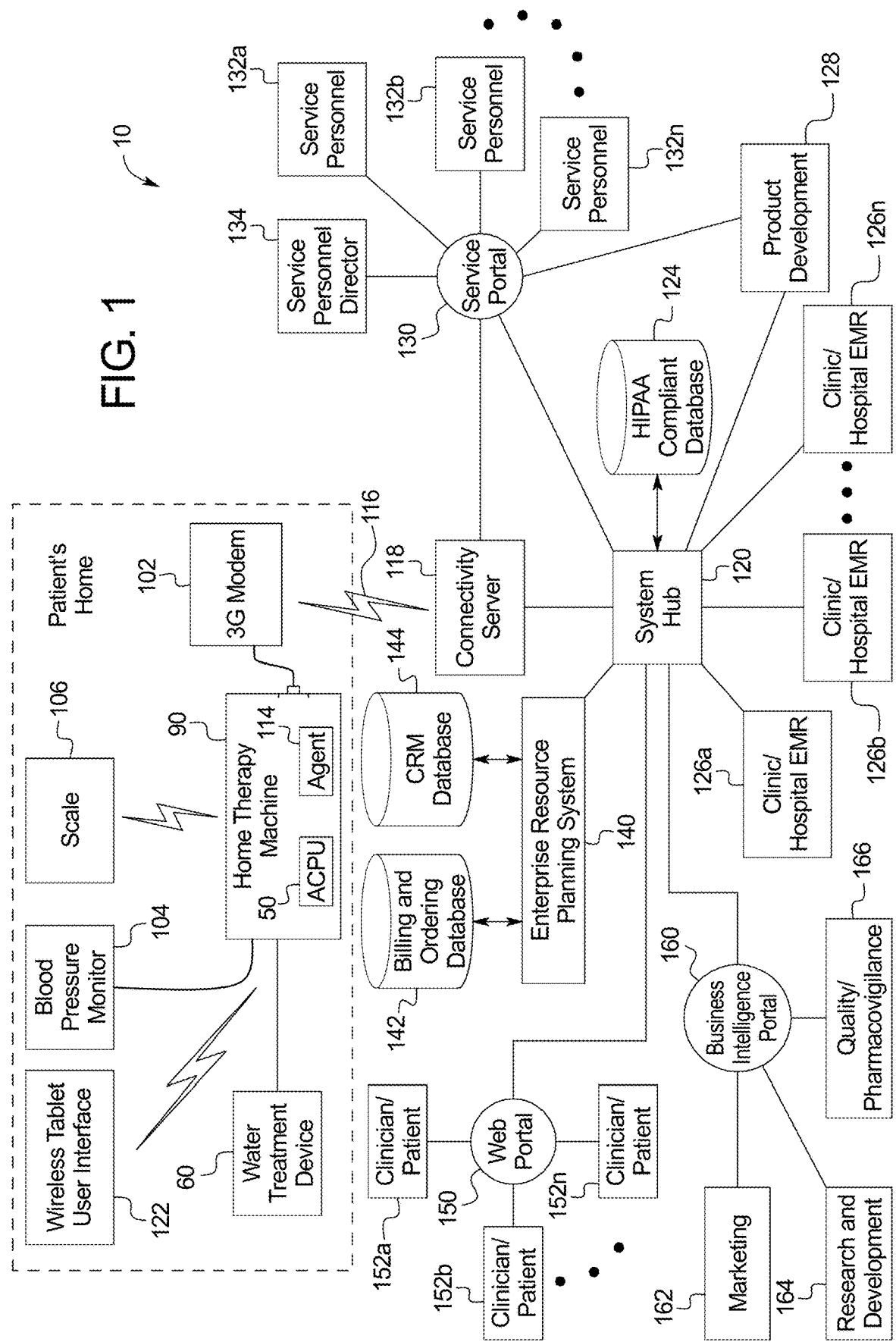
FIG. 1 is a schematic view illustrating one embodiment for a medical fluid data transfer system that incorporates the medical fluid delivery machines of the present disclosure, so that data may be transferred to and from such machines, according to an embodiment of the present disclosure.

A medical fluid delivery system is disclosed herein. The example medical fluid delivery system is configured to improve a patient's engagement with a medical treatment, such as a medical fluid delivery treatment. The medical fluid delivery system is configured to provide a patient more transparency regarding their treatment and at least some control to direct their treatment while providing resources to educate or otherwise assist the patient throughout the treatment process. The example medical fluid delivery system is configured to provide patient engagement regardless of a type or feature sets of medical device(s) related to the treatment or personal mobile communication device(s) of the patient. Such a configuration enables the disclosed medical fluid delivery system to be compatible with virtually any patient situation.

In some embodiments, the medical fluid delivery system includes a personal mobile communication device, a medical fluid delivery machine, and a clinician server/database. The example personal mobile communication device and the medical fluid delivery machine are located at a patient's home and/or located at a self-service medical facility. The clinician server is communicatively coupled to the personal mobile communication device and/or the medical fluid delivery machine via a wide area network (i.e., the Internet). The clinician server is configured as a hub that enables the personal mobile communication device to provide features designed to engage a patient with a medical fluid delivery treatment.

As disclosed herein, the example clinician server receives medical fluid delivery data (e.g., treatment information) from the medical fluid delivery machine, which is stored to one or more patient records in a clinician database. The clinician server provides the personal mobile communication device access to the medical fluid delivery data to enable a patient to track treatment progress. In addition, a patient may use the personal mobile communication device to change a treatment program (or request to change a treatment program). The request is routed through the clinician server to verify the change is appropriate before being transmitted to the medical fluid delivery machine.

The example clinician server operates in connection with the personal mobile communication device to enable a patient to effortlessly provide medical information, such as vital sign data, medical device data, etc. The personal mobile communication device is configured to enable a patient to manually enter data, to record pictures that include data, and/or wirelessly receive data from connected medical devices, such as weight scales, blood pressure monitors, thermometers, glucose meters, etc. The collected data is stored to a patient's medical record. In some embodiments, the clinician server and/or the personal mobile communication device may use templates to determine how received data is to be automatically populated into a patient's medical record.

As disclosed herein, the personal mobile communication device may include a feature-rich smart-device, such as a smartphone or tablet computer. The smart-device may operate a specialized application (e.g., an "app") that is defined by instructions stored in a memory. Execution of the stored instructions causes a process of the smart-device to operate the application, which is configured to increase a patient's engagement with a medical treatment. In some instances, the personal mobile communication device may include a feature-lite traditional cellular phone that contains considerably less processing power and features compared to a smart-device. The cellular device may operate using text messages and/or a specialized application (e.g., an App) that is defined by instructions stored in a memory. The application for the feature-lite device may have fewer features compared with the application for the smart-device.

The disclosure below is separated into two sections. A first section discloses an embodiment of a medical fluid delivery system. A second section discloses features that enable the medical fluid delivery system to increase a patient's engagement and/or compliance with a medical treatment.

I. MEDICAL FLUID DELIVERY SYSTEM EMBODIMENT

The example medical fluid delivery system includes one or more medical fluid delivery machines. One example of a medical fluid delivery machine is a renal failure therapy machine. Regarding renal failure therapy machines, due to various causes, a patient's renal system can fail. Renal failure produces several physiological derangements. It is no longer possible to balance water and minerals or to excrete daily metabolic load. Toxic end products of nitrogen metabolism (urea, creatinine, uric acid, and others) can accumulate in blood and tissue.

Kidney failure and reduced kidney function have been treated with dialysis. Dialysis removes waste, toxins and excess water from the body that normal functioning kidneys would otherwise remove. Dialysis treatment for replacement of kidney functions is critical to many people because the treatment is life saving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment (typically ten to ninety liters of such fluid). The substitution fluid and the fluid accumulated by the patient in between treatments is ultrafiltered over the course of the HF treatment, providing a convective transport mechanism that is particularly beneficial in removing middle and large molecules (in hemodialysis there is a small amount of waste removed along with the fluid gained between dialysis sessions, however, the solute drag from the removal of that ultrafiltrate is not enough to provide convective clearance).

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD (HF, HDF) treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that frequent treatments remove more toxins and waste products than a patient receiving less frequent but perhaps longer treatments. A patient receiving treatments more frequently does not experience as much of a down cycle as does an in-center patient, who has built-up two or three days' worth of toxins prior to treatment. In certain areas, the closest dialysis center can be many miles from the patient's home causing door-to-door treatment time to consume a large portion of the day. HHD may take place overnight or during the day while the patient relaxes, works or is otherwise productive.

Another type of kidney failure therapy is peritoneal dialysis, which infuses a dialysis solution, also called dialysis fluid, into a patient's peritoneal cavity via a catheter. The dialysis fluid contacts the peritoneal membrane of the peritoneal cavity. Waste, toxins and excess water pass from the patient's bloodstream, through the peritoneal membrane and into the dialysis fluid due to diffusion and osmosis, i.e., an osmotic gradient occurs across the membrane. An osmotic agent in dialysis provides the osmotic gradient. The used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), and tidal flow dialysis and continuous flow peritoneal dialysis ("CFPD"). CAPD is a manual dialysis treatment. Here, the patient manually connects an implanted catheter to a drain to allow used or spent dialysate fluid to drain from the peritoneal cavity. The patient then connects the catheter to a bag of fresh dialysis fluid to infuse fresh dialysis fluid through the catheter and into the patient. The patient disconnects the catheter from the fresh dialysis fluid bag and allows the dialysis fluid to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to perform the treatment cycles manually and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal cavity. APD machines also allow for the dialysis fluid to dwell within the cavity and for the transfer of waste, toxins and excess water to take place. The source may include multiple sterile dialysis fluid bags.

APD machines pump used or spent dialysate from the peritoneal cavity, though the catheter, and to the drain. As with the manual process, several drain, fill and dwell cycles occur during dialysis. A "last fill" occurs at the end of APD and remains in the peritoneal cavity of the patient until the next treatment.

Any of the above modalities performed by a machine may be run on a scheduled basis and may require a start-up procedure. For example, dialysis patients typically perform treatment on a scheduled basis, such as every other day, daily, etc. Blood treatment machines typically require a certain amount of time before treatment for setup, for example, to run a disinfection procedure. Patients for the above modalities may lead busy lives and have projects to perform or errands to run on a day scheduled for treatment.

Much of the appeal of a home treatment for the patient revolves around the lifestyle flexibility provided by allowing the patient to perform treatment in his or her home largely according to his or her own schedule. The home medical fluid delivery machine may however include software timers that dictate to and constrain the user or patient. A home hemodialysis system may for example require the patient to be in immediate proximity to the home hemodialysis machine to initiate pre-treatment, during treatment, and post-treatment sequences.

In one particular example, a home therapy machine may reuse certain components by disinfecting them in between treatments. The machine may employ one or more disinfection timer that requires the patient or caregiver to start a treatment using the machine before the disinfection timer expires. Otherwise, the patient will have to wait until another disinfection procedure is completed before starting treatment. The home therapy machine in an embodiment communicates the treatment start time deadlines via the machine's graphical user interface, which requires the patient to be in the proximity of the machine to access the start time deadlines and react accordingly.

It should be appreciated that the present disclosure applies to any type of disinfection, such as, hot water disinfection and chemical disinfection. In this regard, the present disclosure is not limited to home therapy machines, for example, in-center machines are typically chemically disinfected and may set a treatment start deadline after such disinfection.

Further additionally, the present disclosure is not limited to start time deadlines based upon disinfection but may also be applied to other start time deadlines, e.g., ones based upon the completion of priming. Still further, the present disclosure is not limited to initial start time deadlines. For example, most machines will allow the patient to temporarily stop treatment and disconnect from the machine to perform some type of necessary action away from the machine. For a blood treatment, the machine will typically rinse blood back to the patient and may or may not circulate the dialysis fluid for a period of time. In either case, the time that the patient may be temporarily disconnected from the machine is not unlimited, and it is contemplated that the present disclosure also applies to the return time limit.

In one embodiment, the system of the present disclosure provides a software application ("app") that is installed on the patient's and/or caregiver's personal mobile communication device, e.g., smartphone. The app is provided in one embodiment via a middleware software application, an example of which is discussed in detail below. In an alternative embodiment, the software is configured to communicate with the patient's and/or caregiver's personal mobile communication device, e.g., smartphone, directly using a text messaging feature through a middleware software application. In either case, the app or text message is structured in one embodiment to remind the patient of any impending deadline and to allow the patient and/or caregiver to keep track of when a treatment needs to start without tethering the patient to the machine.

It is contemplated to alternatively or additionally structure the communication software to program reminders automatically on the user's mobile communication device, for example, on the device's native task tracking features, such as a calendar application. Most smartphones are provided with a calendar that separates each day into time segments, such as hours. The software of the system and methodology of the present disclosure may be programmed to access the smartphone calendars of authorized patients and/or caregivers and to populate the appropriate time segment(s) of the appropriate day with the appropriate information, for example, that the machine is to begin or complete disinfection within that time segment.

In one embodiment, communication from the software system and methodology of the present disclosure is one-way. For example, communication may be from the medical fluid delivery machine, which may be a home machine, to a patient or caregiver's mobile communication device. In an alternative embodiment, the software system and methodology of the present disclosure enables two-directional communication between the medical fluid delivery machine and the patient or caregiver's mobile communication device. In one example, the two-way communication may allow for certain machine routines to be started remotely by the patient or caregiver using their mobile communication device. One example routine is an automated self-test routine, which may be performed without any user interaction with the system other than initiating or starting the sequence. Starting the sequence remotely may benefit the patient or caregiver, e.g., by providing additional time that the patient or caregiver may be away from the machine performing other tasks. The communication becomes two-way when the machine initiates the communication by indicating that the machine is ready to perform the self-test routine. The patient or caregiver at a desired time responds back to the machine via the software system and methodology of the present disclosure to initiate the sequence.

It is contemplated for the software of the system and methodology of the present disclosure to disable communication between the patient and/or caregiver and the machine whenever the machine is in a "patient connected" software state. For example, if a clinician tries to send a command to a machine currently treating a patient, the command may be intercepted by the middleware software application so that the command is not transferred to the machine. The middleware software application may then communicate back to the clinician informing that the machine is busy and not accepting communication.

The examples described herein are applicable to any medical fluid delivery system that delivers a medical fluid, such as blood, dialysis fluid, substitution fluid or and intravenous drug ("IV"). The examples are particularly well suited for kidney failure therapies, such as all forms of hemodialysis ("HD"), hemofiltration ("HF"), hemodiafiltration ("HDF"), continuous renal replacement therapies ("CRRT") and peritoneal dialysis ("PD"), referred to herein collectively or generally individually as renal failure therapy. The medical fluid delivery machines may alternatively be a drug delivery or nutritional fluid delivery device, such as a large volume peristaltic type pump or a syringe pump. The machines described herein may be used in home settings. For example, a machine operating with the data transfer regime of the present disclosure may be employed with a home HD machine, which can for example be run at night while the patient is sleeping. The medical fluid data transfer system and methodology of the present disclosure may alternatively be used to help clinicians or nurses in hospitals and/or clinics.

Referring now to the drawings and in particular to FIG. 1, a medical fluid data transfer system 10 is illustrated operating within a medical fluid delivery machine 90. System 10 incorporates many medical fluid delivery machines 90 (one type of which is discussed in detail below). Machines 90 of data transfer system 10 may be of a same type (e.g., all HD machines) or be of different types (e.g., a mix of HD, PD, CRRT, and medical or nutritional fluid delivery).

While a single medical fluid delivery 90 is illustrated as communicating with a connectivity server 118, system 10 oversees the operation of a plurality of medical fluid delivery systems and machines, of the same type or of different types listed above. For example, there may be M number of hemodialysis machines 90, N number of hemofiltration machines 90, O number of CRRT machines 90, P number of peritoneal dialysis machines 90, Q number of home drug delivery machines 90, and R number of nutritional or drug delivery machines 90 connected to server 118 and operating with system 10. The numbers M through R may be the same or different numbers, and may be zero, one, or more than one. In FIG. 1, medical fluid delivery machine 90 is illustrated as a home therapy machine 90 (the home indicated by dashed lines).

Home therapy machine 90 may receive at its front end purified water from a water treatment device 60 as discussed above. Water treatment device 60 connects to home therapy machine 90 via an Ethernet cable in an embodiment. Home therapy machines 90 in the illustrated embodiment operate with other devices besides water treatment device 60, such as a blood pressure monitor 104, a weigh scale, e.g., wireless weigh scale 106, and a user interface such as a wireless tablet user interface 122. Home therapy machine 90 connects to server 118 wirelessly in one embodiment via a modem 102. Each of these components may (but does not have to be) located within the patient's home, as demarcated by the dashed lines in FIG. 1. Any one, or more, or all of components 60, 104, 106 and 122 may communicate wired or wirelessly with home therapy machine 90. Wireless communication may be via Bluetooth™, WiFi™, Zigbee®, Z-Wave®, wireless Universal Serial Bus ("USB"), infrared, or any other suitable wireless communication technology. Alternatively, any one, or more or all of components 60, 104, 106 and 122 may communicate with home therapy machine 90 via wired communication.

Connectivity server 118 communicates with medical fluid delivery machine 90 via a medical device system hub 120. System hub 120 enables data and information concerning each home therapy machine 90 and its peripherals to travel back and forth via connectivity server 118 between machines 90 and the other clients connected to server 118. In the illustrated embodiment, system hub 120 is connected to a service portal 130, an enterprise resource planning system 140, a web portal 150, a business intelligence portal 160, a HIPAA compliant database 124, a product development team 128 and electronic medical records databases maintained for example at clinics or hospitals 126a to 126n.

Electronic medical records ("EMR") databases at clinics or hospitals 126a to 126n store electronic information concerning patients. System hub 120 may send the data collected from log files of machine 90 to hospital or clinic databases 126a to 126n to merge or supplement that patient's medical records. Databases at clinics or hospitals 126a to 126n may contain patient-specific treatment and prescription data and therefore access to such databases may be highly restricted. Enterprise resource planning system 140 obtains and compiles data generated via the patient and clinician website access, such as complaints, billing information and life cycle management information. Web portal 150 enables patients and clinics 152a to 152n treating the patients to access a website publicly available for users of medical fluid delivery machines 90. Business intelligence portal 160 collects data from system hub 120 and provides data to marketing 162, research and development 164, and quality/pharmacovigilance 166.

It should be appreciated that the systems, methods and procedures described herein may be implemented using one or more computer program or component. The programs of components may be provided as a series of computer instructions on any conventional computer-readable medium, including random access memory ("RAM"), read only memory ("ROM"), flash memory, magnetic or optical disks, optical memory, or other storage media. The instructions may be configured to be executed by a processor, which when executing the series of computer instructions performs or facilitates the performance of all or part of the disclosed methods and procedures.

In one embodiment, home therapy machine 90 performs a home treatment, such as home hemodialysis on a patient at the patient's home and then reports the results of that treatment to clinicians, doctors and nurses who are responsible for managing the health and well-being of that patient.

Home therapy machines 90 in an embodiment write log files using, e.g., a Linux™ operating system. The log files document pertinent home therapy machine 90 data, including peripheral device data. The log files may include any one or more of Extensible Markup Language ("XML"), comma-separated values ("CSV") or text files. The log files are placed into a file server box of the software of home therapy machine 90. It is also contemplated to store data at a peripheral device, e.g., water treatment device 60, which is not sent to machine 90. Such data may otherwise be obtained via the wired or wireless connection to the peripheral device or downloaded through other data connections or storage media. For example, a service person can access additional data via a laptop connected to water treatment device 60 or wireless weigh scale 106, e.g., via an Ethernet connection. Or, the additional data may be retrieved remotely from the peripheral devices, with home therapy machine 90 serving as the data transfer liaison between the peripheral device and authorized clients of medical fluid data transfer system.

In one embodiment, home therapy machine 90, e.g., via the internet, uses a connectivity service to transfer data between modem 102 and system hub 120. Here, a dedicated line may be provided at each patient's home for connecting the home therapy machine 90 to the connectivity server 118 via modem 102. Home therapy machine 90 in one embodiment accesses the internet using a separate, e.g., 3G, 4G or 5G, modem 102. Modem 102 may use an internet Service Provider ("ISP"), such as Vodafone™. In one implementation, a connectivity agent 114 developed by a connectivity service provider (e.g., provider of connectivity server 118) is installed onto the home therapy machine 90 and run on ACPU 50 of the machine. One suitable connectivity service is provided by Axeda™, which provides a secure managed connection 116 between medical devices and the connectivity server 118.

Connectivity agent 114 allows the home therapy machine 90 to connect to connectivity server 118 and transfer data to and from the connectivity server 118. The connectivity service operating via agent 114 and server 118 ensures that the connection with machine 90 is secure, ensures that the data correctly passes through machine 90's firewalls, checks whether there has been a data or system crash, and ensures that connectivity server 118 is communicating with the correct home therapy machine 90.

In one embodiment, home therapy machine 90 may only connect to connectivity server 118 when connectivity agent 114 is turned on or activated. During treatment and post-treatment disinfection, while machine 90 and its peripherals are functioning, connectivity agent 114 is turned off if one embodiment, which prevents home therapy machine 90 from communicating with any entity and sending or receiving data during treatment and disinfection or when machine 90 is live or running. When home therapy machine 90 is idle, e.g., after treatment and post-disinfection is complete, ACPU 50 turns connectivity agent 114 on in one embodiment. In an embodiment, connectivity agent 114 is off during treatment and possibly pretreatment. After treatment, connectivity agent 114 retrieves the log files from the home therapy machine 90 and transfers data to the connectivity server 118 using the connectivity service. The connectivity service routes data packets to their proper destination but in one embodiment does not modify, access, or encrypt the data.

In medical fluid data transfer system 10 system of FIG. 1, the connectivity service via connectivity server 118 may communicate data to various places via a system hub 120, such as a service portal 130, clinics or hospitals 126a to 126n, and a web portal 150. Connectivity server 118 allows service personnel 132a to 132n and/or clinicians to track and retrieve various assets across the network, such as appropriate home therapy machines 90 and 3G, 4G or 5G modem 102, and their associated information, including machine or modem serial numbers. Connectivity server 118 may also be used to receive and provide firmware upgrades, approved by a director of service personnel 134 and obtained remotely via service portal 130, to authorized home therapy machines 90 and associated peripherals, such as water treatment devices 60.

A. Example Medical Fluid Delivery Machine

Figure 2:
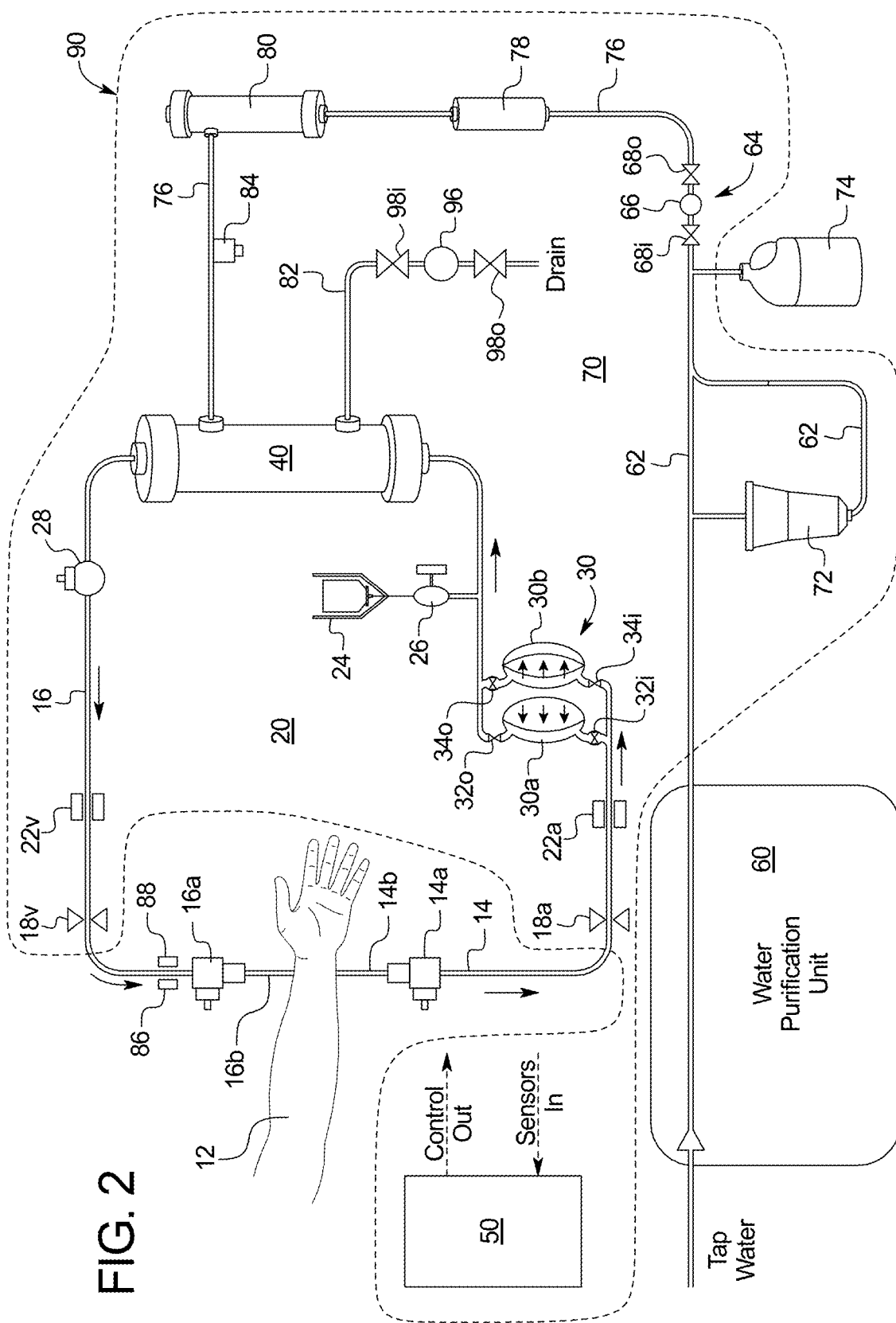
FIG. 2 is a schematic illustration of one embodiment of a medical fluid delivery machine of the present disclosure.

Referring now to FIG. 2, an example of an HD flow schematic for medical fluid delivery machine 90 is illustrated. Because the HD system of FIG. 2 is relatively complicated, FIG. 2 and its discussion also provide support for any of the renal failure therapy modalities discussed above and for an IV, drug delivery, or nutritional fluid delivery machine. Generally, medical fluid delivery machine 90 is shown having a simplified version of a dialysis fluid or process fluid delivery circuit. The blood circuit is also simplified but not to the degree that the dialysis fluid circuit is simplified. It should be appreciated that the circuits have been simplified to make the description of the present disclosure easier, and that the systems if implemented would have additional structure and functionality, such as is found in the publications incorporated by reference above.

Medical fluid delivery machine 90 of FIG. 2 includes a blood circuit 20. Blood circuit 20 pulls blood from and returns blood to a patient 12. Blood is pulled from patient 12 via an arterial line 14, and is returned to the patient via a venous line 16. Arterial line 14 includes an arterial line connector 14a that connects to an arterial needle 14b, which is in blood draw communication with patient 12. Venous line 16 includes a venous line connector 16a that connects to a venous needle 16b, which is in blood return communication with the patient. Arterial and venous lines 14 and 16 also include line clamps 18a and 18v, which can be spring-loaded, fail-safe mechanical pinch clamps. Line clamps 18a and 18v are closed automatically in an emergency situation in one embodiment.

Arterial and venous lines 14 and 16 also include air or bubble detectors 22a and 22v, respectively, which can be ultrasonic air detectors. Air or bubble detectors 22a and 22v look for air in the arterial and venous lines 14 and 16, respectively. If air is detected by one of air detectors 22a and 22v, system 10 closes line clamps 18a and 18v, pauses the blood and dialysis fluid pumps, and provides instructions to the patient to clear the air so that treatment can resume.

A blood pump 30 is located in arterial line 14 in the illustrated embodiment. In the illustrated embodiment, blood pump 30 includes a first blood pump pod 30a and a second blood pump pod 30b. Blood pump pod 30a operates with an inlet valve 32i and an outlet valve 32o. Blood pump pod 30b operates with an inlet valve 34i and an outlet valve 34o. In an embodiment, blood pump pods 30a and 30b are each blood receptacles that include a hard outer shell, e.g., spherical, with a flexible diaphragm located within the shell, forming a diaphragm pump. One side of each diaphragm receives blood, while the other side of each diaphragm is operated by negative and positive air pressure. Blood pump 30 is alternatively a peristaltic pump operating with the arterial line 14 or multiple peristaltic pumps operating with arterial line 14 and venous line 16.

A heparin vial 24 and heparin pump 26 are located between blood pump 30 and blood filter 40 (e.g., dialyzer) in the illustrated embodiment. Heparin pump 26 may be a pneumatic pump or a syringe pump (e.g., stepper motor driven syringe pump). Supplying heparin upstream of blood filter 40 helps to prevent clotting of the filter's membranes.

A primary control processor ("ACPU") or control unit control unit 50 includes one or more processor and memory. Control unit 50 receives air detection signals from air detectors 22a and 22v (and other sensors of system 10, such as temperature sensors, blood leak detectors, conductivity sensors, pressure sensors, and access disconnection transducers 86, 88), and controls components such as line clamps 18a and 18v, blood pump 30, heparin pump 26, dialysis fluid pumps 64 and 96, and valves 32i, 32o, 34i, 34o, 68i, 68o, 98i and 98o. Blood exiting blood filter 40 via venous line 16 flows through an air trap 28. Air trap 28 removes air from the blood before the dialyzed blood is returned to patient 12 via venous line 16.

With the hemodialysis version of medical fluid delivery machine 90 of FIG. 2, dialysis fluid is pumped along the outside of the membranes of blood filter 40, while blood is pumped through the insides of the blood filter membranes. Dialysis fluid is prepared beginning with the purification of water via a water purification unit 60. One suitable water purification unit is set forth in U.S. Patent Publication No. 2011/0197971, entitled, "Water Purification System and Method", filed Apr. 25, 2011, the entire contents of which are incorporated herein by reference and relied upon. In one embodiment, water purification unit includes filters and other structures to purify tap water (e.g., remove pathogens and ions such as chlorine), so that the water is in one implementation below 0.03 endotoxin units/ml ("EU/ml") and below 0.1 colony forming units/ml ("CFU/ml"). Water purification unit 60 may be provided in a housing separate from the housing or chassis of the hemodialysis machine 90, which includes blood circuit 20 and dialysis fluid circuit 70.

Dialysis fluid circuit 70 is again highly simplified in FIG. 2 to ease illustration. Dialysis fluid circuit 70 in actuality may include all of the relevant structure and functionality set forth in the publications incorporated by reference above. Certain features of dialysis fluid circuit 70 are illustrated in FIG. 2. In the illustrated embodiment, dialysis fluid circuit 70 includes a to-blood filter dialysis fluid pump 64. Pump 64 is in one embodiment configured the same as blood pump 30. Pump 64, like pump 30, includes a pair of pump pods 66 each having inlet valves 68i and outlet valves 68o, which again may be spherically configured. The two pump pods, like with blood pump 30, are operated alternatingly so that one pump pod is filling with HD dialysis fluid, while the other pump pod is expelling HD dialysis fluid.

Pump 64 is a to-blood filter dialysis fluid pump. There is another dual pod pump chamber 96 operating with valves 98i and 98o located in drain line 82 to push used dialysis fluid to drain. There is a third pod pump (not illustrated) for pumping pump purified water through a bicarbonate cartridge 72. There is a fourth pod pump (not illustrated) used to pump acid from acid container 74 into mixing line 62. The third and fourth pumps, the concentrate pumps, may be single pod pumps because continuous pumping is not as important in mixing line 62 due to a buffering dialysis fluid tank (not illustrated) between mixing line 62 and to-blood filter dialysis fluid pump 64 in one embodiment.

A fifth pod pump (not illustrated) provided in drain line 82 is used to remove a known amount of ultrafiltration ("UF") when an HD therapy is provided. System 10 keeps track of the UF pump to control and know how much ultrafiltrate has been removed from the patient. System 10 ensures that the necessary amount of ultrafiltrate is removed from the patient by the end of treatment.

Each of the above-described pumps may alternatively be a peristaltic pump operating with a pumping tube. If so, the system valves may still be actuated pneumatically according to the features of the present disclosure.

In one embodiment, purified water from water purification unit 60 is pumped along mixing line 62 though bicarbonate cartridge 72. Acid from container 74 is pumped along mixing line 62 into the bicarbonated water flowing from bicarbonate cartridge 72 to form an electrolytically and physiologically compatible dialysis fluid solution. The pumps and temperature-compensated conductivity sensors used to properly mix the purified water with the bicarbonate and acid are not illustrated but are disclosed in detail in the publications incorporated by reference above.

FIG. 2 also illustrates that dialysis fluid is pumped along a fresh dialysis fluid line 76, through a heater 78 and an ultrafilter 80, before reaching blood filter 40, after which used dialysis fluid is pumped to drain via drain line 82. Heater 78 heats the dialysis fluid to body temperature or about 37° C. Ultrafilter 80 further cleans and purifies the dialysis fluid before reaching blood filter 40, filtering foreign matter and/or contaminants introduced for example via bicarbonate cartridge 72 or acid container 74 from the dialysis fluid.

Dialysis fluid circuit 70 also includes a sample port 84 in the illustrated embodiment. Dialysis fluid circuit 70 will further include a blood leak detector (not illustrated but used to detect if a blood filter 40 fiber is torn) and other components that are not illustrated, such as balance chambers, plural dialysis fluid valves, and a dialysis fluid holding tank, all illustrated and described in detail in the publications incorporated by reference above.

In the illustrated embodiment, medical fluid delivery machine 90 is an online, pass-through system that pumps dialysis fluid through blood filter one time and then pumps the used dialysis fluid to drain. Both blood circuit 20 and dialysis fluid circuit 70 may be hot water disinfected after each treatment, such that blood circuit 20 and dialysis fluid circuit 70 may be reused. In one implementation, blood circuit 20 including blood filter 40 is hot water disinfected and reused daily for about one month, while dialysis fluid circuit 70 is hot water disinfected and reused for about six months.

In alternative embodiments, for CRRT for example, multiple bags of sterilized dialysis fluid or infusate are ganged together and used one after another. In such a case, the emptied supply bags can serve as drain or spent fluid bags.

Medical fluid delivery machine 90 includes an enclosure as indicated by the dashed line of FIG. 2. The enclosure of machine 90 varies depending upon the type of treatment, whether the treatment is in-center or a home treatment, and whether the dialysis fluid/infusate supply is a batch-type (e.g., bagged) or on-line.

Figure 3:
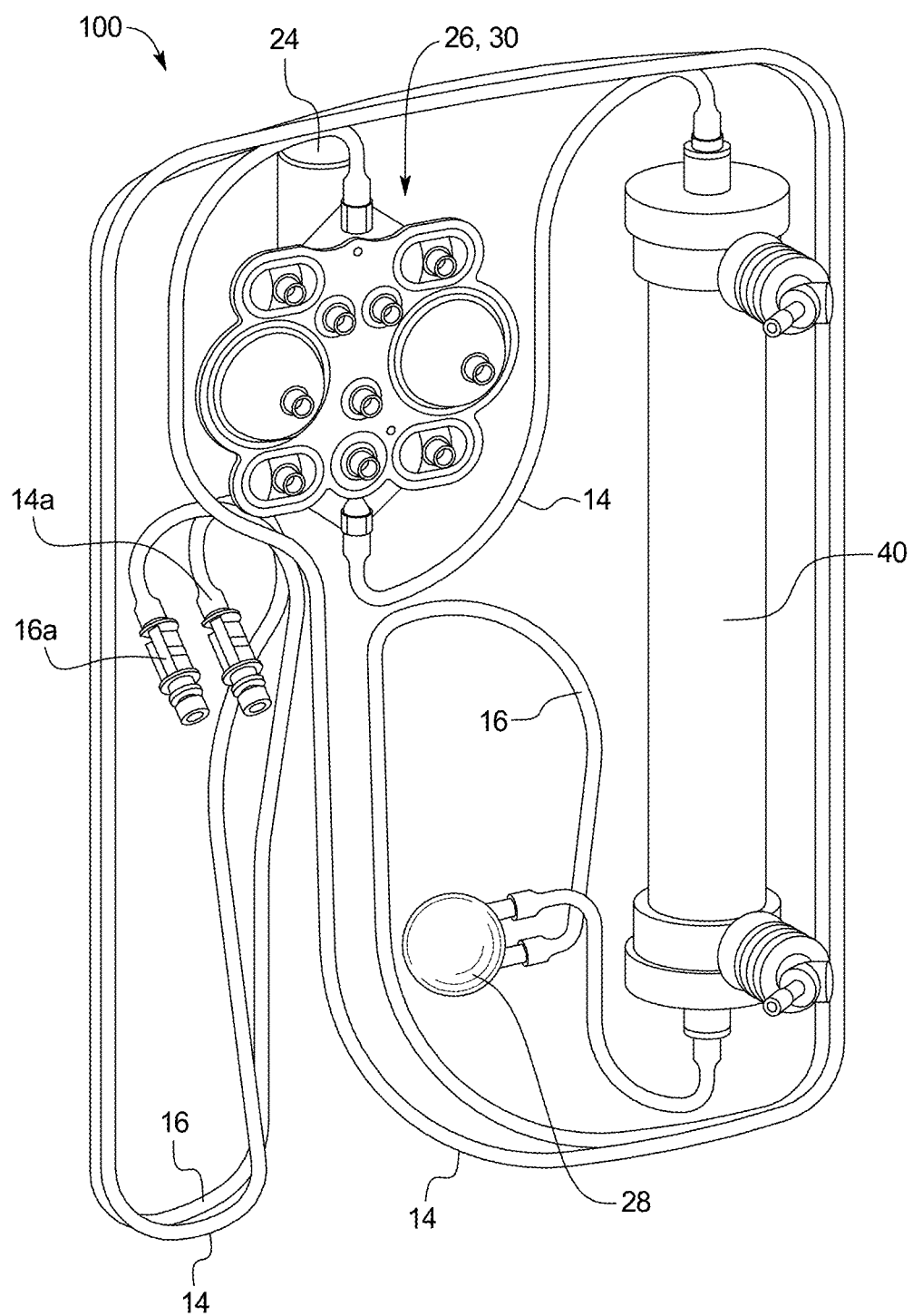
FIG. 3 is a perspective view illustrating a blood set for use with one embodiment of the medical fluid delivery machine of FIG. 2, according to an embodiment of the present disclosure.

FIG. 3 illustrates that machine 90 of FIG. 2 may operate with a blood set 100. Blood set 100 includes arterial line 14, venous line 16, heparin vial 24, heparin pump 26/blood pump 30 and blood filter 40 (e.g., dialyzer). An air trap 28 may be located in venous line 16 to remove air from the blood before being returned to patient 12. Air detectors 22a and 22v contact arterial and venous lines 14 and 16, respectively, for operation.

In FIGS. 2 and 3, any of pumps 26, 30 (30a and 30b), 64, 96 (and other pumps not illustrated) and any of the valves, such as valves 32i, 32o, 34i, 34o, 68i, 68o, 98i, and 98o may be pneumatically actuated. In an embodiment, each of the pumps and valves has a fluid side and an air side, separated by a flexible membrane. Negative pneumatic pressure may be applied to the air side of the membrane to draw fluid into a pump chamber or to open a valve (or the pump or valve could be opened by venting positive closing pressure to atmosphere and allowing fluid pressure to open). Positive pneumatic pressure is applied to the air side of the membrane to expel fluid from a pump chamber or to close a valve.

B. Connectivity Embodiments of the Example Medical Fluid Delivery System

Figure 4:
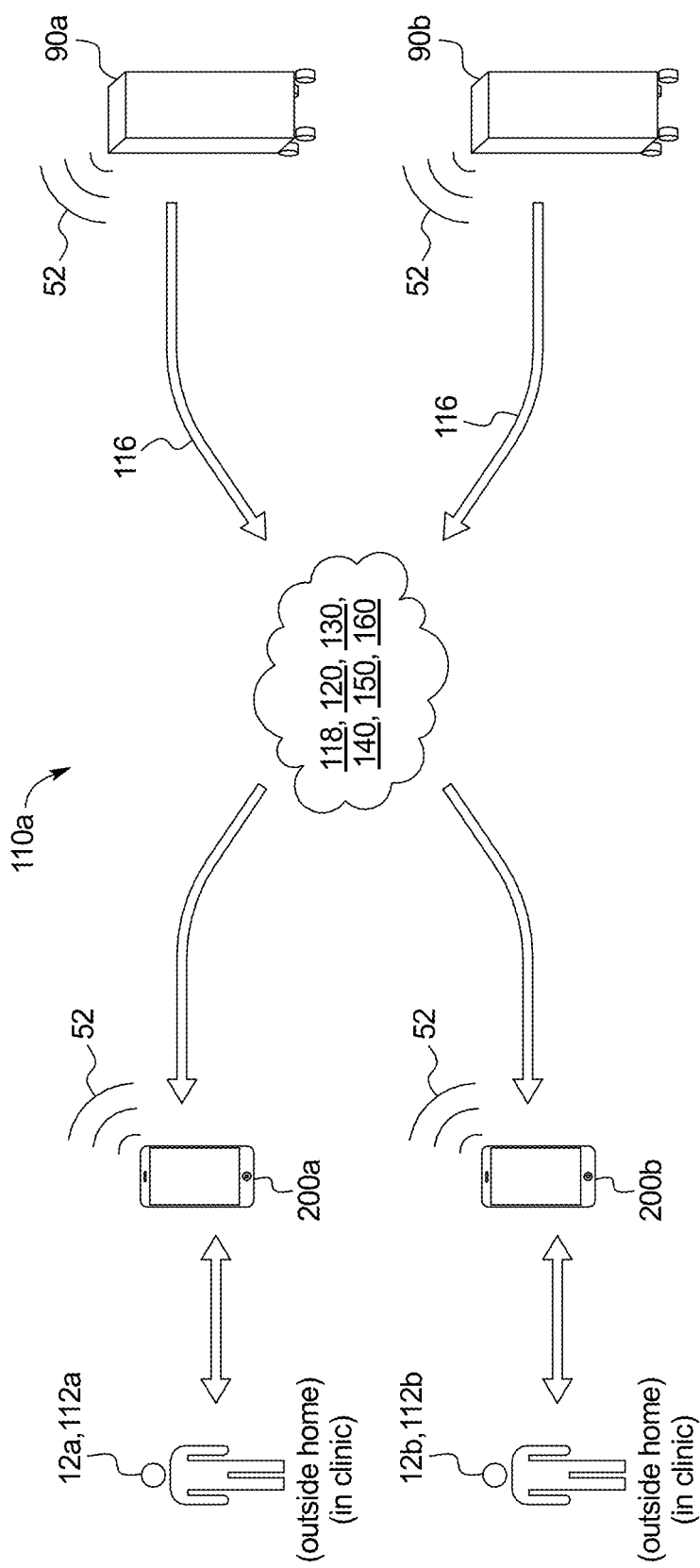
FIG. 4 is a schematic view of one embodiment for a medical fluid delivery machine and data transfer system and method of the present disclosure.

Referring now to FIG. 4, a system 110a of the present disclosure is illustrated. System 110a in the illustrated embodiment operates with system 10 described above, including connectivity server 118, system hub 120, service portal 130, enterprise resource planning system 140, web portal 150, and business intelligence portal 160, which are illustrated in FIG. 4 as being part of a cloud environment. Connectivity server 118, system hub 120, service portal 130, enterprise resource planning system 140, web portal 150, and business intelligence portal 160 may each be part of a cloud environment or be located at one or more dedicated server.

Other components of system 10 not illustrated in FIG. 4 may also be part of system 110a. For instance, medical fluid delivery machines 90a and 90b may reside separately in the homes of patients 12a and 12b (who are illustrated as being outside the home). Alternatively, medical fluid delivery machines 90a and 90b may reside in the same clinic 126a to 126n or in different ones of clinics 126a to 126n. Clinicians 112a and 112b may reside inside or outside of the clinics.

Medical fluid delivery machines 90a and 90b are connected to connectivity server 118 via secure managed connections 116 as described above. To do so, machines 90a and 90b connect to internet 52, e.g., via modems 102 discussed above. System hub 120 in one embodiment stores middleware software that may be accessed by mobile communication devices 200a and 200b (referred to herein collectively as devices 200 or generally individually as device 200). Mobile communication devices 200a and 200b may be smartphones, for example, running on Android™, iOS™, Windows Phone™, BlackBerry™, Sailfish OS™, Tizen™, or Ubuntu Touch™ operating systems. Mobile communication devices 200a and 200b may belong to patients 12a and 12b, respectively, and/or clinicians 112a and 112b, respectively. Mobile communication devices 200a and 200b as illustrated in FIG. 4 are also connected to internet 52.

In one embodiment, mobile communication devices 200a and 200b download application software ("app") from middleware software stored on system hub 120 via their connection to internet 52. The app is updated whenever there is a change of state of the corresponding machine 90a or 90b. For example, medical fluid delivery machine 90a may have just completed its automated self-test routine and is now ready to run a disinfection procedure. Machine 90a may generate a code identifying this state and send it to middleware software stored on system hub 120. Middleware software then translates the code into a message, e.g., using a look-up table, such as, "self-test completed, ready for disinfection" and cause the app downloaded onto mobile communication device 200a of patient 12a or clinician 112a to display the message. The app may be programmed to provide a visual identifier along with the message, such as, an icon that is associated with the particular state in which machine 90a resides. The app may also provide any one or more of an audio alert, such as a "ding" sound, and/or a haptic alert, such as a vibration, which prompt patient 12a or clinician 112a to view the app and see the state change of machine 90.

In another example, medical fluid delivery machine 90b may have been preprogrammed to begin treatment at 3:00 PM. Medical fluid delivery machine 90b may need three hours for self-test and disinfection. Patient 12a or clinician 112a therefore needs to be at machine 90b by noon to start pre-treatment. In an embodiment, patient 12a or clinician 112a makes a setting on machine 90b as to how soon before the three hour preparation time that the patient 12a or clinician 112a should be notified or alerted, e.g., two hours. So in this example, machine 90b may generate a code at 10:00 AM and send the code to middleware software stored on system hub 120. Middleware software then translates the code into a message, e.g., using a look-up table, such as, "treatment preparation needs to start in two hours" and cause the app downloaded onto mobile communication device 200b of patient 12b or clinician 112b to display the message. The app may again be programmed to provide a visual identifier along with the message, such as, a countdown timer that counts down from one-hundred-twenty minutes to a timeout at zero. The app may also provide any one or more of an audio alert, such as a "ding" sound, and/or a haptic alert, such as a vibration, which prompt patient 12b or clinician 112b to view the app and see the treatment preparation notification. The app may also be programmed to repeat the "ding" sound and/or haptic feedback at preprogrammed intervals during the countdown period, e.g., at an hour and at thirty minutes.

In addition or alternatively to providing the app on the user's communication device 200b, it is contemplated for the middleware software at system hub 120 to convert the code from machine 90b into a message that is lodged onto device 200's native task tracking feature, such as its calendar application. Most smartphone devices 200, for example, are provided with a calendar that separates each day into time segments, such as hours. Here, the message converted by middleware software of system hub 120 may be programmed to access the calendar of authorized communication device 200b and to populate the appropriate time segment of the appropriate day with the appropriate information. In the above example, for the appropriate day, the native calendar software application will have its 10:0:00 AM timeslot filled with a message, such as, "treatment preparation needs to start in two hours". An audio and/or haptic feedback signal may be provided to notify patient 12 or clinician 112 about the calendar entry.

It should be appreciated that machines 90a and 90b, middleware software at central server 120, and communication devices 200a and 200b, may be programmed and operated as described above to provide any desired message to patients 12a, 12b and/or clinicians 112a, 112b and are not limited to the messages described herein. For example, patients 12a, 12b and/or clinicians 112a, 112b may be likewise informed at the end of disinfection with an accompanying countdown timer that treatment needs to start within the countdown time to avoid having to re-disinfect machine 90a, 90b.

Figure 5:
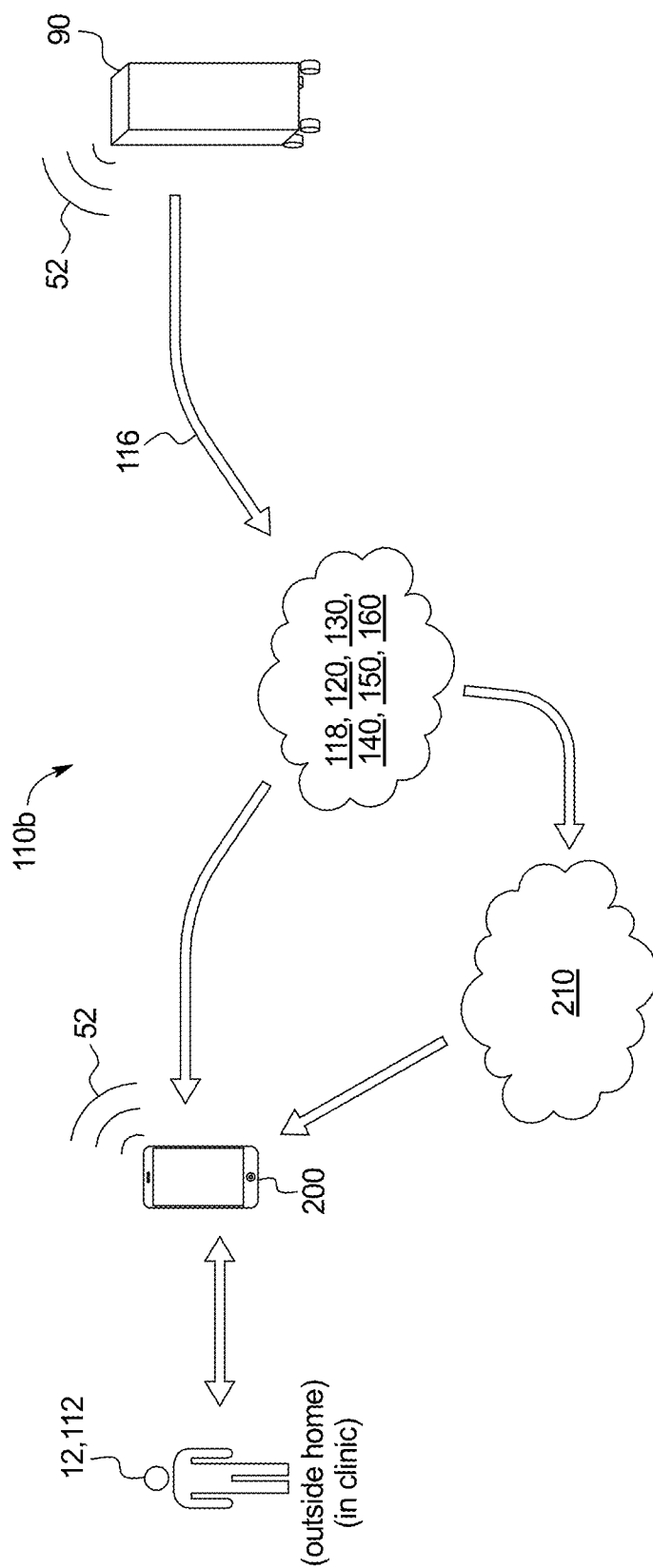
FIG. 5 is a schematic view of a second embodiment for a medical fluid delivery machine and data transfer system and method of the present disclosure.

Referring now to FIG. 5, a system 110b of the present disclosure is illustrated. System 110b in the illustrated embodiment operates with system 10 described above, including connectivity server 118, system hub 120, service portal 130, enterprise resource planning system 140, web portal 150, and business intelligence portal 160, which are illustrated in FIG. 5 as being part of a cloud environment, but may be located alternatively at one or more dedicated server. Other components of system 10 not illustrated in FIG. 5 may also be part of system 110a. A single medical fluid delivery machine 90 is illustrated for ease of description, however, multiple medical fluid delivery machines 90 may be likewise connected to system 110b. Medical fluid delivery machine 90 may reside in the home of patient 12 (illustrated as being outside the home) or in a clinic 126a to 126n for clinician 112. Medical fluid delivery machine 90 is connected again to connectivity server 118 via secure managed connection 116 and an internet 52 connection using, e.g., modem 102 in the illustrated embodiment.

System hub 120 in one embodiment stores middleware software that may be accessed by mobile communication device 200 (shown as single device for ease, but multiple devices 200 may be likewise connected to system 110b). Mobile communication devices 200 in FIG. 5 include all of the structure, functionality and alternatives disclosed for devices 200a and 200b illustrated in FIG. 4, including being connected to internet 52. In FIG. 5, mobile communication device 200 may, but does not have to, download a software application ("app") from middleware software stored on system hub 120 via their connection to internet 52. The app may be operated exactly as described above in connection with FIG. 4, including middleware software converting a coded message from machine 90 into a format presentable on the app. Alternatively or additionally, middleware software stored on system hub 120 may be able to convert the code from machine 90 into a message that is lodged onto mobile communication device 200's native task tracking feature, such as its calendar application, in any of the ways described in FIG. 4.

Further alternatively or additionally, system 110b includes a cellular network 210 that interfaces between middleware software, e.g., stored at system hub 120, and mobile communication device 200. Cellular network 210 may include a network of cellular phone towers operating using radio waves and/or employ a satellite. Communication protocols suitable for use with cellular network 210 of system 110b may be long range protocols, such as (i) the "worldwide interoperability for microwave access" ("WiMAX") protocol; and (ii) the "global system for mobile communications" ("GSM") protocol, which is a widespread long-range wireless protocol enabling data communication to the many of the world's cellular telephones. Network 210 may alternatively or additionally employ a medium range protocol, such as a wireless local area network ("WLAN"), which can be a protocol that is part of the Institute of Electrical & Electronics Engineers ("IEEE") 802.11 standard, such as (i) IEEE 802.11a, (ii) IEEE 802.11b, (iii) WEE 802.11g, or (iv) 802.11n. Other suitable cellular technologies may include CDMA, AMPS (analog), General Packet Radio Service ("GPRS"), cdmaOne, CDMA2000, Evolution-Data Optimized ("EV-DO"), Enhanced Data Rates for GSM Evolution ("EDGE"), Universal Mobile Telecommunications System ("UMTS"), Digital Enhanced Cordless Telecommunications ("DECT"), Digital AMPS ("IS-136/TDMA"), and Integrated Digital Enhanced Network ("iDEN").

Mobile communication devices 200 communicate with cellular network 210 via any of the ways known to those of skill, e.g., via Short Messaging Service ("SMS") or Multimedia Messaging Service ("MIMS") protocols. Middleware software at system hub 120 may communicate with cellular network 210 in a number of ways. In one example, the phone numbers and carriers of users 12, 112 (any or all of patient 12, patient's at home care partner, patient's clinician 112) are associated, e.g., via a look-up table at middleware software, with a specific machine 90. When a message/code from a specific machine 90 is received by middleware, middleware software may be programmed to send an email to [user phone number]@[carrier].net. For example, if patient 001's phone number is (555) 555-5555 and patient 001's carrier is AT&T™, when patient 001's machine 90 sends a message to middleware software of system hub 120, upon receipt, middleware software 120 is programmed to relay an email to 5555555555@att.net, which is received by patient 001's mobile communication device 200 as a text message. Those of skill in the art understand that there are multiple websites devoted to informing how to email to a text message, outlining the specifics required by different carriers.

Middleware software stores each of the telephone numbers of each of mobile communication devices 200 and matches each of those numbers with a machine 90. When an event code is sent from a machine 90 to middleware software as has been described above, middleware software locates the telephone number of the mobile communication device 200 associated with that machine, converts the code to an appropriate message, e.g., using a look-up table as described above, and sends the converted message to the recalled telephone number. It is contemplated that multiple communication devices 200 may be associated with the same medical fluid delivery machine 90. For example, in any of clinics 126a to 126n, multiple doctor, nurse and/or clinician telephone numbers may be associated with the same machine 90. In a home environment, the telephone numbers for patient 12 and his or her clinician and/or caregiver assistant may be associated with the same machine 90.

Likewise, a telephone number for a mobile communication device 200 may be associated with multiple medical fluid delivery machines 90. For example, in any of clinics 126a to 126n, a single nurse may monitor multiple machines 90. If an event occurs to any of those machines during the nurse's shift, the nurse may be notified via a cellular message sent to the nurse's mobile communication device 200. This scenario is described in detail below in connection with FIGS. 7 to 9.

The cellular messages may convey in formation concerning any of the same events discussed above for the software app and calendar updating modes of populating mobile communication devices 200 with information. For example, medical fluid delivery machine 90 may have just completed its automated self-test routine and is now ready to run a disinfection procedure. Machine 90 may generate a code identifying this state and send it to middleware software stored on system hub 120. Middleware software then translates the code into a message, e.g., using a look-up table, such as, "self-test completed, ready for disinfection" and cause the cellular output routine discussed above for example to send a text message to mobile communication device 200 of patient 12 or clinician 112 to display the message. In an alternative embodiment, a code is not needed and machine 90 instead sends an actual text string, which middleware software forwards on to the mobile communication device 200 as a text message via the cellular output routine discussed above for example. As is known, the receipt of the text message on communication device 200 may be accompanied with an audio, e.g., "ding" sound, and/or a haptic alert, such as a vibration, which prompt patient 12 or clinician 112 to view the message.

In another example, medical fluid delivery machine 90 may have been preprogrammed to begin treatment at 3:00 PM. Medical fluid delivery machine 90 may again need three hours for self-test and disinfection. Patient 12 or clinician 112 therefore needs to be at machine 90 by noon to start pre-treatment. In an embodiment, patient 12 or clinician 112 makes a setting on machine 90 as to how soon before the three hour preparation time that patient 12 or clinician 112 should be notified or alerted, e.g., two hours. Here, machine 90 generates a code at 10:00 AM and sends the code to middleware software stored on system hub 120. Middleware software then translates the code into a message, e.g., using a look-up table, such as, "treatment preparation needs to start in two hours" and cause the cellular output routine discussed above for example to send a text message to mobile communication device 200 of patient 12 or clinician 112 to display the message, e.g., along with an audio alert, such as a "ding" sound, and/or a haptic alert, such as a vibration, which prompt patient 12 or clinician 112 to view the notification.

It should be appreciated that machine 90, middleware software at central server 120, and communication device 200 may be programmed and operated as described above to provide any desired message to patients 12 and/or clinicians 112 using cellular network 210 alternatively or additionally. For example, patients 12 and/or clinicians 112 may be likewise informed at the end of disinfection that treatment needs to start within the countdown time to avoid having to re-disinfect machine 90. It should also be appreciated that the updating of the native task tracking features, such as the calendar application of communication device 200 may be done over an internet connection or via cellular network 210 illustrated in FIG. 5.

Figure 6:
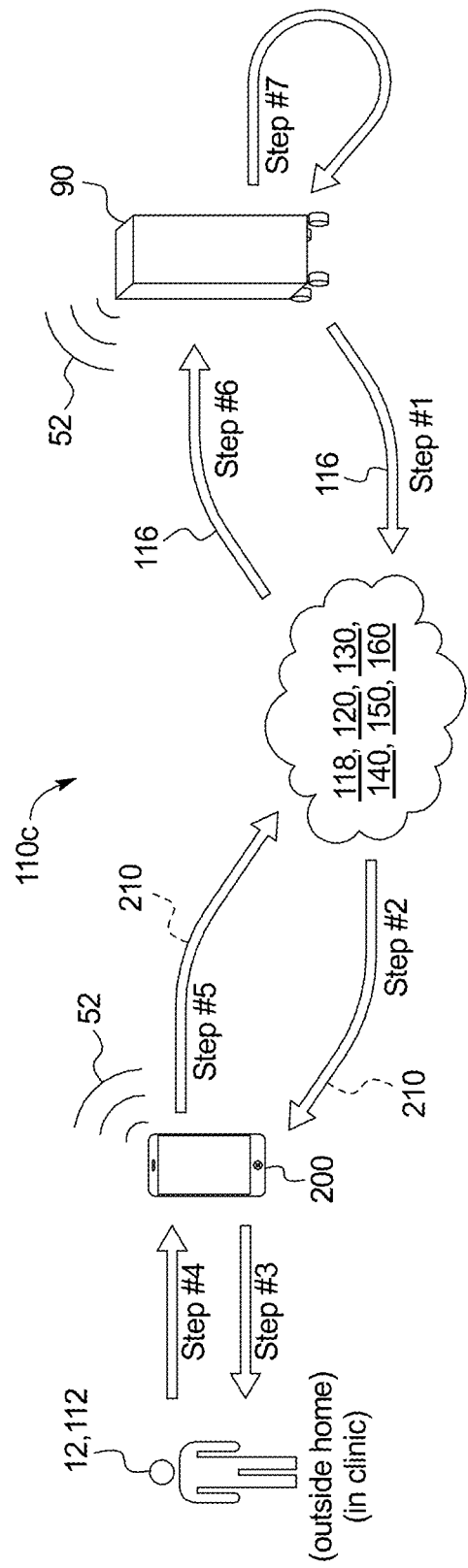
FIG. 6. is a schematic view of a third embodiment for a medical fluid delivery machine and data transfer system and method of the present disclosure.

Referring now to FIG. 6, a system 110c of the present disclosure is illustrated. System 110c in the illustrated embodiment operates with system 10 described above, including connectivity server 118, system hub 120, service portal 130, enterprise resource planning system 140, web portal 150, and business intelligence portal 160, which are illustrated in FIG. 6 as being part of a cloud environment, but may be located alternatively at one or more dedicated server. Other components of system 10 not illustrated in FIG. 6 may also be part of system 110a. A single medical fluid delivery machine 90 is illustrated for ease of description, however, multiple medical fluid delivery machines 90 may be likewise connected to system 110b. Medical fluid delivery machine 90 may reside in the home of patient 12 (illustrated as being outside the home) or in a clinic 126a to 126n for clinician 112. Medical fluid delivery machine 90 is connected again to connectivity server 118 via secure managed connection 116 and an internet 52 connection using, e.g., modem 102 in the illustrated embodiment. In FIG. 6, connectivity server 118 and secure managed connection 116 are used for two-way communication.

System hub 120 in one embodiment stores middleware software that may be accessed by mobile communication device 200 (shown as single device for ease, but multiple devices 200 may be likewise connected to system 110b). Mobile communication devices 200 in FIG. 6 include all of the structure, functionality and alternatives disclosed for devices 200a and 200b illustrated in FIG. 4, including being connected to internet 52. In FIG. 6, mobile communication device 200 may, but does not have to, download a software application ("app") from middleware software stored on system hub 120 via their connection to internet 52. The app may be operated exactly as described above in connection with FIG. 4, including middleware software converting a coded message from machine 90 into a format presentable on the app. Alternatively or additionally, middleware software stored on system hub 120 may be able to convert the code from machine 90 into a message that is lodged onto mobile communication device 200's native task tracking feature, such as its calendar application, in any of the ways described in FIG. 4. The calendar application may alternatively be updated via a cellular network 210 (illustrated as an alternative via dashed lead lines in FIG. 6) discussed above in connection with FIG. 5.

FIG. 6 illustrates that communication may be two-way between medical fluid delivery machines 90 and mobile communication devices 210. Communication between mobile communication devices 210 and middleware software at server computer 120 may be via internet 52 and/or cellular network 210. Communication between middleware software at server computer 120 may be via connectivity server 118 via secure managed connection 116 as described in detail above.

As discussed above, home therapy machine 90 connects to connectivity server 118 via its onboard connectivity agent 114, which in one embodiment is turned off during treatment (may or may not be turned off during post-treatment disinfection), e.g., while machine 90 and its peripherals are functioning. This prevents home therapy machine 90 from communicating with any entity and sending or receiving data during treatment and disinfection or when machine 90 is live or running. It is contemplated that the communication via systems 110a to 110c be protected in the same way. For instance, suppose that a particular machine 90 is set via the middleware software to communicate with both patient 12 and clinician 112. Here, if patient is being treated by machine 90, it is contemplated that connectivity agent 114 be shut off so that clinician 112 at that time cannot receive notifications from or send commands to that machine 90. In an alternative embodiment, clinician 112 may be able to receive notifications machine 90 during treatment.

Determining when to disconnect connectivity agent 114 (no communication) may be dependent upon what or how many machine states that systems 110a to 110c desire to communicate to mobile communication devices 200. For instance, suppose that it is only desired to inform patient 12 or clinician 112 two hours before treatment preparation that the patient 12 or clinician 112 needs to return to machine 90 to start treatment preparation. Here, connectivity agent 114 may be turned off as soon as patient 12 or clinician 112 begins the first treatment preparation step, e.g., running self-test routine.

In another example, it may be desired for machine 90 to run the self-test routine automatically at some preset time before treatment is set to start. Machine 90 notifies patient 12 or clinician 112 when it is time to begin disinfection. Here, connectivity agent 114 may be disconnected once patient 12 or clinician 112 begins the machine disinfection. In a further example, it may be desired for machine 90 to notify patient 12 when disinfection is complete so that the patient begins treatment within a certain amount of time from the end of disinfection, so that disinfection does not need to be repeated. Here, connectivity agent 114 may be disconnected once patient 12 or clinician 112 begins treatment, e.g., upon the beginning of prime in which the patient is still yet to be connected to treatment lines, e.g., to arterial line 14 or venous line 16.

System 110c allows patient 12 or clinician 112 to begin any of the above actions (and others not expressly described herein) remotely. Patient 12 or clinician 112 may for example select an icon on the app displayed on mobile communication device 200 to begin, e.g., the self-test routine or a disinfection procedure. The selection of the icon is transmitted over internet 52 to middleware software. Middleware software may then for example translate, e.g., via a look-up table, the icon selection into an action code that is sent via connectivity server 118 and secure managed connection 116 to machine 90 whose connectivity agent 114 is on, allowing the action code for the selected action to be sent to the machine's ACPU 50, which begins the performance of the selected action.

In an alternative embodiment, patient 12 or clinician 112 may for example enters a known code in a text message selecting a particular action to be performed at machine 90, e.g., the self-test routine or a disinfection procedure. The code may be a suggestive code, such as "self-test" or "disinfection". The text message is sent via cellular network 210 to middleware software at system hub 120. Middleware software converts, e.g., via a look-up table, the texted code into an action code for the selected action. Or, the code entered by patient 12 or clinician 112 may be the action code, so that no conversion is needed. In either case, the action code is sent via connectivity server 118 and secure managed connection 116 to machine 90 whose connectivity agent 114 is on, allowing the action code for the selected action to be sent to the machine's ACPU 50, which begins the performance of the selected action.

FIG. 6 illustrates the following example seven step sequence. In step 1, medical fluid delivery machine 90 sends a message to middleware software application at system hub 120 indicating that the machine is ready for patient 12 to initiate the start of machine 90's, e.g., two hour, automated self-test routine. In step 2, the middleware software application at system hub 120 sends a corresponding, e.g., translated, message to the patient's mobile communication device 200 indicating that machine 90 is ready for patient 12 to initiate the start of the automated self-test routine.

In step 3, a custom app downloaded to the patient's mobile communication device 200 alerts patient 12 via an audio, visual and/or haptic alert and associated message that patient 12's machine 90 is ready for the patient to initiate the start of the, e.g., two hour, automated self-test routine. In step 4, patient 12 uses the custom app on mobile communication device 200 to confirm that machine 90 should begin its automated self-test routine.

In step 5, the patient's mobile communication device 200 sends a message to middleware software application at system hub 120 confirming that it is desired for the patient's machine 90 to begin its automated self-test routine. In step 6, middleware software application at system hub 120 sends (e.g., converts and sends) a message to machine 90 indicating that patient 12 has confirmed that machine 90 is to begin its automated self-test routine. In step 7, machine 90 begins and performs its automated self-test routine.

Once the self-test is performed, it is contemplated for system 110c to perform the same steps 1 to seven discussed above, except that the action is now a disinfection procedure instead of the automated self-test routine. Here, the custom app downloaded to the patient's mobile communication device 200 may display a countdown timer to patient 12 reminding the patient how much time the patient has to return to machine 90 to begin treatment. It should be appreciated that different types of medical fluid delivery machines may have different one, two, three or more actions that patient 12 or clinician 112 may perform before treatment begins.

Regarding systems 110a to 110c, it is contemplated to program the app on mobile communication device 200 to be configurable by the user to select which type of notification that the user would like to receive on their device 200, e.g., via the app itself, via text message, and/or via calendar notification. System hub 120 may in one embodiment send all notification types, where mobile communication device 200 ignores the communication types that the user has disabled. System hub 120 in another embodiment stores the user's preferences and only sends information in selected notification types.

C. Clinician Device/Server Embodiments

Figure 7:
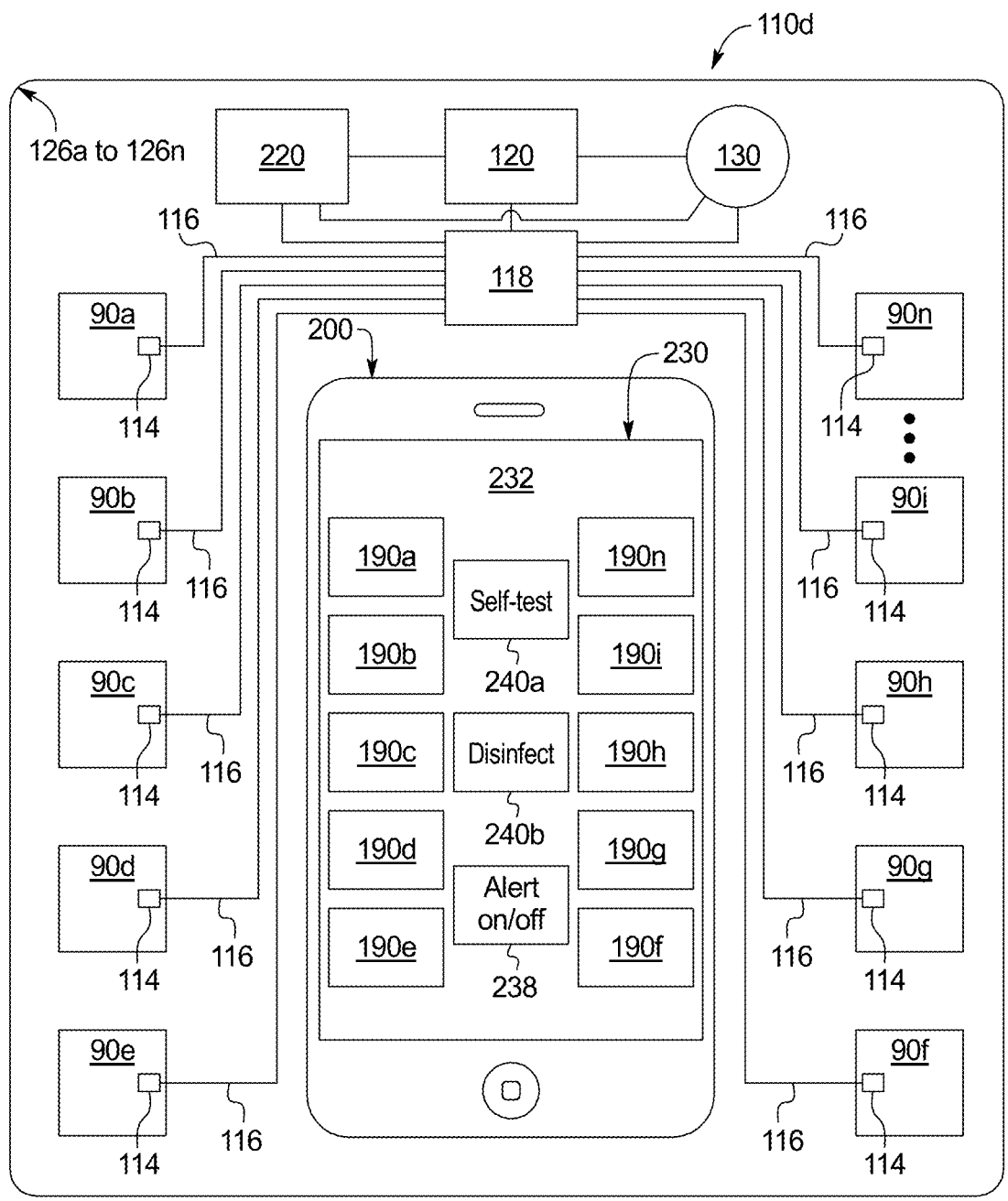
FIG. 7 is a schematic view of one embodiment of a hospital or clinical version of a medical fluid delivery device and data transfer system and method of the present disclosure having a mobile communication device application in a first state.
Figure 8:
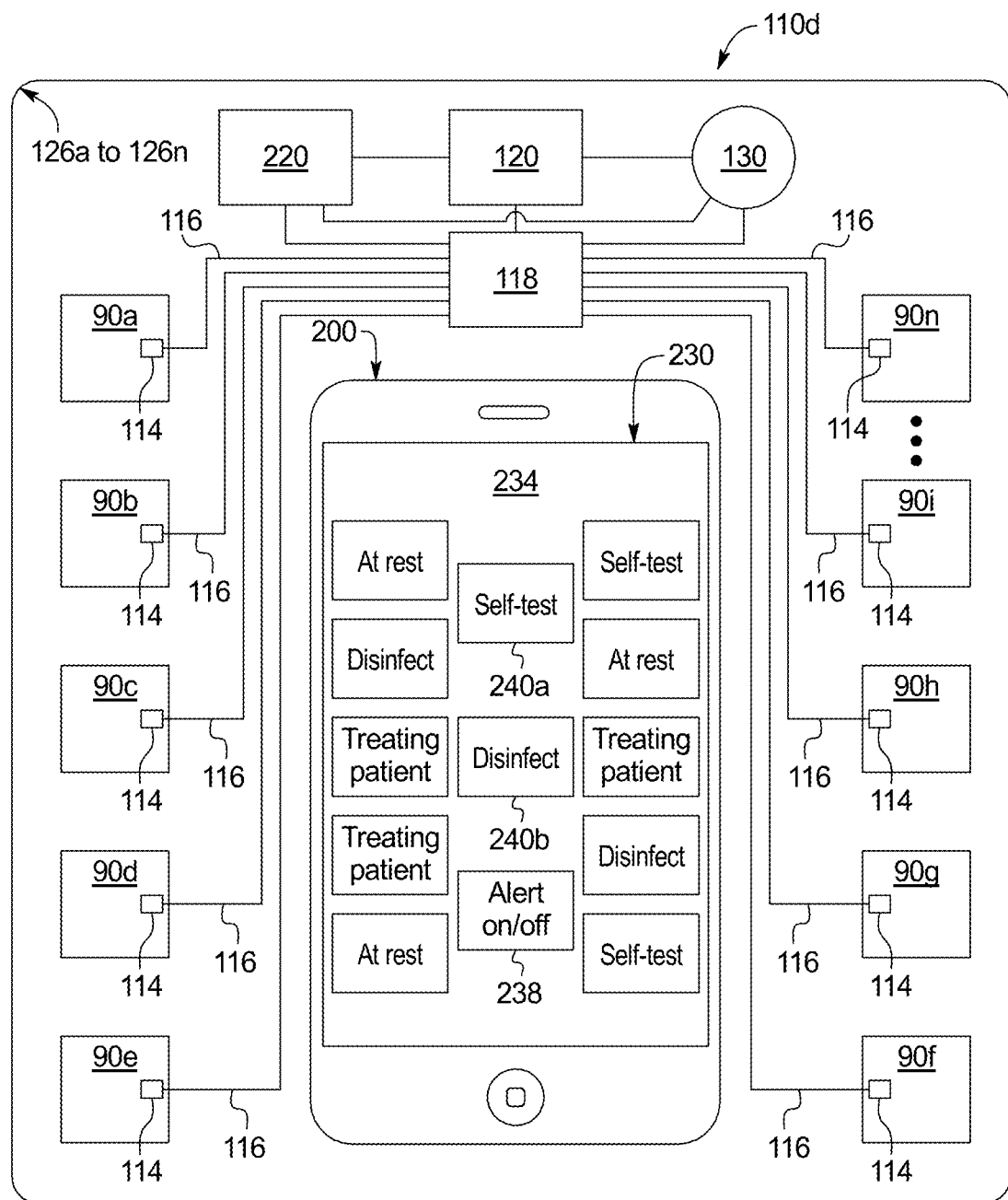
FIG. 8 is a schematic view of one embodiment of a hospital or clinical version of a medical fluid delivery device and data transfer system and method of the present disclosure having a mobile communication device application in a second state.
Figure 9:
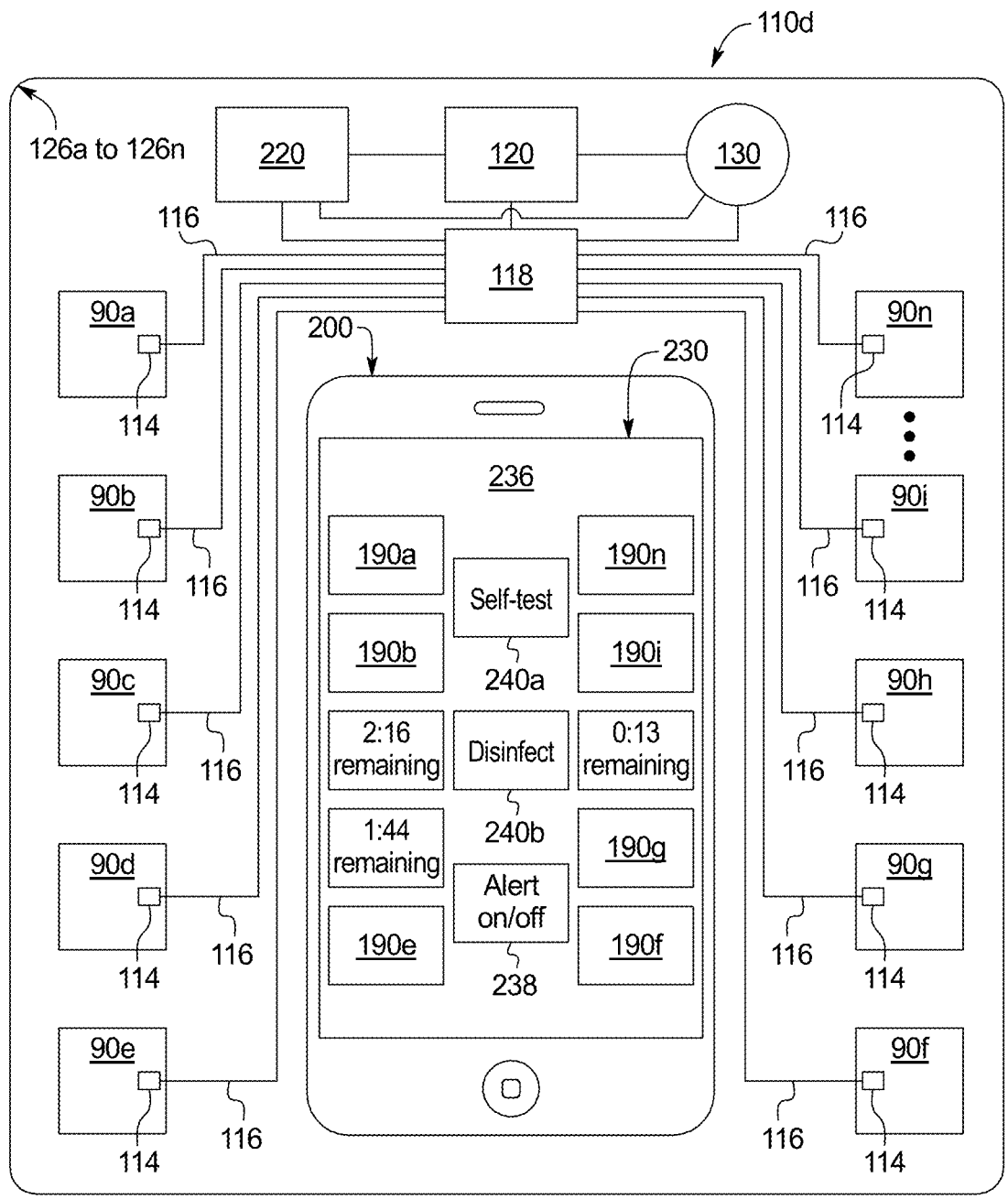
FIG. 9 is a schematic view of one embodiment of a hospital or clinical version of a medical fluid delivery device and data transfer system and method of the present disclosure having a mobile communication device application in a third state.

Referring now to FIGS. 7 to 9, one embodiment of a system 110d having a clinician-based downloadable software application ("app") 230 for a doctor's, clinician's or nurse's mobile communication device or server 200 is illustrated on screens 232 to 236. As discussed above, mobile communication device 200 may be that of a patient 12 or that of a doctor/nurse/clinician 112. Screens 232 to 236 of FIGS. 7 to 9 illustrate that app 230 may be used in a clinic or hospital 126a to 126n, where a nurse, for example, is responsible for multiple machines 90a to 90n. Machines 90a to 90n may again be hemodialysis machines, peritoneal dialysis machines, CRRT machines, drug and/or nutritional fluid delivery machines and combinations thereof.

Screen 232 illustrates that app 230 may monitor and, if desired, control multiple machines 90. In the illustrated embodiment, machines 90a to 90n are each represented by a dedicated icon 190a to 190n displayed on screen 232 of app 230. Icons 190a to 190n in the illustrated embodiment are ordered the same on screens 232 to 236 as machines 90a to 90n are ordered in clinic 126a to 126c to help orient doctor/nurse/clinician 112.

It is contemplated that app 230 operates with system hub 120 as has been discussed herein, where system hub 120 is remote from clinic or hospital 126a to 126n and is maintained for example by a manufacturer of one or more of machines 90a to 90n. App 230 may for example be developed initially at product development 128 illustrated in FIG. 1. App 230 may then be sent from product development 128 to system hub 120 via service portal 130 as illustrated in FIGS. 1 and 7. Any nurse, clinician or doctor 112 authorized to download app 230 may do so from system hub 120. Thereafter, system hub 120 maintains middleware software to operate with app 230 in the manners described above in systems 110a to 110c.

In an alternative embodiment, clinics 126a to 126n may maintain their own local area networks, each operating with a local system hub 220. App 230 may again be developed by product development 128 (FIG. 1) and delivered via service portal 130 to a local system hub 220 of a clinic 126a to 126n operating with overall system 10. Each nurse, clinician or doctor 112 authorized to download app 230 does so from local system hub 220. Thereafter, local system hub 220 maintains middleware software to operate with app 230 in the manners described above for system hub 120 in systems 110a to 110c. In a further alternative embodiment, app 230 may be developed by clinic 126a to 126n and stored on its local system hub 220.

Middleware software of system hub 120 or local system hub 220 updates the status of each machine 90a to 90n. Nurse, clinician or doctor 112 may select an icon 190a to 190n at any time to see the current status of each machine 90a to 90n, e.g., "at rest", "self-test, "disinfect", or "treating patient" as illustrated in screen 234 of FIG. 8. Other status markers are contemplated and may be different for different types of machines. Nurse, clinician or doctor 112 may then select any of "at rest", "self-test, "disinfect", or "treating patient" to return to the home icons 190a to 190n as illustrated in FIG. 9.

As discussed above, it is contemplated to turn connectivity agent 114 of each machine 90 off when the machine is running and in particular when a patient 12 is connected to the machine. It is also contemplated however to allow connectivity agent 114 of each machine 90a to 90n of clinics 126a to 126n to remain on until the end of disinfection, so that middleware software at system hub 120 or local system hub 220 may receive from each machine 90a to 90n a status change to "treating patient". In addition, because each machine 90a to 90n knows its scheduled treatment duration, the machines may also send to middleware software the scheduled duration, which then sends the duration in the form of a countdown timer along with the status change for "treating patient". Here then, when nurse, clinician or doctor 112 selects "treating patient" in FIG. 8, they are able to see a countdown timer showing the time of treatment remaining as illustrated in FIG. 9.

It is contemplated that for the countdown timers, connectivity agent 114 allows machines 90a to 90n to send time remaining data to system hub 120, so that app 230 may display the actual time remaining for each machine 90 undergoing a timed process. App 230 takes into account alarms or other delays that machines 90 may experience. During an alarm situation, the corresponding icon 190a to 190f may display a message such as "alarm" or "safe mode". Nurse, clinician or doctor 112 may then select the countdown time in FIG. 9 to return to the home icons 190c, 190d, and 190h illustrated in FIG. 7.

Nurse, clinician or doctor 112 may also toggle an alert on/off icon 238 to either allow or not allow status changes for machines 90a to 90n to be alerted visually, audibly and/or haptically. If alert on/off icon 238 is switched to "on", app 230 of mobile communication device 200 will provide a visual, audible and/or haptic alert each time a machine's status changes, e.g., (i) self-test started, (ii) self-test completed, (iii) disinfection started, (iv) disinfection completed, (v) treatment started, (vi) treatment completed. In an embodiment, codes for (i) to (v) are sent via machines 90a to 90n though secure managed connection 116, connectivity server 118 and system hub 120 or local system hub 220 to be translated by middleware software and forwarded to app 230, which updates the appropriate icon 190. In various embodiments, "(vi) treatment completed" may be (a) sent via machines 90a to 90n with connectivity agent 114 activated or (b) inferred when the countdown timer of the appropriate icon 190a to 190n expires, and where connectivity agent 114 may still be off.

If alert on/off icon 238 is switched to off, e.g., if nurse, clinician or doctor 112 does not want to be interrupted at a given moment, icons 190a to 190n are still updated as described above but audible and/or haptic alerts are not provided. Nurse, clinician or doctor 112 may still actively view the status of each machine 90a to 90n, however, by selecting the associated icon 190a to 190n.

Screens 232 to 236 illustrate action buttons 240a and 240b (referred to herein collectively to action buttons 240 or generally individually as action button 240). Any number of action buttons 240 may be provided for any type of pre-treatment action needed for any modality, e.g., hemodialysis, peritoneal dialysis, CRRT, drug and/or nutritional fluid delivery. In the illustrated embodiment, action buttons 240a is for starting a self-test for machines 90, while action button 240b is for starting a disinfection sequence for machines 90.

In one embodiment, when self-test button 240a is selected, any machine 90a to 90n capable at that time of performing a self-test has its corresponding icon 190a to 190n highlighted. Nurse, clinician or doctor 112 selects whichever icon(s) 190 for the machine(s) 90 that the nurse, clinician or doctor 112 wishes to perform a self-test. That selected icon(s) 190 may then turn into a "confirm" button, which the nurse, clinician or doctor 112 has to press again to cause the selected machine(s) 90 to perform its self-test. App 230 of mobile communication device 200 then sends a corresponding self-test code to middleware software at system hub 120 or local system hub 220, which converts, if needed, the self-test code into a self-test initiation command, which is sent via connectivity server 118 over secure managed connection 116 to the connectivity agent 114 of the selected machine 90, which transfers the command to the machine's ACPU 50, which in turn initiates the self-test.

In the illustrated embodiment, when disinfection button 240b is selected, any machine 90a to 90n capable at that time of performing disinfection has its corresponding icon 190a to 190n highlighted. Nurse, clinician or doctor 112 selects whichever icon(s) 190 for the machine(s) 90 that the nurse, clinician or doctor 112 wishes to perform disinfection. That selected icon(s) 190 may again turn into a "confirm" button, which the nurse, clinician or doctor 112 has to press again to cause the selected machine(s) 90 to perform its disinfection. App 230 of mobile communication device 200 then sends a corresponding disinfection code to middleware software at system hub 120 or local system hub 220, which converts, if needed, the disinfection code into a disinfection initiation command, which is sent via connectivity server 118 over secure managed connection 116 to the connectivity agent 114 of the selected machine 90, which transfers the command to the machine's ACPU 50, which in turn initiates disinfection.

The procedure just described for action buttons 240 may also be implemented in system 110c and be implemented for other machine commands, which may vary depending on the type of machine 90. It is also contemplated that a clinic 126a may decide that it is safe enough with one or more nurse, clinician or doctor 112 present at the clinic to leave connectivity agent 114 on during treatment or a portion of treatment. In such case, nurse, clinician or doctor 112 may control in-treatment activities for machines 90. For example, nurse, clinician or doctor 112 may receive and respond to alarms/alerts via app 230 at mobile connection device 200, start and stop pumps and other facets of treatment, start and stop disinfection, start and stop priming, and the like.

Each of systems 110a to 110d operates with some form of addressing. As discussed above, connectivity server 118 is provided in one embodiment to ensure that data is delivered in the proper form to the proper machine 90, and that data from a machine 90 is delivered in its proper form to the proper destination. In one embodiment, when a machine 90 sends data to system hub 120 or local system hub 220 for delivery to a mobile communication device 200, the data is provided with a machine identifier that identifies the machine 90 from which the data was sent. Connectivity server 118 knows each mobile communication device 200 to which a particular machine's data belongs and tells system hub 120 or local system hub 220 which communication devices 200 are to receive the data. System hub 120 or local system hub 220 may then convert the data as has been discussed herein. When sending the, e.g., converted, data, system hub 120 or local system hub 220 may strip the machine identifier from the data since it is not needed anymore. In system 110d, however, the machine identifier may be delivered along with the, e.g., converted, data so that app 230 knows which icon 190a to 190n to populate with the new data. Here, app 230 may strip the machine identifier once it is not needed anymore.

In one embodiment, when a mobile communication device 200 sends data to system hub 120 or local system hub 220 for delivery to a machine 90, the data is provided with a mobile communication device 200 identifier that identifies the mobile communication device 200 from which the data was sent. System hub 120 or local system hub 220 may or may not convert the data from mobile communication device 200 as discussed above, but in either case, the mobile communication device 200 identifier is maintained for connectivity server 118. Connectivity server 118 knows which machine 90 is to receive the, e.g., converted, data for each mobile communication device 200, and sends the, e.g., converted, data to each associated communication device

200. Connectivity server 118 may strip the mobile communication device 200 identifier from the data once delivered to machine 90 since it is no longer needed.

App 230 as described above allows nurse, clinician or doctor 112 to setup, monitor and perhaps control treatment at a medical fluid delivery machine 90. It is contemplated to provide similar functionality via an app to patient 12 or a caregiver for patient 12 at the patient's home (dashed box in FIG. 1). Connectivity may be the same as shown in FIGS. 7 to 9. However, the setting is not a clinic 126a to 126n, but is instead the home or other non-clinical location such as a business or vacation location. In addition, there is typically only a single machine 90, not multiple machines 90a to 90n. It is possible however that a single patient 12 may be treated via multiple machines 90, which could each be supported by the app as described herein. If patient 12 is at home but away from machine 90, the app may provide valuable information, such as amount of time left for starting or completing a start-up procedure task, a disinfection procedure or a self-test routine. When the patient is being treated by machine 90, he/she can see information on its user interface 122, which may itself be a tablet as illustrated in FIG. 1. But there may also be a caregiver that helps patient 12 at home during treatment, such as a spouse, friend, or in-home nurse. The caregiver benefits from the home app by receiving status updates, start-up procedure time remaining, disinfection time remaining, priming time remaining, treatment time remaining, information regarding whether or not patient 12 is connected to machine 90, alerts, alarms, and the like. The app in one embodiment requires a login and password associated with the patient to be entered before it can be downloaded to the caregiver's mobile communication device 200, so that only authorized people can view patient treatment data or information.

II. PATIENT ENGAGEMENT EMBODIMENTS

Figure 10:
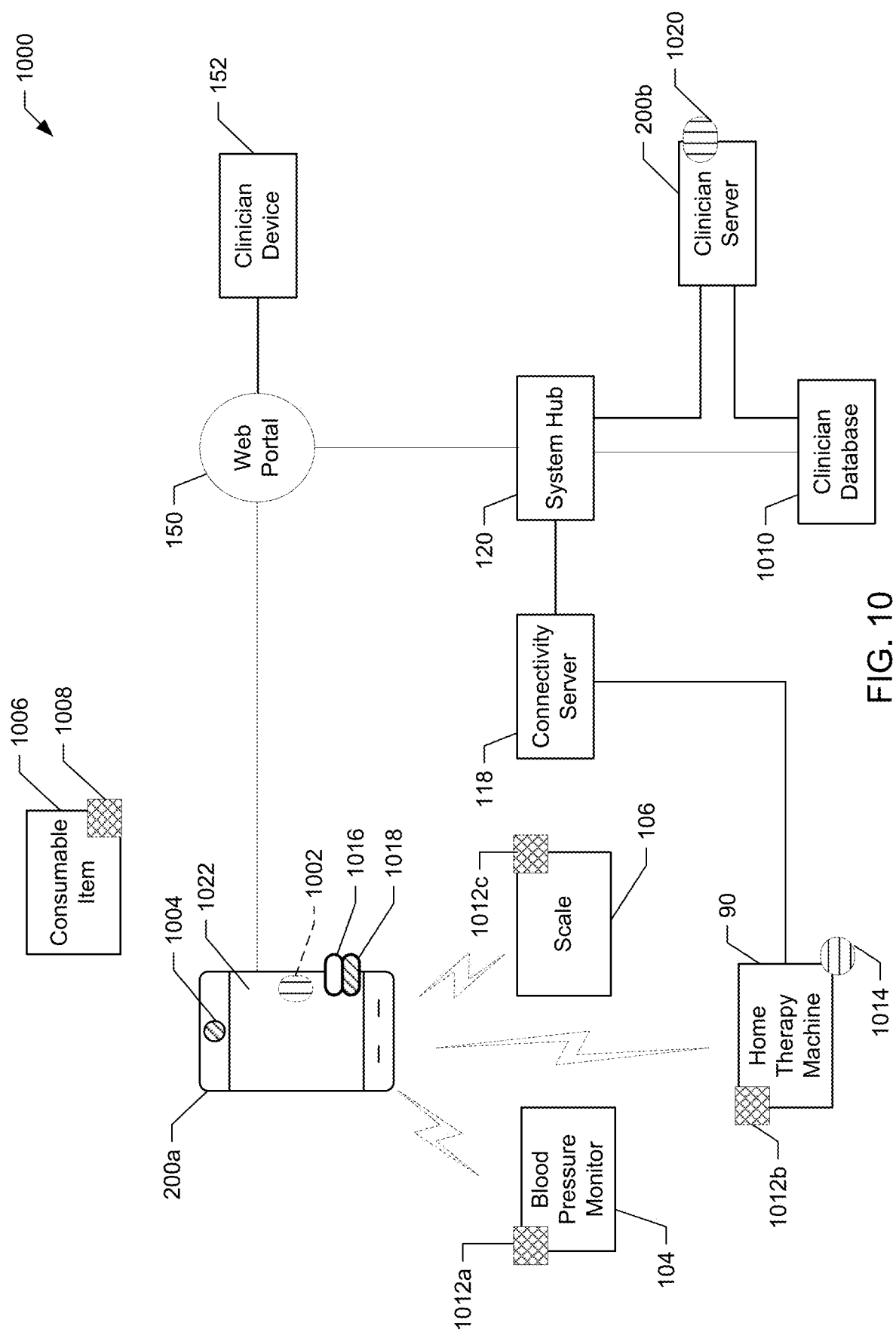
FIG. 10 shows a second embodiment of a medical fluid data transfer system.

The example medical fluid data transfer system 10 disclosed above in connection with FIGS. 1 to 9 is configured to improve a patient's engagement with a medical fluid delivery treatment, such as a dialysis treatment, a renal failure treatment, and/or a peritoneal treatment. FIG. 10 shows an example medical fluid data transfer system 1000 that is similar to the medical fluid data transfer system 10 discussed in connection with FIGS. 1 to 9, accordingly to an example embodiment of the present disclosure. The example medical fluid data transfer system 1000 (e.g., a mobile platform) is configured to improve a patient's engagement and/or compliance with a treatment by increasing treatment transparency, providing a patient features to control and report information related to the treatment, and/or providing access to educational material and/or real-time assistance from a clinician.

The example medical fluid data transfer system 1000 includes, for example, a personal mobile communication device 200a that is operated by a patient. The medical fluid data transfer system 1000 also includes a blood pressure monitor 104, a scale 106, and a home therapy machine 90, which are similar to the respective devices discussed above in connection with FIGS. 1 to 9. The personal mobile communication device 200a, the home therapy machine 90, the blood pressure monitor 104, and the scale 106 may be located, for example, at a patient's home, a self-service clinic, and/or a serviced medical clinic.

The home therapy machine 90 may include any type of hemodialysis machine, peritoneal dialysis machine, CRRT machine, drug and/or nutritional fluid delivery machine, and combinations thereof. The home therapy machine 90 may provide, for example continuous cycling peritoneal dialysis ("CCPD"), tidal flow automated peritoneal dialysis ("APD"), and continuous flow peritoneal dialysis ("CFPD"). The home therapy machine 90 may perform drain, fill, and dwell cycles automatically, typically while a patient sleeps.

Peritoneal dialysis dialysate may include a solution or mixture that includes between 0.5% and 10% dextrose (or more generally glucose), preferably between 1.5% and 4.25%. Peritoneal dialysis dialysate may include, for example, Dianeal®, Physioneal®, Nutrineal®, and Extraneal® dialysates marketed by the assignee of the present disclosure. The dialysate may additionally or alternatively include a percentage of icodextrin.

In both hemodialysis and peritoneal dialysis, "sorbent" technology can be used to remove uremic toxins from waste dialysate, re-inject therapeutic agents (such as ions and/or glucose) into the treated fluid, and reuse that fluid to continue the dialysis of the patient. One commonly used sorbent is made from zirconium phosphate, which is used to remove ammonia generated from the hydrolysis of urea. Typically, a large quantity of sorbent is necessary to remove the ammonia generated during dialysis treatments.

The example weight scale 106 includes any device configured to measure a mass of a patient or treatment component. For example, the weight scale 106 may measure a patient weight before, during, and/or after a renal failure therapy treatment. Additionally or alternatively, the weight scale 106 may measure a supply or drain bag for tracking a renal failure therapy. Specifically, weight scale 106 may be used to measure an amount of UF removed or an amount of fluid provided to a patient. The weight scale 106 may display a digital value indicative of weight. Alternatively, the weight scale 106 may display a physical scale or dial that aligns with a marker to indicate a measured weight. In some embodiments, the weight scale 106 may store weight values before, during, and/or after treatment in separate windows such that patient input is required to view all the values when medical information is recorded.

The example blood pressure monitor 104 includes any device configured to measure a blood pressure and/or pulse of a patient. For example, the blood pressure monitor 104 may measure a patient blood pressure before, during, and/or after a renal failure therapy treatment. The blood pressure monitor 104 may display a digital value indicative of a patient's blood pressure. Alternatively, blood pressure monitor 104 may display a physical scale with a dial that aligns with a numerical value to indicate a measured blood pressure. In some embodiments, the blood pressure monitor 104 may store blood pressure values before, during, and/or after treatment in separate windows such that patient input is required to view all the values when medical information is recorded. The blood pressure monitor 104 may be integrated with the home therapy machine 90. In another embodiment, the blood pressure monitor 104 may include a wearable sensor, such as a smartwatch or fitness-tracking device.

In addition to obtaining medical information (e.g., medical device data) from the medical devices 90, 104, and 106, example personal mobile communication device 200a may also obtain medical information from a patient and/or therapy consumable item 1006. FIG. 10 shows an example of a consumable item 1006, which includes, for example, a renal failure therapy medical device filter, a disposable cassette, a blood line set, a drug delivery line set, and a container (e.g., a dialysis solution concentrate container, a blood anticoagulant container, a medication container, and/or a water purification container). The consumable item

1006 may also include a sorbent cartridge or any other disposable or material supply for a medical treatment. The consumable item may include an identifier 1008, which is configured to provide medical information in the form of consumable information or consumable data. For example, the identifier 1008 may include information identifying a type of consumable item, a serial number, and/or properties of the consumable item. In some instances, the consumable item 1006 may also include a label containing medical information such as chemical composition properties. A patient or clinician uses the personal mobile communication device 200*a* to record images of the identifier 1008, images of labels on the consumable items 1006, and/or images of the consumable item 1006 itself to document materials used during a treatment.

The personal mobile communication device 200*a* may be communicatively coupled to the home therapy machine 90, the blood pressure monitor 104, and/or the scale 106 via a wired connection (e.g., a USB connection) or a wireless connection (e.g., Bluetooth™, WiFi™ Zigbee®, Z-Wave®, wireless USB, or a wireless local area network ("WLAN")). In other examples, the personal mobile communication device 200*a* is not communicatively coupled to any one of the home therapy machine 90, the blood pressure monitor 104, and/or the scale 106. In these other examples, a patient may manually enter data displayed by the home therapy machine 90, the blood pressure monitor 104, and/or the scale 106 into the personal mobile communication device 200*a*. Additionally or alternatively, in these other examples, a patient may record one or more images of data displayed by (or an identifier placed on) the home therapy machine 90, the blood pressure monitor 104, and/or the scale 106 using a camera 1004 of the personal mobile communication device 200*a*.

Collectively, the blood pressure monitor 104, and the scale 106 are referred to as medical devices. It should be appreciated that the medical fluid data transfer system 1000 may include additional medical devices such as an infusion pump (e.g., a syringe pump, a linear peristaltic pump, a large volume pump ("LVP"), an ambulatory pump, multi-channel pump), an oxygen sensor, a respiratory monitor, a glucose meter, a blood pressure monitor, an electrocardiogram ("ECG") monitor, a weight scale, and/or a heart rate monitor. In other examples, the medical fluid data transfer system 1000 may include fewer medical devices and/or medical devices integrated together (e.g., a blood pressure monitor 104 integrated with the home therapy machine 90).

In some embodiments, the personal mobile communication device 200*a* is configured to record, display, and/or populate a patient medical record with medical information or data. As disclosed herein, medical information or data includes medical device data and patient data, which may refer to data or information created by, generated by, or otherwise related to medical devices, patients, and/or consumable items used by medical devices. For instance, the medical information includes prescription or programming information used by a medical device to administer a treatment. Medical information also includes sensed data such as fluid pressure, flowrate, conductivity, concentration, temperature and patient data. As provided herein, patient data (e.g., vital sign data) includes sensed patient physiological information such as patient blood pressure, weight, heart rate, etc. The medical information may also include subjective information, such as information regarding how a patient is feeling (e.g., tired, fatigued, happy, excited, etc.). The medical information may be displayable on a screen of a medical device, provided by a physical dial or display of a medical device, or printed on a label attached or a medical device. Accordingly, medical device data or medical information includes a medical device setting, a medical device reading, and/or a patient reading.

Medical information also refers to information contained on an identifier attached to a patient or treatment consumable item. Specifically, the medical information may include information conveyed by an identifier of a patient provided on a patient wristband for identifying a patient. Medical information also includes information regarding a consumable item, which may identify a consumable item type, a consumable item model, and/or properties of a consumable item, such as a level of dextrose in a supply bag of renal failure therapy solution.

Treatment data or treatment information refers to data generated and/or transmitted by the home therapy machine 90 of FIGS. 1 to 10. Treatment information may include a volume of fluid infused, an amount of ultrafiltration UF removed from a patient, and/or a treatment time. The treatment information may also include alarms, alerts, and/or diagnostic information generated by the home therapy machine 90. Generally, the treatment information is transmitted from a home therapy machine 90 to a clinician server 200*b*. In some embodiments, the treatment information may be recorded in a personal mobile communication device 200*a*. In these embodiments, the treatment information may be referred to as and/or be included/processed as medical information.

As shown in FIG. 10, some of all of the medical devices 90, 104, and 106 may include an identifier 1012 configured to store a unique identification number. Identifier 1012 may code, for example, an assigned device number, a serial number, a hardware number, a model number, and/or a device type of the respective medical devices 90, 104, and 106. For example, identifier 1012*b* of the home therapy machine 90 may store an assigned device number. The personal mobile communication device 200*a* reads identifier 1012*b* to determine, for example, a medical device type for subsequent analysis and identification of medical information in images recorded from a screen of the machine 90. In some embodiments, the identifier 1012 may more generally indicate a model or type of a medical device. For example, identifier 1012*c* may indicate that device 106 is a weight scale and/or indicate a model number of a weight scale.

The identifier 1012 may include machine readable markings such as, for example, a barcode or a quick-response ("QR") code. The identifier 1012 may also include human-readable text, such as a serial number, asset number, or hardware number. In some embodiments, identifier 1012 may be printed to an article physically attached to a housing of the respective medical devices 90, 104, and 106, such as identifier 1012*b* shown for the home therapy machine 90. Additionally or alternatively, the identifier 1012 may be displayed on a screen of some of all of the medical devices 90, 104, and 106. For example, a clinician may select a control interface to cause the home therapy machine 90 to display a window with the identifier 1012*b* on a screen. In yet other embodiments, the identifier 1012 may be included within a radio frequency ("RF") microchip, such as an RFID chip or NFC chip.

The example medical devices 90, 104, and 106 may also include one or more control interface for providing control instructions. For example, the home therapy machine 90 includes a control interface 1014. Control interfaces may include buttons, a control panel, or a touchscreen. A control interface may be configured to enable a user to navigate to a certain window or user interface on a screen of the respective medical devices 90, 104, and 106. Control interfaces may also provide instructions for operating or controlling the respective medical devices 90, 104, and 106.

As illustrated in FIG. 10, the example fluid data transfer system 1000 includes a web portal 150, a system hub 120, and a clinician server 200b (similar to the respective devices discussed in connection with FIGS. 1 to 9) to communicate with the personal mobile communication device 200a. The web portal 150, system hub 120, and/or the clinician server 200b transmit medical information from a patient's medical record (stored in a clinician database 1010) to the personal mobile communication device 200a. In addition, the web portal 150, system hub 120, and/or the clinician server 200b may provide the personal mobile communication device 200a access to educational material or a real-time help session with a clinician. The example web portal 150, system hub 120, and/or the clinician server 200b is also configured to enable the personal mobile communication device 200a to provide medical information for populating a patient's medical record.

The example fluid data transfer system 1000 of FIG. 10 also includes a connectivity server 118, which is communicatively coupled to the home therapy machine 90. As discussed above in connection with FIGS. 1 to 9, the connectivity server 118 provides bidirectional communication between the home therapy machine 90 and the clinician server 200b and/or the clinician database 1010. The home therapy machine 90 may connect to the connectivity server 118 via the Internet.

In the illustrated example of FIG. 10, the example personal mobile communication device 200a includes a processor 1016 in communication with a memory 1018 storing instructions. At least some of the instructions define or specify an application 1002, that, when executed by the processor 1016, cause the processor 1016 to provide features that improve a patient's engagement and/or compliance with a treatment. The processor 1016 may comprise digital and analog circuitry structured as a microprocessor, application specific integrated circuit ("ASIC"), controller, etc. The memory 1018 includes a volatile or non-volatile storage medium. Further, the memory 1018 may include any solid state or disk storage medium.

As discussed in more detail below, the features of the application 1002 include displays of treatment progress information, control of which treatment programs are run by the home therapy machine 90, recording of medical information, displays of educational material, and/or initiating a help session with a clinician. The application 1002 may be feature-rich or feature-lite. A feature-rich application is configured for a smartphone and utilizes native graphics, touchscreen, and processing power of the personal mobile communication device 200a. A feature-lite application is configured to operate on a cellular phone that has relatively less sophisticated graphics and reduced processing power. The cellular phone may also not include a touchscreen or instead have a touchscreen with limited capability.

In some embodiments, the personal mobile communication device 200a may not include the application 1002. Instead, the personal mobile communication device 200a may use native or other installed applications to communicate with the clinician server 200b. For example, the personal mobile communication device 200a may use text, SMS, or an email program to communicate with the clinician server 1020.

The example clinician server 200b includes an application 1020, such as the application 230 described in connection with FIGS. 1 to 9. The application 1020 is configured to communicate with the personal mobile communication device 200a to provide improved patient engagement and/or compliance. In some embodiments, the example application 1020 is configured to facilitate the storage of medical information (recorded by the personal mobile communication device 200a) to one or more patient records in the database 1010. The application 1020 also may include one or more interfaces or application programming interface ("API") to provide treatment progress data and/or medical information to the application 1002 for display on a display interface 1022 (e.g., a touchscreen) on the personal mobile communication device 200a. The application 1020 at the clinician server 200b may also provide educational material upon request from the application 1002 and/or facilitate a communication session between the personal mobile communication device 200a and a clinician's device 152.

In some instances, the application 1002 on the personal mobile communication device 200a and/or the application 1020 on the clinician server 200b is configured to convert or otherwise provide medical information to the clinician database 1010 of other devices in the medical fluid data transfer system 1000 that conforms to a Health-Level-7 ("HL7") standard (e.g., a medical standard). This conversion enables medical information to be stored in an HL7 format regardless of a format when entered at the personal mobile communication device 200a. The application 1002 and/or the application 1020 may operate as a network conduit to seamlessly propagate relevant medical information from a medical device to a patient medical record when gaps in network or device connectivity exist.

Figure 11:
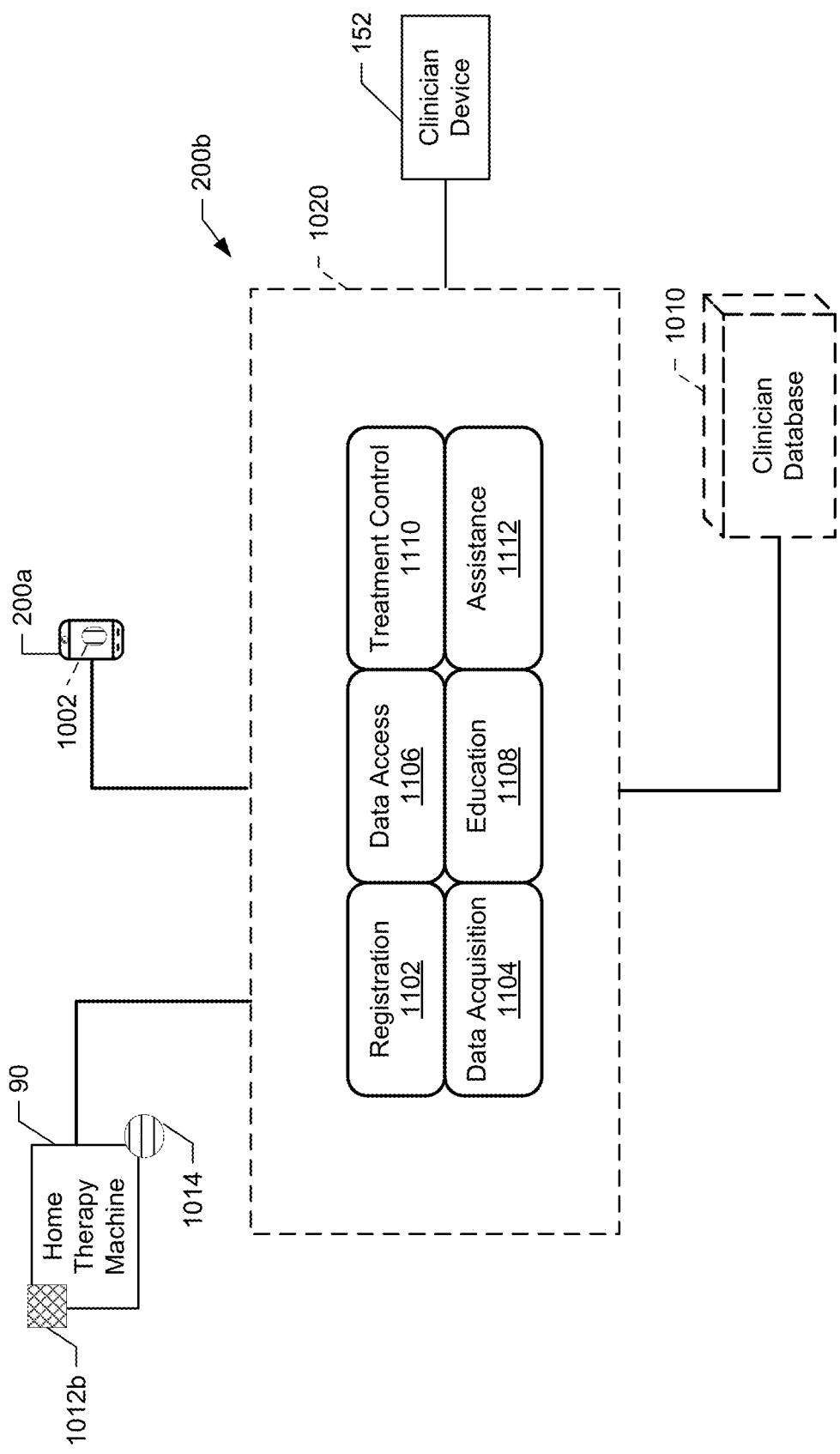
FIG. 11 shows a diagram illustrative of operational modules of an application at a clinician server of the medical fluid data transfer system of FIG. 10, according to an embodiment of the present disclosure.

FIG. 11 shows a diagram illustrative of operational modules of the application 1020 at the clinician server 200b of FIG. 10, according to an embodiment of the present disclosure. The application 1020 may include a registration module 1102 configured to register a home therapy machine 90 and/or a personal mobile communication device 200a with a particular patient and/or patient medical records stored in the clinician database 1010. As described in more detail in connection with FIG. 12, registration may include determining a type of the personal mobile communication device 200a for the formatting of subsequent communications.

The application 1020 may also include a data acquisition module 1104 configured to receive treatment and/or medical information from the registered home therapy machine 90 and/or personal mobile communication device 200a. In addition, the application 1020 may include a data access module 1106 to transmit or otherwise provide access to medical information stored in one or more patient records associated with a patient. The application 1020 may further include an education module 1108 configured to provide access to educational material or help-documentation for a patient regarding their treatment and/or operation of the home therapy machine 90. Moreover, the application 1020 may include a treatment control module 1110 that enables a patient (or clinician) to change (or modify) a treatment program performed by the home therapy machine 90. The application 1020 may additionally include an assistance module 1112 that creates a real-time communication session between the personal mobile communication device 200a and a clinician device 152.

Each of the example modules 1102 to 1112 are configured to improve a patient's engagement with a medical fluid delivery treatment, thereby increasing a patient's compliance with a prescribed treatment. It should be appreciated that while modules 1102 to 1112 are shown, the example application 1020 may include fewer or additional modules. For instance, in some embodiments, the education module 1108 and the assistance module 1112 may be omitted. The sections below provide further description regarding each of the modules 1102 to 1112.

As discussed below, each of the modules 1102 to 1112 are configured to communicate with personal mobile communication device(s) 200a and/or clinician device(s) 152. In some embodiments, communications from personal mobile communication device(s) 200a may be addressed generally to the clinician server 200b, web portal 150, connectivity server 118, and/or system hub 120. The messages may be routed internally to the different modules 1102 to 1112 based on content and/or identifiers. For example, the application 1002 may provide an identifier in a header to specify which of the modules 1102 to 1112 is to receive the message. For text-based messages, a router at the clinician server 200b may determine a destination module 1102 to 1112 based on message content or previous messages. For example, the router may determine that a received message corresponds to a message previously transmitted by the data acquisition module 1104. Based on this correspondence, the router sends the received message for processing via the data acquisition module 1104.

A. Registration Module Embodiment

The example registration module 1102 is configured to register the personal mobile communication device 200a and/or the home therapy machine 90 with the clinician server 200b and/or with a patient's medical records stored in the database 1010. The example registration module 1102 is configured to provide different types of registration, which is used by the data access module 1106 to determine how information is to be displayed to a patient based on which types of devices are registered. In addition, the data acquisition module 1104 determines how treatment and/or medical information is to be acquired based on registration information.

The registration module 1102 is configured to store registration information to a registration file stored in the clinician database 1010. The registration file may specify, for each patient or patient activation code ("PAC"), information indicative of a registered a personal mobile communication device 200a, information indicative of a registered home therapy machine 90, and/or an indication as to whether the application 1002 is installed on the personal mobile communication device 200a. In some embodiments, the registration file (or information from the registration file) may be included within a patient's medical record.

In some embodiments, there are different registration scenarios. For example, a patient may register a personal mobile communication device 200a by downloading application 1002 while also registering a home therapy machine 90. In this scenario, the registration module 1102 records that the patient installed the application 1002 on the personal mobile communication device 200a and (separately or through the application 1002) registered the home therapy machine 90. Based on this registration, the data acquisition module 1104 determines that the application 1002 installed on the registered personal mobile communication device 200a is to guide or otherwise prompt the patient for acquiring medical information. In addition, the data acquisition module 1104 determines that treatment information is to be received from the home therapy machine 90 rather than via the personal mobile communication device 200a. Accordingly, the data acquisition module 1104 may send a message to the application 1002 disabling a user interface for acquiring treatment information from the home therapy machine 90 (but still enabling a user interface for a manual exchange if one is prescribed for the patient). If a home therapy machine 90 is not registered, the data acquisition module 1104 causes the application 1002 to display a user interface to acquire treatment information from the home therapy machine 90 in the application 1002. Through registration, the data access module 1106 determines that information is to be displayed through the application 1002 and accordingly uses APIs and/or other data read components that are compatible or configured for the application 1002.

If a patient registers without downloading and/or installing the application 1002, the data acquisition module 1104 determines that data acquisition is to be prompted or guided. For example, the data acquisition module 1104 may transmit text messages and/or emails to the registered personal mobile communication device 200a prompting a patient for certain medical information and/or treatment information (if a home therapy machine 90 has not been registered). Information in the messages specifies which data is needed from the patient. While this remote guidance may be used for feature-lite personal mobile communication devices 200a, it may also be used for smartphones where a patient does not wish to download or install the application 1002 on a feature-rich device.

The data access module 1106 may also be configured to display information from a patient's medical record differently if the application 1002 is not installed. For example, instead of sending data that plugs into a well-defined feature-rich user interface, the data access module 1106 may render data in pictures that are transmitted via text to the personal mobile communication device 200a for viewing. Additionally or alternatively, the data access module 1106 may transmit the stored medical record information as text to the personal mobile communication device 200a. Thus, even without the application 1002 installed, the application 1020 at the clinician server 200b is configured to provide a patient access to data using native applications on the personal mobile communication device 200a.

Figure 12:
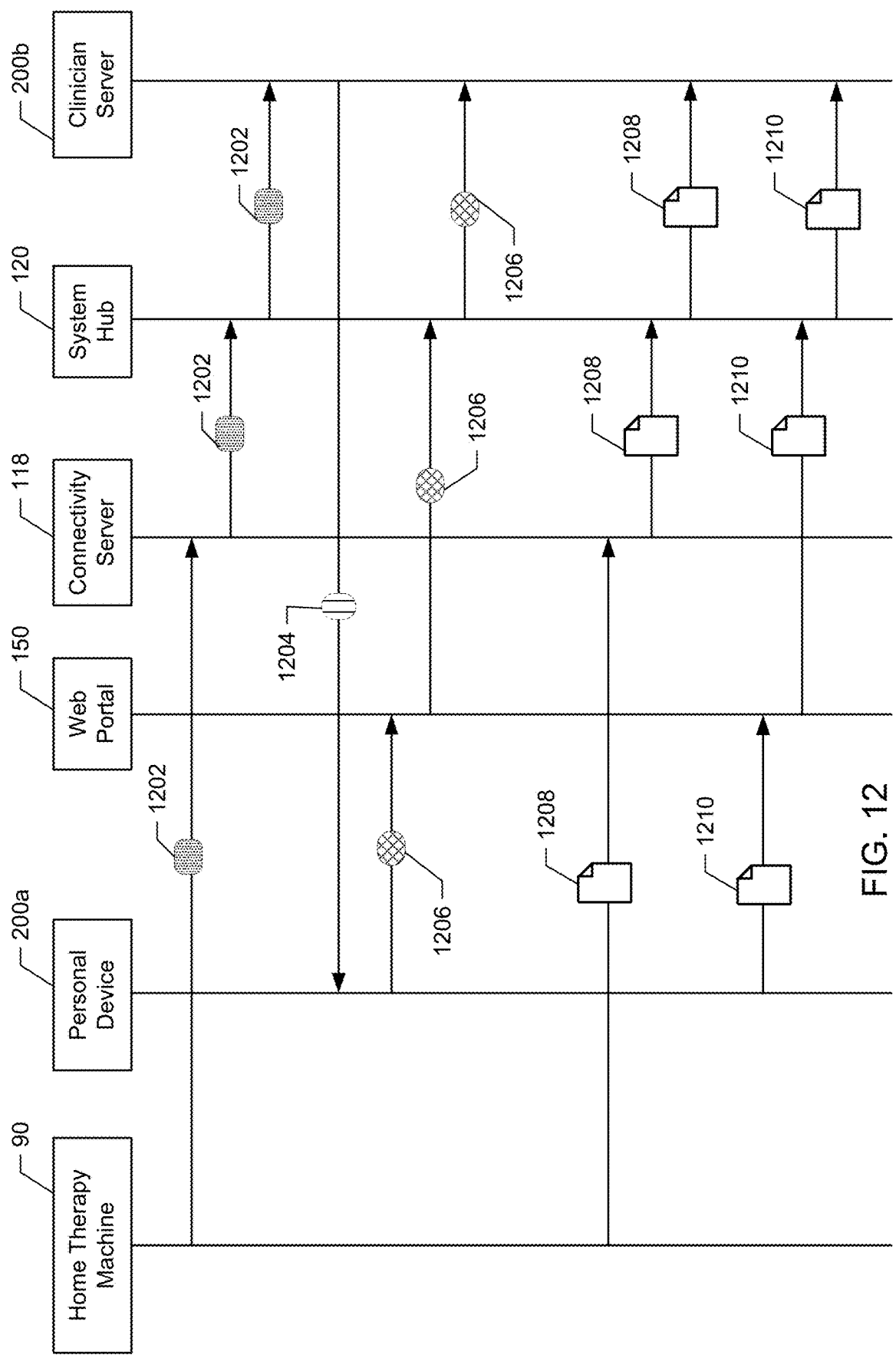
FIG. 12 shows a diagram illustrative of communications between a home therapy machine, a personal mobile communication device, and the clinician server of FIGS. 10 and 11, according to an example embodiment of the present disclosure.

FIG. 12 shows a diagram illustrative of communications between the home therapy machine 90, the personal mobile communication device 200a, and the clinician server 200b of FIGS. 10 and 11, according to an example embodiment of the present disclosure. Initially, the home therapy machine 90 registers with the clinician server 200b via the registration module 1102 of FIG. 11. Otherwise, the clinician server 200b will not have information as to which patient record data from the home therapy machine 90 is to be stored. In some embodiments, the home therapy machine 90 is pre-programmed with destination address information for the connectivity server 118, the system hub 120, and/or the clinician server 200b. The destination address may include an internet protocol ("IP") address and/or a Hypertext Transfer (or Transport) Protocol ("HTTP") address.

During setup, a patient (or clinician) enters a patient activation code ("PAC") into the home therapy machine 90. The PAC is originally generated and stored at the clinician server 200b and is provided to the patient when the patient receives the home therapy machine 90. The PAC may include a patient identifier or other code that is unique to the patient. The registration module 1102 at the clinician server 200b stores the generated PAC to one or more patient records and/or registration file associated with the patient. After entering the PAC, the home therapy machine 90 generates and transmits a message 1202 that includes the PAC. The message may also include a hardware identifier of the home therapy machine 90 and/or an IP address assigned to the home therapy machine 90. The home therapy machine 90 transmits the message 1202 to the preprogrammed address, in this case, the connectivity server 118. The example connectivity server 118 relays the message 1202 to the system hub 120, which routes the message to the clinician server 200b. The registration module 1102 at the clinician server 200b registers the home therapy machine 90 with the patient using the PAC. Registration includes, for example, associating an identifier of the home therapy machine 90 with patient medical records of the patient. Registration may also include the clinician server 200b storing the IP address of the home therapy machine 90 to enable messages to be transmitted to the home therapy machine 90. After registration, the data acquisition module 1104 of the clinician server 200b stores treatment information received from the home therapy machine 90 to one or more medical records associated with the patient.

The example personal mobile communication device 200a is also configured to register with the clinician server 200b via the registration module 1102. To register, the personal mobile communication device 200a may download or otherwise receive application 1002 via one or more message 1204 from the clinician server 200b (or a third-party application store). In an embodiment, during registration of the home therapy machine 90, the patient (or clinician) may provide a phone number of the personal mobile communication device 200a. The registration module 1102 uses the phone number to transmit the message 1204 as a text message. The message may include a hyperlink to a location (e.g., the database 1010 or a third-party website) that provides the application 1002 for download to the personal mobile communication device 200a. In other instances, the message 1204 may include an attached file, that when executed, installs the application 1002 on the personal mobile communication device 200a. Instead of providing a phone number, the patient may instead provide an email address during registration of the home therapy machine 90. Accordingly, the message 1204 includes an email message with a file or hyperlink for installing the application 1002 on the personal mobile communication device 200a.

In another embodiment, the message 1204 may enable a patient to register two different ways depending on a capability of their personal mobile communication device 200a and/or personal preference. The message 1204 includes text prompting a patient to respond to the text if they desire to register their personal mobile communication device 200a as a feature-lite device. A reply to the message 1204 is provided via text message 1206, which is routed to the registration module 1102. In turn, the registration module 1102 registers the personal mobile communication device 200a with an indication the application 1002 is not installed. In some instances, the message 1204 may also include text or a hyperlink prompting the patient to select the hyperlink or otherwise obtain the application 1002 if desired. The message 1204 may also provide a prompt or an option to select a device type, such as an Apple® device or an Android® device. During the registration process, the registration module 1102 registers the personal mobile communication device 200a based on information provided by a patient and/or read from the personal mobile communication device 200a.

The patient may register the personal mobile communication device 200a after the application 1002 is installed. In an embodiment, to register, the patient completes a registration form or fields provided by the application 1002. The form or fields are configured to accept the patient's PAC. The form or fields may also include prompts for a patient's name, email address, home address, phone number, etc. Information from the form or fields are sent in one or more message 1206 to the web portal 150, which transmits the message 1206 to the system hub 120 for routing to the clinician server 200b. The message 1206 may also include device type information of the personal mobile communication device 200a (as determined by the application 1002).

In some instances, the application 1002 may be configured with a destination address of the web portal 150, which is used for transmitting the messages. In other instances, the messages 1206 may be provided to an API at the web portal 150 for registering the application 1002 at the clinician server 200b. In yet other instances, the application 1002 transmits the message 1206 as one or more text messages or email messages to the web portal 150 (where the web portal 150 is assigned a telephone number, IP address, email address, or other address). The example registration module 1102 uses the PAC within the message 1206 to register the personal mobile communication device 200a with the medical records and/or registration file stored in the database 1010. At this point, both the home therapy machine 90 and the personal mobile communication device 200a are registered to the same patient at the clinician server 200b.

As mentioned above, in some embodiments, the personal mobile communication device 200a may not include an application. In these embodiments, the personal mobile communication device 200a may communicate with the clinician server 200b via text messages or through a web browser. Accordingly, the registration module 1102 of the clinician server 200b may transmit, to the personal mobile communication device 200a, a text message with a hyperlink to a database or webpage for completing a registration. Alternatively, the text message may include a prompt for a patient to respond with their PAC. Providing the PAC via either of these registration processes enables the registration module 1102 to associate the personal mobile communication device 200a (e.g., a phone number, hardware address, or IP address) with the appropriate patient medical records and/or registration file.

B. Data Acquisition Module Embodiment

FIG. 12 also illustrates data communication between the home therapy machine 90, the personal mobile communication device 200a, and the clinician server 200b. During operation, the home therapy machine 90 generates treatment information and status information (e.g., medical information). As discussed above in connection with FIGS. 1 to 9, the treatment information includes a volume of fluid infused, an amount of ultrafiltration ("UF") removed from a patient, and/or a treatment time. The status information includes alarms, alerts, or diagnostic information. Before or after a treatment, the home therapy machine 90 generates one or more message 1208 with the medical information, which is transmitted to the connectivity server 118. In turn, the connectivity server 118 routes the message 1208 to the system hub 120, which routes the message 1208 to the data acquisition module 1104 of the clinician server 200b. After receipt, the data acquisition module 1104 stores the medical information to a designated section of a patient's medical record (e.g., patient medical record 1302 of FIG. 13). The message 1208 may include an identifier or address of the home therapy machine 90, which is used by the data acquisition module 1104 to locate the appropriate medical record in the database 1010.

The example home therapy machine 90 may be configured to code, label, or otherwise identify, using metadata or other data identification technique, the medical information being transmitted. The coding or labeling enables the data acquisition module 1104 (or interfaces at the server 200b) to determine a context of the medical information for writing the medical information to the appropriate fields of a patient record. Additionally or alternatively, the coding or labeling may also be stored to the record, which is later used for searching and displaying the medical information.

FIG. 12 also illustrates that the personal mobile communication device 200a transmits medical information or medical information to the clinician server 200b. As described in more detail below, the personal mobile communication device 200a is configured to acquire medical information from medical devices, including devices 90, 104, and 106. Acquiring medical information may include receiving information manually entered by a patient, via a wired or wireless connection, and/or processing images recorded by camera 1004 of the personal mobile communication device 200a. The acquired medical information is packaged into one or more message 1210 and transmitted by the personal mobile communication device 200a to the web portal 150. The message 1210 may be a text message, an email message, or a web-based message (e.g., a HTTP message, an Extensible Markup Language ("XML") message, a JavaScript Object Notation ("JSON") payload, etc.). In some embodiments, the personal mobile communication device 200a may format the acquired medical information into one more data fields prior to transmission. Generally, the medical information acquired in the personal mobile communication device 200a is less structured than the medical information generated by the home therapy machine 90. Accordingly, the personal mobile communication device 200a and/or the data acquisition module of the clinician server 200b performs at least some processing of the medical information to provide an appropriate context or structure for inclusion within a patient medical record. Examples of the processing performed are described below in further detail.

FIG. 13 illustrates an example patient data structure 1300 stored on the clinician database 1010 of FIG. 10, according to an example embodiment of the present disclosure. The patient data structure 1300 includes separate patient records for different patient. In the illustrated example, the data structure 1300 includes a patient medical record 1302 for a patient associated with identifier "DCM31913" and a patient medical record 1304 for a patient associated with identifier "GAM41215". The data structure 1300 may include additional patient medical records.

As shown in FIG. 13, each of the medical records 1302 and 1304 includes data fields that identify a patient, personal mobile communication device 200a, and home therapy machine 90. For example, the records 1302 and 1304 include data fields for a patient identifier, personal mobile communication device 200a type, home therapy machine 90 type, and home therapy machine identifier (received via registration). The patient identifier may correspond to the PAC assigned to the patient. The records 1302 and 1304 may include additional fields for a patient name, address, gender, birthdate, etc. The records 1302 and 1304 may further include fields for network addresses of the personal mobile communication device 200a and/or the home therapy machine 90. In some embodiments, the data access module 1106 of the application 1020 uses the information in the device type field to determine how the treatment information and medical information is to be presented and/or transmitted to the personal mobile communication device 200a.

Also as shown in FIG. 13, the medical records 1302 and 1304 include fields for treatment and medical information.

The data acquisition module 1104 stores treatment information to the records 1302 and 1304 received from the respective home therapy machines 90. In addition, the data acquisition module 1104 stores medical information to the records 1302 and 1304 received from the respective personal mobile communication device 200a. In some embodiments, the data fields are further partitioned into individual fields for data type. For example, the records 1302 and 1304 may include treatment information fields for a volume of fluid infused, an amount of ultrafiltration ("UF") removed from a patient, and/or a treatment time. The records 1302 and 1304 may also include data fields for alerts or alarms generated during a treatment and/or alarms or alerts determined at the clinician server 200b based on the treatment information and/or medical information. The records 1302 and 1304 may further include medical information for a patient's weight and/or blood pressure recorded before, during, and/or after a treatment.

The treatment and/or medical device may be organized by treatment, date/time generated, and/or date/time received. In some embodiments, the medical records 1302 and 1304 may store communications from a patient. The communications may include pictures or video recorded by the personal mobile communication device 200a related to a treatment or a question about a treatment. The communications may also include text messages, emails, etc. sent from the personal mobile communication device 200a regarding treatment assistance. Moreover, the communications may include information related to a request to change or modify a treatment from the personal mobile communication device 200a and/or a clinician device 152. Generally, the medical records 1302 and 1304 are configured to store information to improve a patient's engagement with a treatment in addition to documenting results of a treatment and information related to a patient's engagement with the clinician server 200b for the treatments.

The data received by the example data acquisition module 1104 varies based on the source. For instance, treatment information received from the home therapy machine 90 is generally structured. In other words, the home therapy machine 90 is configured to transmit treatment information that is formatted for direct entry into one or more fields of a patient's medical records. In some embodiments, the home therapy machine 90 formats messages for transmission through an API (or otherwise accesses one or more API) of the data acquisition module 1104 for population of treatment information into the appropriate data field. In contrast, medical information recorded by a patient's personal mobile communication device 200a may not initially be structured for inclusion into the patient's medical record. Different techniques may be used by the application 1002 of the personal mobile communication device 200a and/or the data acquisition module 1104 of the clinician server 200b to process and/or format medical information for population to a medical record, as described in more detail below.

1. Manual Entry of Medical Information into an Application Embodiment

To receive structured information, the example application 1002 of the personal mobile communication device 200a, in some embodiments, is configured to display prompts that indicate which medical information is needed for population, by a patient, into patient medical records. The example application 1002 may include a routine or algorithm that specifies which fields are to be displayed to prompt medical information from a patient. In some embodiments, the fields or screens in which the fields are displayed are arranged and/or ordered in relation to a medical fluid delivery treatment. The display of the fields informs a patient regarding which medical information is needed for a patient record.

Figure 15:
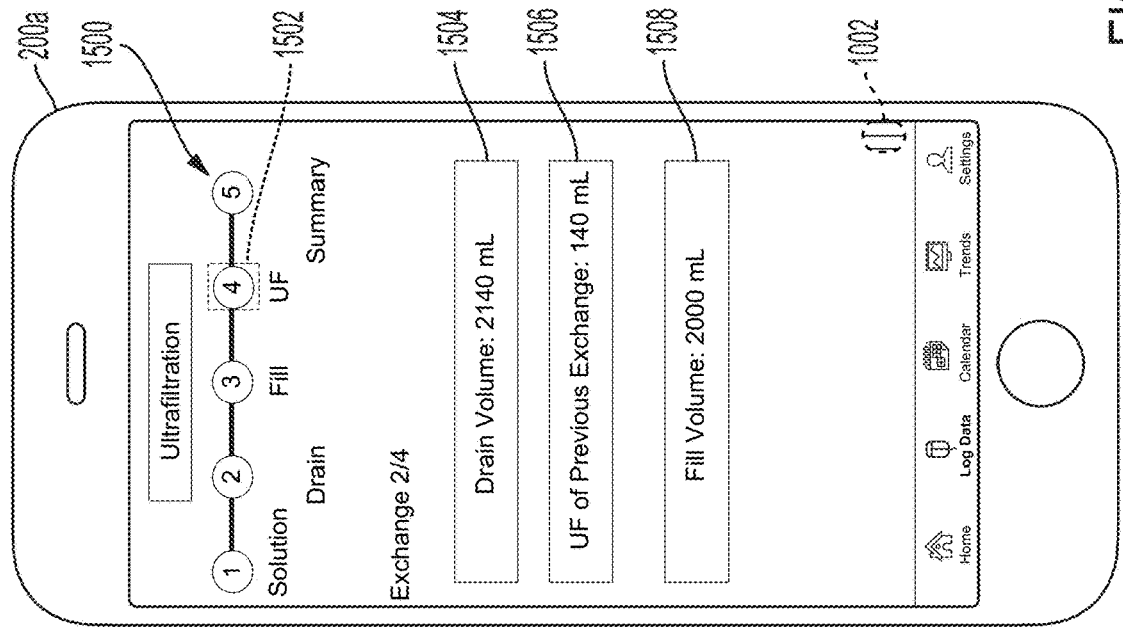
FIGS. 14 and 15 show diagrams illustrative of user interfaces of the application of FIG. 11, according to example embodiments of the present disclosure.
Figure 14:
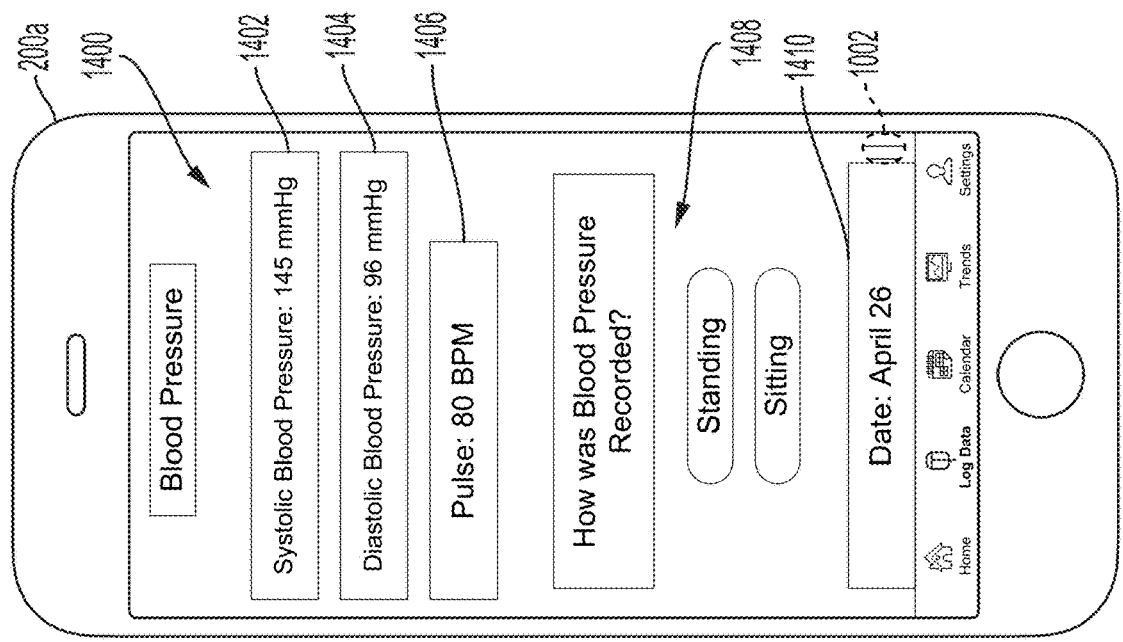

FIGS. 14 and 15 show diagrams illustrative of user interfaces of the application 1002 that enable a patient to enter medical information for transmission to the data acquisition module 1104. Specifically, user interface 1400 of FIG. 14 prompts a patient for blood pressure information while user interface 1500 of FIG. 15 prompts a patient for medical fluid delivery information (e.g., treatment information). It should be appreciated that the application 1002 of the personal mobile communication device 200a may display other user interface screens that enable a patient to manually enter medical information. For example, the application 1002 may display user interface screens for a blood glucose level, patient temperature, patient weight, etc.

In some embodiments, the patient may enter some of the medical information in the user interfaces 1400 or 1500 manually while obtaining other medical information wirelessly or recording some medical information via an image. In these configurations, the application 1002 may be configured to enable a patient to select an information entry source. A patient may enter medical information manually after selecting a manual source from a menu of available data entry methods or by default.

After receiving medical information manually entered by a patient, the example application 1002 transmits the medical information to the data acquisition module 1104 for population into a patient's medical record. The application 1002 and user interfaces 1400 and 1500 are configured such that the data fields for receiving medical information are aligned with data fields in one or more medical record. In some examples, the data fields may correspond to one or more APIs at the data acquisition module 1104 for writing medical information directly into the designed data field of a patient's medical record. The user interfaces 1400 and 1500 of the application accordingly prompt a patient for medical information in a structured manner such that identification or formatting of the medical information is not needed or necessary.

In some embodiments, the application 1002 may be configured to display the user interfaces 1400 and 1500 at designed times. For example, the application 1002 may include a calendar that includes times/days in which a treatment is scheduled. At a designed time before treatment (e.g., 5 minutes, 15 minutes, 30 minutes, etc.), the example application 1002 is configured to cause the personal mobile communication device 200a to display the user interface 1400, prompting a patient for blood pressure medical information. The prompt informs a patient that a blood pressure measurement is needed before treatment begins. The patient accordingly uses blood pressure monitor 104 to take a blood pressure measurement. The patient then enters value(s) of the measurement into the user interface 1400 before treatment begins.

In the illustrated embodiment, the user interface 1400 includes a systolic blood pressure data field 1402, a diastolic blood pressure data field 1404, and a pulse data field 1406. A patient may select the respective data field 1402, 1404, or 1406 causing the application 1002 to display a text entry feature to enter a value. The user interface 1400 also includes a field 1408 that enables a patient to specify if the blood pressure measurement was performed standing or sitting. Further, the user interface 1400 includes a data field 1410 that enables a user to specify a date/time the blood pressure measurement was performed.

In some examples, a patient may select any one of the fields 1402 to 1410 to receive more information about performing the corresponding measurement. For example, a patient may select the systolic blood pressure data field 1402, which causes the application 1002 to display a tutorial instructing a patient how to perform a blood pressure measurement and identify a systolic blood pressure measurement value. The tutorial may include text, text/pictures, an audio recording, an animation, and/or a video. The tutorial may be stored locally as part of the application 1002 or be stored at the clinician server 200b for remote access or streaming.

The user interface 1500 of FIG. 15 is configured to be displayed by the application 1002 when a patient is scheduled to perform a manual exchange treatment and/or if a home therapy machine 90 is not registered with the clinician server 200b. A manual renal failure exchange treatment requires that a patient connect containers of dialysis fluid to their peritoneal cavity for a dwell duration before allowing spent dialysis fluid to drain, all without the assistance of a machine. For a manual treatment, a patient needs to enter their manual exchange medical information to enable their records to reflect accurate treatment information.

The example application 1002 may also be configured to display the user interface 1500 when a patient does not register a home therapy machine 90. During registration, the registration module 1102 may transmit a message to the application 1002 indicative of whether a home therapy machine 90 has been registered. If a home therapy machine has not been registered, the application 1002 may be configured to display the user interface 1500 and/or other user interfaces for acquiring treatment information that may normally be transmitted by the home therapy machine 90.

In the illustrated example, the user interface 1500 includes a progression through a treatment, including a solution phase, a drain phase, a fill phase, a UF or dwell phase, and a summary phase. The application 1002 may display a separate user interface for each phase prompting a patient to enter corresponding or requested treatment information. The example user interface 1500 corresponds to a UF phase, as shown by a highlighted box 1502. The user interface 1500 includes a drain volume field 1504, a UF field 1506, and a fill volume field 1508. In the illustrated example, the user interface 1500 prompts a patient to enter a drain volume into data field 1504 during a drain phase and a fill volume into a data field 1508 during a fill phase. The user interface 1500 may calculate the UF value for the UF data field 1506 or prompt a patient for a value.

Instead of displaying the user interfaces 1400 and 1500 at designed times, the application 1002 may instead cause an alarm to be displayed on the personal mobile communication device 200a. The alarm may identify which medical information is needed or include a link to either of the user interfaces 1400 or 1500. The alarm may include a popup window displayed by the personal mobile communication device 200a. The alarm may also include an icon displayed adjacent to an icon for the application 1002 on a home screen of the personal mobile communication device 200a. In yet other embodiments, the application 1002 may not notify a patient about which medical information is needed. Instead, the application 1002 may enable a patient to navigate to the desired user interface to enter medical device data and/or treatment information.

In some embodiments, the application 1002 may identify at least some of the data fields of one or more user interface as being required for entry which other data fields are optional. The application 1002 may outline or otherwise graphically indicate while of the data fields are required (e.g., displaying a red box around the systolic blood pressure data field 1402). The application 1002 may cause an alert message to be displayed by the personal mobile communication device 200a if a required data field is not completed or not completed by a certain time. In some embodiments, the application 1002 may prevent a patient from navigating to another user interface until all required fields are populated for a currently viewed user interface.

After medical information is entered by a patient into one or more of the interface 1400 and 1500, the application 1002 transmits the medical information to the data acquisition module 1104 of the clinician server 200b for entry into the patient's medical record. The application 1002 is configured to transmit the medical information after a patient competes the data fields in the user interface or otherwise presses a send button on the interface. In other instances, the application 1002 may transmit the medical information at predetermined times, such as before or after a treatment.

2. Wireless Entry of Medical Information into an Application Embodiment

In some embodiments, a patient may select to enter medical information wirelessly in their personal mobile communication device 200a. The medical information may be received in the personal mobile communication device 200a via, for example, a Bluetooth® connection, a Zigbee® connection, a Z-Wave® connection, a wireless USB connection, a wirelessly RF connection, an NFC connection, an infrared connection, or any other suitable wireless communication technology. In some instances, a patient may have to wirelessly pair the personal mobile communication device 200a with the medical device, such as the blood pressure monitor 104 and/or scale 106. In other embodiments, a patient activates a connection application (e.g., an NFC application) that wirelessly reads medical information from a medical device.

In an example, a patient may pair their personal mobile communication device 200a with a blood pressure monitor 104. To enter the blood pressure medical information into the user interface 1400 of FIG. 14, the user selects, for instance, the systolic blood pressure data field 1402. Selection of the field 1402 causes the application 1002 to display a prompt asking the patient to select a data entry method (e.g., manual, wireless, photo, etc.). After selecting the wireless option, the application 1002 displays a menu of available wireless connection options and/or a list of paired Bluetooth® devices. The patient selects the blood pressure monitor 104 from the list, which causes a menu to be displayed of available medical information. The patient selects the systolic blood pressure, which causes the systolic blood pressure value to be populated into the systolic blood pressure data field 1402. In some embodiments, the application 1002 is configured to read the medical information from the blood pressure monitor 104 after the device is selected by the patient. The application 1002 may use data labels or metadata to determine which of the fields 1402 to 1410 is to be populated with medical information from the blood pressure monitor 104.

In some embodiments, the application 1002 is configured to enable a patient to establish a permeant or semi-permanent connection with a medical device. During a setup operation, the application 1002 prompts the patient to select a data field from the user interface 1400. After selection, the application 1002 prompts the patient to select a paired wireless medical device (and/or select a data type from a menu related the medical device). The selections by the patient configure the application 1002 to automatically read medical information from the blood pressure monitor 104, for example, when new medical information is available. In other words, the application 1002 is configured to access a remote medical device wirelessly automatically to read certain medical information to populate one or more data field. For instance, after a patient uses the blood pressure monitor 104 to take a blood pressure measurement, the monitor 104 transmits a ping or status message to the application 1002 indicative that new data is available. Alternatively, the application 1002 may poll or otherwise ping the blood pressure monitor 104 to determine if new data is available. The application 1002 then reads the new data into one or more of the data field 1402 to 1410 to automatically populate the user interface 1400. The application 1002 then sends the medical information to the data acquisition module 1104 of the clinician server 200b to automatically update the patient's medical record.

3. Image Entry of Medical Information into an Application Embodiment

The example application 1002 on the personal mobile communication device 200a is configured to enable a patient to enter medical information and/or treatment information by recording an image of a medical device or screen of a medical device. The personal mobile communication device 200a uses a camera 1004 to record one or more image. The application 1002 uses optical character recognition ("OCR") to extract text from the recorded image. The extracted text is populated in one or more data field of a user interface of the application 1002. The use of images may reduce data entry errors from patients or clinicians.

In some embodiments, the application 1002 uses rules or data templates to identify which text from an image may be selectable as relevant medical information for a data field. Otherwise, simply using an OCR feature makes all of the displayed text selectable. As such, a patient still has to copy and past the text from the image into a data field. By comparison, rules or data templates may group or identify text from an image as a field, which enables easy selection by a patient or automatic selection for population into a data field of a user interface.

The data templates or rules of the application 1002 are configured to organize or otherwise decipher extracted text from an image. The application 1002 determines or otherwise selects one or more data template for establishing a context for medical information based, for example, on a position of the medical information within the image and/or labels/keywords included within the medical information. To determine a data template, the example application 1002 may prompt a patient to specify a medical device type from which an image was recorded. Additionally or alternatively, the application 1002 enables a patient to select a medical device template. In yet other embodiments, a patient may first record an image of an identifier 1012 (e.g., an identifier image), which is used by the application 1002 to determine a type, model, etc. of the corresponding medical device. The application 1002 then selects a data template or rule that corresponds to the type, model, screen, etc. of the medical device.

The data templates define or specify data fields of certain medical information contained within an image. Generally, images include extracted text comprising medical information. In some instances, not all of the extracted medical information is needed or necessary. Instead, only certain medical information in a recorded image is needed for entry into a data field of a user interface or patient medical record. Relevant medical information or relevant medical information refers to medical device data or medical information that is identified or selected for population into a data field of a user interface of the application 1002, or more generally, for population into a patient's medical record.

Figure 16:
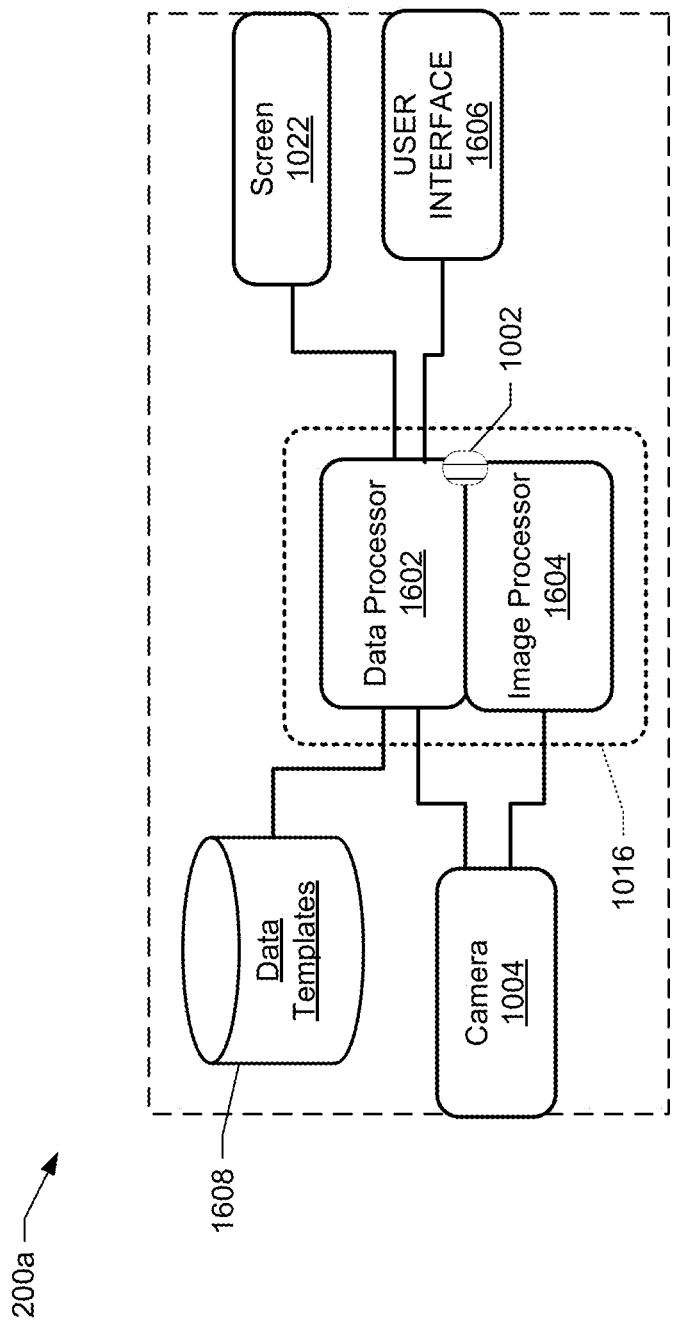
FIG. 16 is a schematic diagram of the personal mobile communication device of FIGS. 10 and 11, according to an example embodiment of the present disclosure.

FIG. 16 illustrates a schematic diagram of the personal mobile communication device 200*a* for recording and processing images for medical information extraction, according to an example embodiment of the present disclosure. The illustration of the personal mobile communication device 200*a* is exemplary and some of the blocks may be combined, further partitioned, or removed. In addition, in some embodiments, the personal mobile communication device 200*a* may include additional blocks, such as a memory 1018 storing instructions, which when executed by a data processor 1602 (or more generally, processor 1016), cause the application 1002 to process images to extract medical information.

The example data processor 1602 may be configured to manage the acquisition of medical information from one or more image. Such management includes displaying, via the screen 1002, one or more camera message that provides information prompting a clinician or a patient (e.g., an operator) to record certain images. Alternatively, the data processor 1602 may initiate an image processing mode after a patient has selected to input medical information into one or more data field of the application 1002 using an image entry method. After selection of an image entry method, the data processor 1602 is configured to acquire one or more image.

In some embodiments, the data processor 1602 causes the personal mobile communication device 200*a* to open a camera application to enable a patient to record one or more images. A patient may select which of the recorded images are to be further processed or discarded. The selected images are analyzed to identify text (as medical information) for potential population into data fields of one or more user interface of the application 1002.

In other embodiments, the data processor 1602 may guide the patient through one or more steps for acquiring the images. The data processor 1602 may execute a workflow or routine based on which data field(s) was selected by the patient. For example, the data processor 1602 executes a blood pressure workflow for obtaining an image from a blood pressure monitor based on a patient selecting the systolic blood pressure data field 1402.

In an example, the data processor 1602 of FIG. 16 is configured to display camera messages that identify a medical device, a user interface window of a medical device, and/or an identifier on a medical device that is to be recorded. The data processor 1602 may also display navigation messages that specify a user interface window of a medical device for imaging. Moreover, the data processor 1602 may display reminder messages if an image is not recorded within a predetermined time period (e.g., five minutes). The messages may include text that provides instructions and/or identifying the intended target for imaging. The messages may also include instructions regarding how to navigate to a certain user interface window of a medical device using control interfaces of the medical device. The messages may further include graphical elements, such as an exemplary illustration of a medical device, a consumable items, identifier 1012, and/or user interface window for which an image is to be recorded.

It should be appreciated that in some embodiments, the data processor 1602 does not display messages. Instead, the data processor 1602 is reactive to images recorded by a patient to determine relevant medical information. For example, upon receiving an indication that an image is recorded, the data processor 1602 operates a workflow in which the application 1002 prompts a clinician to identify a medical device from which the image has been recorded. The prompt may include a pull-down menu of available or common medical devices. In other examples, the data processor 1602 automatically identifies medical information using one or more data templates or data labels to determine which extracted medical information is to be populated or written into a data field of a user interface or medical record.

To record an image, the example data processor 1602 and an image processor 1604 (more generally processor 1016) provide operations for the application 1002 in connection with the camera 1004. A patient provides an indication via a camera user interface 1606 (e.g., a touchscreen or button on the personal mobile communication device 200*a*) to record an image. The patient actuates the camera user interface 1606 when, for example, a camera is focused on a medical device user interface window or identifier 1012. The data processor 1602 receives the indication and instructs the camera 1004 to record an image. The recorded image is transmitted from the camera 1004 to the image processor 1604. In addition, a copy of the image is displayed by data processor 1602 on the display interface 1022 of the personal mobile communication device 200*a*.

In some embodiments, the data processor 1602 may cause a ghost image to appear on the display interface 1022 that is illustrative of an image to be recorded. The ghost image is provided on top of a stream of images provided by camera 1004 in a preview mode. The purpose of the ghost image is to provide assistance to a clinician or patient confirming that the image to be recorded contains the desired medical information and is recorded at an appropriate distance. For example, the data processor 1602 may display a ghost image of a given identifier on a given medical device. The patient aligns the personal mobile communication device 200*a* such that a stream of images of identifier 1012*a* is aligned positionally with the ghost image. The patient may then record the image of identifier 1012*a*. In some instances, the data processor 1602 uses image analysis to determine deltas between the ghost image and the stream of images. The data processor 1602 may cause instructions to be displayed that prompt a patient to move the personal mobile communication device 200*a* in a certain direction to reduce the determined deltas. The data processor 1602 may determine when the deltas are below a threshold, indicating that the images are aligned. Once the images are substantially aligned, the data processor 1602 may provide a graphical indication on display interface 1022 indicative that an image can be recorded or automatically cause the image to be recorded without input from a patient.

The data processor 1602 may provide a prompt asking the patient to accept the image. After receiving an indication via camera user interface 1606 of acceptance, image processor 1604 may analyze the image to identify or otherwise extract text. In some instances, the data processor 1602 may not prompt a clinician to accept an image. Instead, a patient may provide an indication via the camera user interface 1606 to delete an image. Until an image is deleted, the image processor 1604 performs an analysis to identify text.

To identify text, the image processor 1604 uses, for example, OCR. In addition, the image processor 1604 may determine a location or position of the text with respect to a center or origin of the image. In some instances, the image processor 1604 may assign two-dimensional coordinates to each character or group of characters. The positional text information may be stored to an image file of the image as metadata. The image processor 1604 may also use a clock of the personal mobile communication device 200*a* to attach a date/time (corresponding to a time when the image was recorded) to metadata associated with the image.

In addition to performing OCR to identify text, the image processor 1604 may also be configured to identify patients, medical devices, and/or consumable items using image analysis. For example, the image processor 1604 may access a library of medical device images to identify a medical device within an image. In this example, the image processor 104 may use image matching routines to determine a match. Such a comparison may be made in lieu of the medical device having an identifier 1012. The image processor 1604 may use similar routines and/or algorithms for identifying consumable items 1006.

The example data processor 1602 is configured to decode identifiers 1012 to determine a type of medical device of consumable item. Decoding may include correlating positions and thicknesses of lines and/or rectangles into relevant medical information. The coded lines and rectangles may correspond to a sequence of letters and/or numbers. For example, the data processor 1602 may use the lines or rectangles of the identifier 1012 to determine a device model number, medical device type, asset code, etc. The decoded identifiers 1012 may provide relevant medical information for population into one or more data field of a user interface of the application 1002. Additionally or alternatively, the decoded identifiers may be used by the data processor 1602 for selecting a workflow for acquiring images from a medical device or consumable and/or for determining a data template.

The example image processor 1604 of FIG. 16 transmits the images with the extracted or otherwise identified text and/or medical information to data processor 1602. The example data processor 1602 uses, for example, one or more data templates from a data template database 1608 to identify relevant medical information from the extracted text. In some examples, data processor 1602 receives data templates from the clinician server 200*b*, which may then be stored in database 1608. In other examples, the data processor 1602 maintains the database 1608 with data templates.

Figure 17:
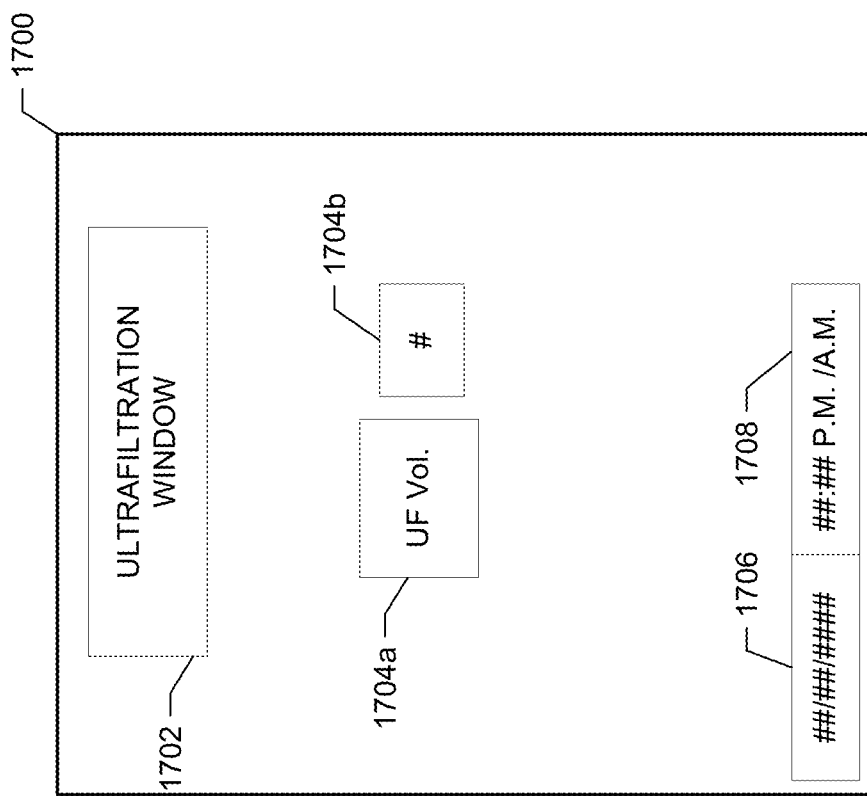
FIG. 17 illustrates a schematic diagram of a data template, according to an example embodiment of the present disclosure.

FIG. 17 illustrates a schematic diagram of a data template 1700, according to an example embodiment of the present disclosure. The example data template 1700 is used by the image processor 1604 (e.g., the application 1002) to identify extracted text as relevant medical information. Generally, screens of medical devices display medical information. Some of the information is relevant for inclusion in a data field of a user interface of the application 1002. Other of the data may be less relevant or not relevant. Further, depending on a model of medical device, the medical information may be in different locations or have different labels. The data template 1700 is configured to specify locations and names of relevant medical information for a particular home therapy machine 90.

The data template 1700 is stored in the database 1608 with a plurality of other data templates for different types and/or models of medical devices and/or consumable items. After receiving an identifier 1012 of a medical device (or specification of a medical device or data field by a patient), the image processor 1604 selects a corresponding data template 1700. Additionally or alternatively, the image processor 1604 may use image processing to select a data template that best matches a recorded image using, for example, information labels or text position.

The example data template 1700 of FIG. 17 includes device data (or text) fields 1702, 1704, 1706, and 1708 that specify where certain medical information is located on a particular user interface window of a medical device. In some examples, the data template 1700 is graphical such that an image analysis is performed to align fields 1702 to 1708 with extracted text in an image. In other examples, the data template 1700 includes a file (or other data structure) having coordinates or positions for each of device data fields 1702 to 1708 relative to an origin. The image processor 1604 identifies an origin in an image with extracted text and identifies text for each of data fields 1702 to 1708 based on substantial matches to locations in the data template 1700. In some examples, image processor 1604 may scale the image to match a size or coordinate space of data template 1700.

Some of the illustrated data fields 1702 to 1708 may include label text in addition to coordinates or locations. For example, device data field 1702 includes label text "Ultrafiltration Window", while device data field 1704*a* includes label text "UF Vol.". The image processor 1604 matches the label text to similar text extracted from an image. In some instances, matches between label text are used exclusively for identifying device data fields, rather than using positional or image analysis.

Matches between the label text, including label text for non-relevant device data fields, may be used to confirm that the image is from the correct window or screen of a medical device. For example, the image processor 1604 may match label text "Ultrafiltration Window" to corresponding extracted text in relatively the same location of a recorded image. The match confirms that the image has been recorded from an ultrafiltration window of a renal failure therapy medical device. However, the extracted text is not relevant medical information for a patient's medical record. If the label text does not match the extracted text, the image processor 1604 may display a message prompting a patient to record an image of the Ultrafiltration Window of renal failure therapy medical device.

The label text associated with device data fields 1706 and 1708 may be used to confirm a recorded image is current, or recorded within a determined time period. For example, some windows of medical devices display a current date and time. This information may be extracted by image processor 1604 and identified using device data fields 1706 and 1708. The image processor 1604 compares the extracted date/time to date/time rules or limits associated with the device data fields 1706 to 1708 to determine whether the recorded image is current. For example, the image processor 1604 may determine another image is required to be recorded if the date does not match or the time is not within a predetermined threshold (e.g., five minutes, 15 minutes, 60 minutes, 3 hours, etc.) of a current time on the personal mobile communication device 200*a*.

The example device data fields 1704*a* and 1704*b* of FIG. 17 are used by the application 1002 to identify relevant medical information. In some instances, the application 1002 may display a flag or metadata indicative that device data fields 1704*a* and 1704*b* are relevant to a selected data field of a user interface (e.g., the user interface 1400 or 1500). By comparison, device data fields 1702, 1706, and 1708 may include a flag or metadata indicative that the corresponding extracted data is not relevant. In the example illustrated in FIG. 17, the image processor 1604 uses the label text of the data field 1704*a* to locate corresponding extracted text in an image. The image processor 1604 then uses a positional relationship between device data fields 1704*a* and 1704*b* or text value markers to identify extracted medical information from the image that corresponds to the numerical value of the ultrafiltration volume. The image processor 1604 copies the extracted medical information related to field 1704*b* from the image to populate, for example, the systolic blood pressure data field 1402 of FIG. 14.

As discussed above in connection with FIG. 17, the data processor 1602 of FIG. 16 may use known positional relationships of text in an image and text label(s) to determine which of the extracted text corresponds to relevant medical information. In some embodiments, data processor 1602 selects a data template based on an indication of the model or type of medical device and/or consumable item. The indication may be determined from a previous image of an identifier 1012, received from a patient via the camera user interface 1606, and/or specified through a selection of a data field of a user interface for the application 1002 to which the medical information is to be populated. In other examples, the data processor 1602 compares the data templates in the database 1608 to the image with the extracted text to find a match. In these other examples, the data processor 1602 uses text labels and a position of the text between the image and data templates to determine a match.

The example data processor 1602 is configured, after identifying relevant medical information, to write or otherwise populate the relevant medical information into one or more data field of a user interface of the application 1002. In some embodiments, the data processor 1602 is configured to automatically populate the data fields of a user interface of the application 1002 using a data template. To automatically populate medical information, the data processor 1602 compares text, labels, and/or metadata associated with fields of a data template to the text, labels, metadata, and/or other data field information of one or more user interface of the application 1002. If at least some of the text, labels, and/or metadata match, the data processor 1602 identifies certain text (e.g., numerical values) corresponding to the matching field of the data template. The identified text is written to the corresponding matching data field of the user interface of the application 1002.

Figure 18:
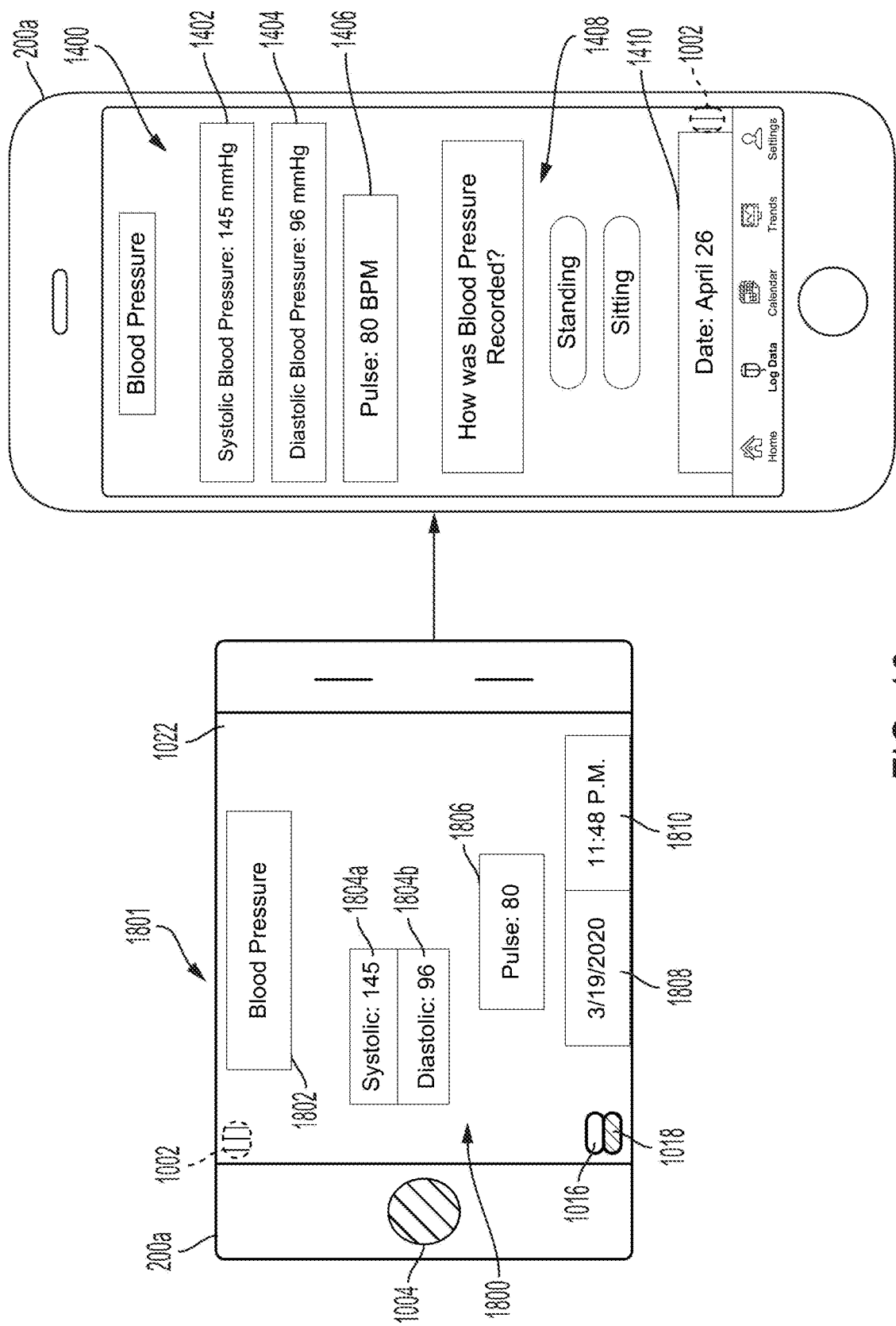
FIG. 18 shows a diagram illustrative of a writing to data fields of the user interface of FIG. 14, according to an example embodiment of the present disclosure.

In other embodiments, the data processor 1602 is configured to prompt a patient to select one or more field of a data template to populate one or more data field of a user interface of the application 1002. FIG. 18 shows a diagram illustrative of a patient populating data fields 1402 to 1406 of the user interface 1400, according to an example embodiment of the present disclosure. In the illustrated example, the user interface 1400 is opened on the personal mobile communication device 200*a*. To enter medical information into the data fields 1402 to 1406, a patient selects each of the data fields sequentially or together. For each selection, the application 1002 displays a prompt asking the patient how the data is to be entered. After a patient selects a photo entry method, the application 1002 opens a camera application to enable a patient to record an image 1800 of a screen of the blood pressure monitor 104 using the personal mobile communication device 200*a*. In some embodiments, the application 1002 may display text or graphics to assist the patient in acquiring the image, as described above.

After the image 1800 is recorded, the application 1002 performs an OCR operation to extract text. The application 1002 then determines a data template 1801 that corresponds to the extracted text. In some embodiments, the application 1002 matches locations of the text and/or labels within the image to text and/or label locations in data templates to find a matching data template. In other examples, the patient may specify an indication of the blood pressure monitor 104, which enables the application 1002 to locate the corresponding data template 1801. In yet other examples, the application 1002 may first prompt a patient to record an image of the identifier 1012*a* of the blood pressure monitor 104. Data from the identifier is used by the application 1002 to select the data template. Regardless of how the data template 1801 is identified, the application 1002 applies the data template 1801 to the extracted text in the image 1800. This process includes the application 1002 identifying groups or fields of similar text. In some instances, the application 1002 may identify groups or fields of similar text based on spacing between letters and/or words.

In the illustrated example of FIG. 18, the application 1002 provides fields 1802, 1804*a*, 1804*b*, 1806, 1808 and 1810 for the different sets of text. The patient selects the field from which data is to be populated into the selected data field of the user interface 1400. For example, to populate the systolic blood pressure data field 1402, the patient selects the field 1804*a*. The selection by the patient causes the application 1002 to copy at least some of the data from the field 1804*a* to the data field 1402. The data field 1402 may include a rule that specifies only a numerical integer may be accepted. The application 1002 reads the text from the selected field 1804*a* for numeric integers (i.e., "145"). The application 1002 then populates the identified numeric integers into the systolic blood pressure data field 1402. The patient may continue for the other fields 1404 to 1410 of the user interface 1400 using the image 1800. In each instance, the patient may select between entering the data manually, wirelessly, or via an image. If a second image is needed (e.g., prompted by the application 1002 or determined by the patient), the application 1002 enables the patient to record and view multiple images. The application 1002 applies the appropriate data template to each of the recorded images. The application 1002 accordingly enables a patient to enter information into the user interface 1400 using one or more recorded image as though the patient is manually entering the values.

In some embodiments, the application 1002, and more specifically, the data processor 1602 performs a check on the extracted data selected by a user to ensure the values are within a predetermined range and/or of a specified type. The application 1002 may perform similar checks for data manually entered by a patient or data received wirelessly from a medical device. Each data template and/or data field of a user interface may include metadata or rules for certain fields that provide thresholds or acceptable ranges of values. For example, metadata or rules for a weight data field may specify that a predetermined acceptable range of values is between 20 kg and 200 kg. For values outside the predetermined range, the application 1002 may display an error on the display interface 1022 or prompt a patient to record another image or amend the value.

Figure 19:
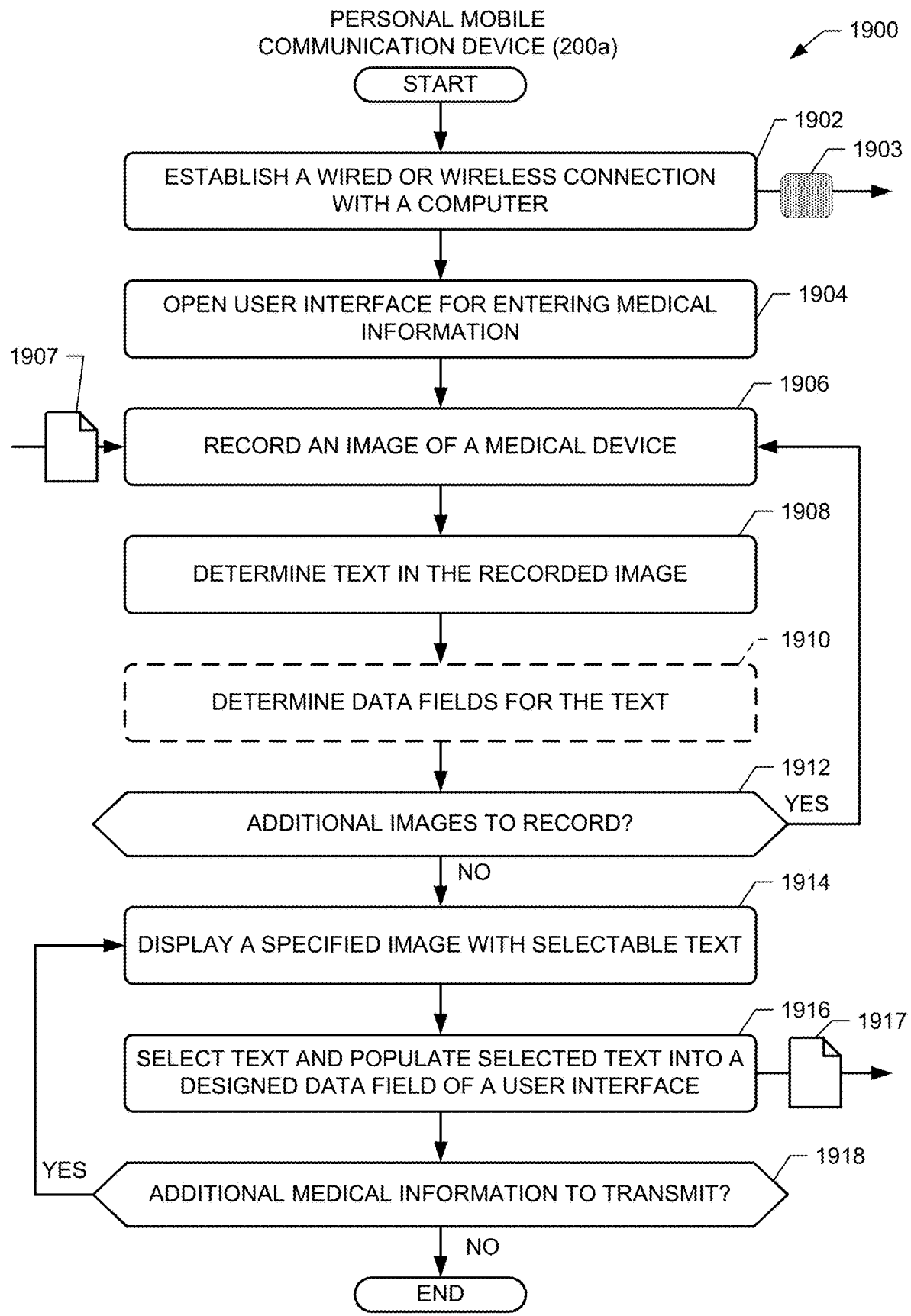
FIG. 19 is a flow diagram of an example procedure for entering medical information from an image using the application of the personal mobile communication device of FIGS. 10 and 11, according to an example embodiment of the present disclosure.

FIG. 19 illustrates a flow diagram of an example procedure 1900 for entering medical information from an image using the application 1002 of the personal mobile communication device 200*a*, according to an example embodiment of the present disclosure. Although procedure 1900 is described with reference to the flow diagram illustrated in FIG. 19, it should be appreciated that many other methods of performing the steps associated with the procedure 1900 may be used. For example, the order of many of the blocks may be changed, certain blocks may be combined with other blocks, and many of the blocks described may be optional. In addition, example procedure 1900 may include optical blocks for prompting a patient to record an image of a screen and/or identifier 1012 of a medical device.

Example procedure 1900 begins in one embodiment when the application 1002 is launched on the personal mobile communication device 200*a* and operates with processor 1016 to establish a wired and/or wireless connection with the clinician server 200*b* (block 1902). Establishing a connection may include, for example, transmitting and/or receiving one or more message 1903 that provides a device address, patient identifier, device identifier, network address, and/or protocol information for accessing and/or writing to a patient's medical records. After opening the application 1002, the patient navigates or otherwise accesses a user interface (e.g., the user interfaces 1400 or 1500 of FIGS. 14 and 15) for entering medical information (block 1904).

Before block 1906, a patient uses the application 1002 to select a data field and select that medical information is to be provided via photo entry. At block 1906, the personal mobile communication device 200*a* records an image 1907 of a medical device, consumable, patient, etc. The image may include an identifier and/or a screen of a medical device. The personal mobile communication device 200*a* then determines or identifies text within the recorded image (block 1908). For example, the personal mobile communication device 200*a* may perform an OCR routine on the image. In instances in which the image includes a barcode and/or a QR code, the personal mobile communication device 200*a* decodes the barcode and/or QR code. The imaged or coded data is converted into textural or American Standard Code for Information Interchange ("ASCII") characters. In some embodiments, the personal mobile communication device 200*a* may also determine data fields for the identified text (block 1910). The data fields may be determined using, for example, a data template. As described above in connection with FIGS. 17 and 18, the data template may specify locations of certain text and/or specify labels of certain text used for placing data fields operationally over identified text within the recorded image. In some instances, the data fields and/or data template may be selected by a patient and/or determined from an identifier 1012 of the medical device. Alternatively, instead of using templates, the procedure 1900 may instead provide an indication that the recently recorded image has relevant medical information for extraction, selection, and/or transfer.

The example procedure 1900 continues in one embodiment by determining if there are additional images to record (decision block 1912). In an example, the procedure 1900 may access a list of images needed to be recorded for a specified therapy or treatment. The procedure 1900, via the personal mobile communication device 200*a*, may guide a patient through a sequence to obtain all needed images or provide prompts to obtain images containing medical information that is determined to be needed or missing. In other instances, the patient may determine which images are needed. If additional images are to be recorded, the procedure 1900 returns to block 1906.

If no additional images are needed, as determined at decision block 1912, a patient begins the process to populate relevant medical information into data fields of a user interface. The process in the illustrated embodiment includes enabling the patient to select an image from which relevant medical information is to be transferred. The selection of the image causes the personal mobile communication device 200*a* to display the image on the display interface 1022 (block 1914). It should be appreciated that the selected image includes identified text, and optionally data fields. The patient may also specify the data field (or location in the data field) of the user interface to which the data is to be populated.

The personal mobile communication device 200*a* receives a selection of the relevant medical information and/or data fields with relevant medical information for population into a designed data field of a user interface of the application 1002. Selection may be performed by the patient pressing on the area of the touch screen 1002 of the personal mobile communication device 200*a* corresponding to the medical information to be populated. Selection of the relevant medical information and/or fields causes the personal mobile communication device 200*a*, in an embodiment, to automatically populate at least a portion of the selected text (block 1916).

After the selected text has been populated, the personal mobile communication device 200*a* determines if additional relevant medical information is to be populated based on a selection of additional data fields of a user interface (decision block 1918). In some examples, the personal mobile communication device 200*a* operates a sequence or routine that provides prompts for a patient to select the appropriate text and/or images for populating into data fields. If there is additional relevant medical information, as determined at decision block 1918, the procedure 1900 returns to blocks 1914 and 1916, where the patient specifies the image and/or relevant medical information for data field population. If there is no additional relevant medical information for population, as determined at decision block 1918, the example procedure ends 1900.

4. Image/Text Attachment Application Embodiment

The example application 1002 and clinician server 200*b* in some embodiments are configured to enable patients to provide images or text as attachments or addendums to their medical records. In the above sections, the application 1002 provides data fields of user interfaces as prompts for desired information. However, in some instances, a patient or clinician may want to provide additional information. Additionally or alternatively, one or more user interfaces of the application 1002 may include data fields for free text entry, prompts for a patient to enter text (e.g., "how are you feeling today"), or features to enable a photo or image to be incorporated as part of the record. For example, the user interface 1400 may include a photo icon adjacent to a prompt for an image of a fluid connection to the patient's abdomen, which when selected, opens a camera application to enable a patient to attach an image for transmission with the medical information. The images may be stored to designed fields in the appropriate patient medical record.

The example application 1002 on the personal mobile communication device 200*a* is configured to accept images and/or text provided by a patient. In an embodiment, the application 1002 is configured to enable a patient to select between text or photo entry. If a patient selects text entry, the application 1002 displays a text box. A patient enters information into the text box, which is stored by the application 1002. The application 1002 may then transmit the information in one or more message to the clinician server 200*b*. The application 1020 at the clinician server 200*b* determines the appropriate patient medical record in the database 1010 and locates a "note" or free text field. The application 1020 stores the patient provided text into the field. In some instances, the application 1020 may also include a time/date stamp with the entered text. This information provides a clinician with additional information from a patient, including feedback regarding the treatment.

Figure 20:
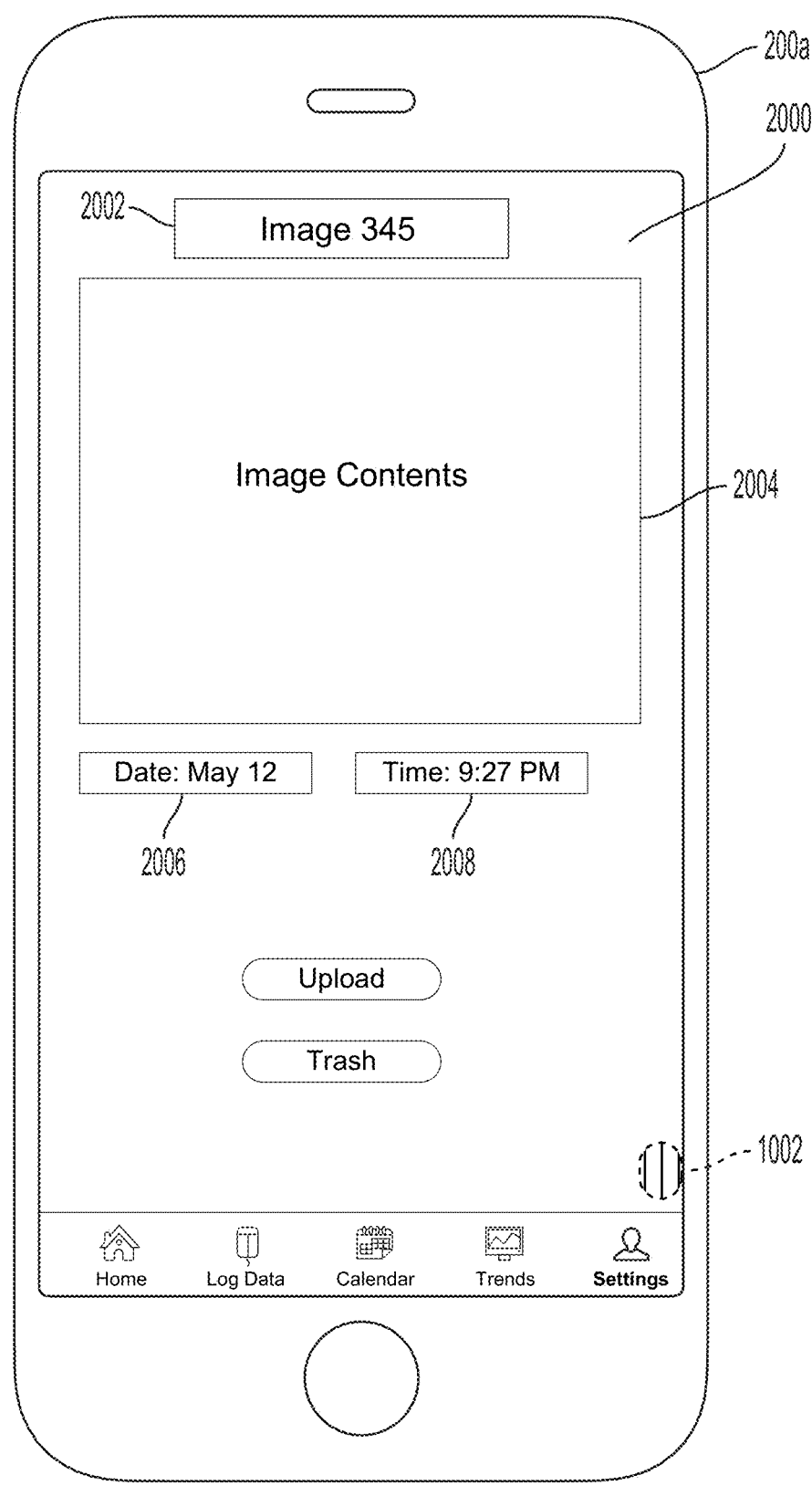
FIG. 20 shows an example of a user interface displayable by the application on the personal mobile communication device of FIGS. 10 and 11 that enables a patient to provide a recorded image, according to an example embodiment of the present disclosure.

FIG. 20 shows an example of a user interface 2000 displayable by the application 1002 on the personal mobile communication device 200a that enables a patient to provide a recorded image, according to an example embodiment of the present disclosure. The example user interface 2000 includes an image title field 2002, which may be editable by a patient. The user interface 2000 also includes one or more recorded image 2004, or a preview of recorded image. The application 1002 is configured to enable a patient to browse a gallery folder of recorded images to select which images are to be transmitted. A date field 2006 and a time field 2008 provide information in the user interface 2000 indicative of a date/time the displayed image was recorded. A patient may select a "Trash" button to discard the image 2004 or a "Upload" button to transmit the image 2004 from the application 1002 to the clinician server 200b. The example photo capture feature of the application 1002 enables a patient to document fluid line connectivity with the home therapy machine 90 or physiological conditions related to a treatment. The application 1020 at the clinician server 200b is configured to attach or otherwise link the received image 2004 to the patient's medical record.

5. Manual/Wireless/Image Entry Medical Information Via Text Embodiment

In some embodiments, the personal mobile communication device 200a of FIGS. 10 to 12 may not be capable of installing or operating the application 1002, or a patient may decide not to install the application 1002. However, the clinician server 200b still registers the personal mobile communication device 200a during a registration process. Instead of receiving medical information via the application 1002, the data acquisition module 1104 of the clinician server 200b determines that a routine or algorithm is to be executed for prompting or otherwise obtaining medical information from a patient via the personal mobile communication device 200a. The example data acquisition module 1104 may read a registration file and/or medical record of the patient to determine the personal mobile communication device 200a is registered but the application 1002 is not installed.

In some embodiments, the data acquisition module 1104 is configured to obtain medical information from a patient through one or more text messages. For instance, at designed times, corresponding to times of prescribed treatments, the data acquisition module 1104 may transmit one or more text messages prompting a patient to respond with medical information using the registered personal mobile communication device 200a. In other instances, the data acquisition module 1104 is configured to respond to a text from a patient to begin a sequence or routine for acquiring medical information. In yet other instances, the patient may send a text message with medical information and/or images to the data acquisition module without a prompt message.

The example data acquisition module 1104 of FIG. 11 is configured to format or otherwise structure the received information for population into one or more data field of a patient's medical record. Generally, medical information received from a text message is unstructured. In other words, the text message does not provide a clear correlation or reference to a designed field of a patient's medical record. Instead, the data acquisition module 1104 is configured to determine appropriate fields for the medical information received in the text message.

In some embodiments, the data acquisition module 1104 uses a context of the received text message from the personal mobile communication device 200a to determine a data field. For example, a patient may send a message that includes the text "systolic blood pressure 145". The data acquisition module 1104 compares at least some of the text (e.g., one or more words in a string) to field data labels, keywords, and/or metadata. If at least some of the words match, the data acquisition module 1104 is configured to identify a numeric value in the contents of the text message and write the identified numeric value in a data field of a patient's medical record corresponding to the matching text. In some embodiments, the data acquisition module 1104 may compare the value to an acceptable range of values before writing the value. If the value is outside the acceptable range, the data acquisition module 1104 may transmit, to the personal mobile communication device 200a, a message indicative of the error or a message prompting a patient to reenter the value.

In these embodiments, the data acquisition module 1104 may be configured to send follow-up texts to a patient if text from a received text message cannot be properly placed into a data field. For example, the data acquisition module 1104 may receive a message with text comprising "blood pressure 145". The data acquisition module 1104 determines the message may correspond to "systolic" or "diastolic" blood pressure data fields based on matching text. Accordingly, the data acquisition module 1104 transmits a message to the personal mobile communication device 200a with text asking a patient if the value is "systolic" or "diastolic".

In other embodiments, the data acquisition module 1104 prompts a patient through a sequence of messages (that may be defined by a routine or algorithm) to provide certain medical information. The order of the sequence is known or defined and corresponds to data fields in a medical record. As such, the data acquisition module 1104 automatically determines that a response to a certain prompt corresponds to the data field of a medical record that is related to the prompt. For example, the data acquisition module 1104 transmits a text message prompting a patient for a "systolic blood pressure measurement". The data acquisition module 1104 determines that a response to the text contains a value for the "systolic blood pressure measurement". The data acquisition module 1104 may analyze the received message to identify the numeric value among other text and/or compare the value to an acceptable range. After confirming the patient provided an acceptable response with medical information, the data acquisition module 1104 determines a subsequent message to send to the personal mobile communication device 200a based on the sequence of messages.

Instead of receiving messages with text, the data acquisition module 1104 may also receive messages with a photo attachment. Similar to the process described above in connection with FIGS. 16 to 19, the data acquisition module 1104 is configured to process the image to extract text and identify relevant medical device data for one or more data field of a medical record. Further, while the above-disclosure describes the use of text messages, the data acquisition module 1104 may additionally or alternatively receive the medical information and/or photos via other communication mediums, such as emails, instant or web-based messages, social media posts, etc.

Figure 21:
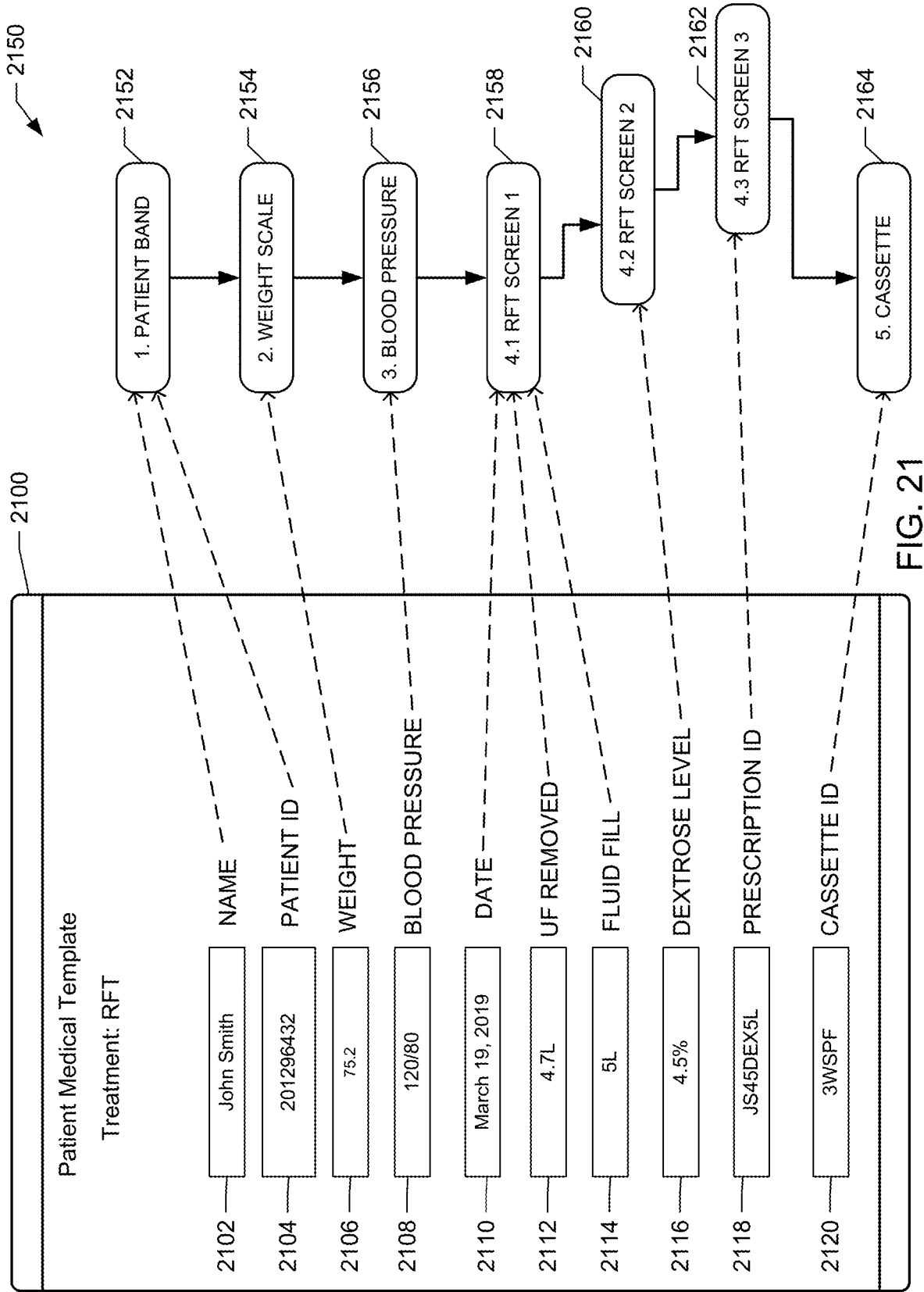
FIG. 21 shows a schematic diagram of a patient medical template used by the clinician server of FIGS. 10 and 11 to populate data fields of a patient's medical record, according to an example embodiment of the present disclosure.

FIG. 21 shows a schematic diagram of a patient medical template 2100 that may be used by the data acquisition module 1104 of the clinician server 200b to populate data fields of a patient's medical record, according to an example embodiment of the present disclosure. Fields of the template 2100 may correspond to or otherwise be linked or referenced to data fields of a patient's medical record. In other embodiments, a copy of a completed template 2100 may be stored to a medical record or as a medical record itself. In some embodiments, the patient medical template 2100 may be part of or otherwise integrated with a patient's medical record.

The example template 2100 includes predefined fields 2102, 2104, 2106, 2108, 2110, 2112, 2114, 2116, 2118, and 2120 that correspond to a renal failure therapy treatment ("RFT"). The example data acquisition processor 1104 may select the template 2100 based on the treatment prescribed for a patient. While an RFT template 2100 is illustrated, the example data acquisition module 1104 may select other templates configured specifically for pre-treatment data acquisition, post-treatment data acquisition, etc. For example, a pre-treatment acquisition template may include data fields for blood pressure, pulse, and weight.

It should be appreciated that in other embodiments, the patient medical template 2100 may include additional or fewer fields. For example, the template 2100 may additionally include data fields for pre-treatment patient weight and post-treatment patient weight, patient glucose level, and/or patient birth date. In another example, the template 2100 may include fields for a fill rate, a dwell time, a drain or fluid removal rate, a blood flow rate, an effluent dose, an ultrafiltration removal rate, a dialysis solution removal rate, a total dialysis solution infused, dialysis solution flow, replacement pre-flow, replacement post-flow, patient weight balance, return pressure, excess patient fluid sign, filtration fraction, a time remaining, dialysis solution concentration, dialysis solution name, a patient identifier, a room identifier, a care area identifier, a timestamp indicative of when the data was generated, an alarm condition, an alert condition, and/or an event.

In some embodiments, the data acquisition module 1104 is configured to select the template 2100 based on a prompt from a patient. For example, a patient may send the data acquisition module 1104 a message including text of "manual exchange". In response, the data acquisition module 1104 identifies and selects the template 2100 for a manual exchange. In another example, a patient may send the data acquisition module 1104 a message, via the personal mobile communication device 200a, including text of "pre-treatment" or "begin treatment". In response, the data acquisition module 1104 identifies and selects a template for acquiring medical information needed before a treatment begins.

In the illustrated example of FIG. 21, the example data fields include a field 2102 for a patient's name, a field 2104 for a patient identifier, a field 2106 for a patient's weight, a field 2108 for a patient's blood pressure, a field 2110 for a date of treatment, a field 2112 for an amount of UF removed, a field 2114 for an amount of total fluid provided to a patient, a field 2116 for a dextrose level, a field 2118 for a treatment prescription identifier, and a field 2120 for a disposable cassette identifier. In instances where the renal therapy machine 90 is registered with the clinician server 200b, the data acquisition module 1104 may remove at least fields 2112 to 2120 (or select a separate template with the fields 2112 to 2120 omitted) because such information is already provided by the machine 90. However, the fields 2112 to 2180 may be used in the template if a patient is reporting a manual exchange. Further, the template 2100 may omit fields 2102 and 2104 based on at least some of the patient information already having been registered.

The example data fields of the patient medical template 2100 may be populated from one or more different sources of medical information including, device information, patient information, and/or consumable item information. For example, the patient name field 2102 and patient identifier field 2104 may be populated from image(s) recorded by the personal mobile communication device 200a of an identifier 1012 of a patient (or an identifier 1012 worn by the patient). The blood pressure field 2108 may be populated from an image recorded by the personal mobile communication device 200a of a screen of the blood pressure monitor 104, while the weight field 2106 may be populated from an image recorded by the personal mobile communication device 200a of a screen of the scale 106. The date field 2110, the UF removed field 2112, and the fluid fill field 2114 may be populated from an image recorded by the personal mobile communication device 200a of a screen (showing a treatment status window) of the home therapy machine 90. Similarly, the dextrose level field 2116 may be populated from an image recorded by the personal mobile communication device 200a of a screen (showing a setup window) of the home therapy machine 90, while the prescription identifier field 2118 may be populated from an image recorded by the personal mobile communication device 200a of a screen (showing a prescription window) of the home therapy machine 90. Finally, the cassette identifier field 2120 may be populated from an image recorded by the personal mobile communication device 200a of an identifier 1008 of a disposable cassette consumable item 1006. As discussed above, the data acquisition module 1104 may receive one or more message with text for the fields 2102 to 2120 instead of receiving images containing the medical information.

The patient medical template 2100 illustrated in FIG. 21 is configured to be stored on the clinician database 1010 and accessed by the clinician server 200b illustrated in FIGS. 10 and 11. Upon receiving a request to populate a template for a patient, the clinician server 200b is configured to make a copy or create an instance of template 2100. Medical information received from the personal mobile communication device 200a is inputted by the data acquisition module 1104 into the appropriate data fields 2102 to 2120 of the copy or instance of the template 2100. Once complete, the copy or instance is stored in the clinician database 1010 repository as a medical record of the patient.

In some embodiments, the data acquisition module 1104 operates a routine 2150 in conjunction with or alternatively to the example patient medical template 2100. In some embodiments, the routine 2150 may be programmed as metadata or computer executable code for the respective data fields 2102 to 2120. In other examples, the routine 2150 may be stored in the clinician database 1010 in relation to the patient medical template 2100. Further, in these other examples, selection of the template 2100 causes the routine 2150 to be executed. The example routine 2150 contains routine modules 2152 to 2164 that provide associations between data fields 2102 to 2120 and corresponding medical devices, identifiers 1012, and/or consumable items 1006.

At least some of the routine modules 2152 to 2164 may be associated with or otherwise related to data templates (e.g., the data template 1700 of FIG. 17). The data acquisition module 1104 is configured to access a data template for a corresponding routine module 2152 to 2164 when a patient provides an image and/or text in a message. For example, while executing the routine module 2156 for blood pressure, the data acquisition module 1104 transmits a message that prompts the personal mobile communication device 200a for "a systolic blood pressure measurement". A patient responds with a text message containing an image of a screen or dial of the blood pressure monitor 104. The data acquisition module 1104 is configured to access a data template corresponding to or referenced to the routine module 1156 for blood pressure measurements. The data acquisition module 1104 then applies the data template to extract text from the image, using the procedure described above in connection with FIGS. 16 to 19, to identify the relevant systolic blood pressure medical information for population into the blood pressure data field 2108 of the template 2100.

The example routine 2150 may be configured to begin, upon request from a patient, based on one or more messages received by the data acquisition module 1104. For example, the data acquisition module 1104 may receive a message with text including "begin", "start", and/or "pre-treatment". Reception of the message causes the data acquisition module 1104 to determine and start the routine 2150 to populate the data fields 2102 to 2120 of the template 2100. In other examples, the data acquisition module 1104 transmits a first message specified by the routine 2150 to a patient at a predetermined time relative to a treatment. The data acquisition module 1104 sequentially sends the messages specified by the routine 2150 after receiving response message(s) from the personal mobile communication device 200a with the appropriate medical information. In this manner, the data acquisition module 1104 controls an acquisition of medical information from a patient according to a predetermined sequence. The data acquisition module 1104 may not transmit a next message in a sequence defined by the routine 2150 until an appropriate response message is received (and medical information is populated into the designated data field 2102 to 2120 of the template 2100) from the personal mobile communication device 200a.

In the illustrated example, the patient band module 2152 may include metadata or preformatted messages instructing a patient to record an image of a patient's wristband. The patient band module 2152 may also include character verification checks to ensure the received medical information conforms to text requirements for a patient's name and/or patient identifier. For example, the patient band module 2152 may reject or discard medical information for a patient's name that includes numbers.

The weight scale module 2154 may include metadata or preformatted messages instructing a patient to record an image of identifier 1012c and a screen of the scale 106 of FIG. 10. The weight scale module 2154 may also include character verification checks to ensure the received medical information is within an acceptable range of values and/or of the correct unit type. In some instances, the weight scale module 2154 may use medical information from the identifier 1012c to confirm that the medical information from the screen of the scale 106 is patient weight medical information. In other instances, medical information from the identifier 1012c is used for selecting a data template based, for example, on a model or type of the weight scale 106. The data template is used by the data acquisition module 1104 to identify relevant weight scale medical information that was extracted from images of the screen of the scale 106.

The blood pressure module 2156 is similar to weight scale module 2154 with respect to the blood pressure monitor 104. The renal failure therapy ("RFT") modules 2158 to 2162 are also similar to the weight scale module 2154. However, multiple modules 2158 to 2162 are used for the home therapy machine 90 (or a manual exchange) for each of the different windows from which medical information is needed. For example, the module 2158 provides messages for acquiring images of the identifier 1012 of the home therapy machine 90 and a first window showing a treatment status window, while the module 2160 provides one or more message for acquiring an image of a setup window of the home therapy machine 90, and the module 2162 provides one or more message for acquiring an image of a prescription window of the home therapy machine 90.

The cassette module 2164 may include metadata or preformatted messages instructing a clinician or patient to record an image of identifier 1008, a disposable cassette consumable item 1006, and/or a label on packaging or the cassette consumable itself. It should be appreciated that routine 2150 may include additional modules if the patient medical template 2100 includes additional data fields or fewer modules if the template 2100 includes fewer fields.

Once the medical information is received using the routine 2150, the data acquisition module 1104 of the application 1020 uses data verification checks to ensure the data is within an acceptable range, formatted correctly, and/or in the appropriate units. In some instances, the modules of the routine 2150 may include conversion or formatting instructions, which are used by the data acquisition module 1104 to prepare the medical information for inclusion in the respective field of the template 2100 and/or the patient's medical record. Once the data is in the appropriate format and unit, the data acquisition module 1104 writes the medical information to the respective field of the template 2100 and/or the patient's medical record.

In alternative embodiments, the patent medical template 2100 may not have an associated routine. Instead, the data acquisition module 1104 of FIG. 11 is configured to read data fields 2102 to 2120 of patient medical template 2100 to determine, for example, incomplete data fields. In these alternative embodiments, the data acquisition module 1104 identifies missing data and transmits one or more message to the personal mobile communication device 200a, prompting a patient for the missing data.

To populate the data fields, the data acquisition module 1104, in some embodiments, may read a name of the data field 2102 to 2120 (and any corresponding metadata) to create and send a message to a patient prompting the recording of certain images. In an example, the weight data field 2106 includes metadata identifying a weight scale as a related medical device. The data acquisition module 1104 determines that data field 2106 is unfilled, reads the corresponding metadata, and constructs a message instructing a patient of the personal mobile communication device 200a to record an image of a screen of a weight scale. In the illustrated embodiments, the data acquisition module 1104 may progress sequentially through template 2100 (or a patient's medical record) searching for unfilled data fields and accordingly request medical information from a patient via message(s) displayed by the personal mobile communication device 200a. Alternatively, the data acquisition module 1104 may progress through template 2100 according to a predetermined order or sequence. For example, the data acquisition module 1104 may search first for data fields associated with a patient wristband, followed by data fields for a weight scale medical device, data fields for blood pressure medical device, and data fields for a renal failure therapy medical device.

Figure 22:
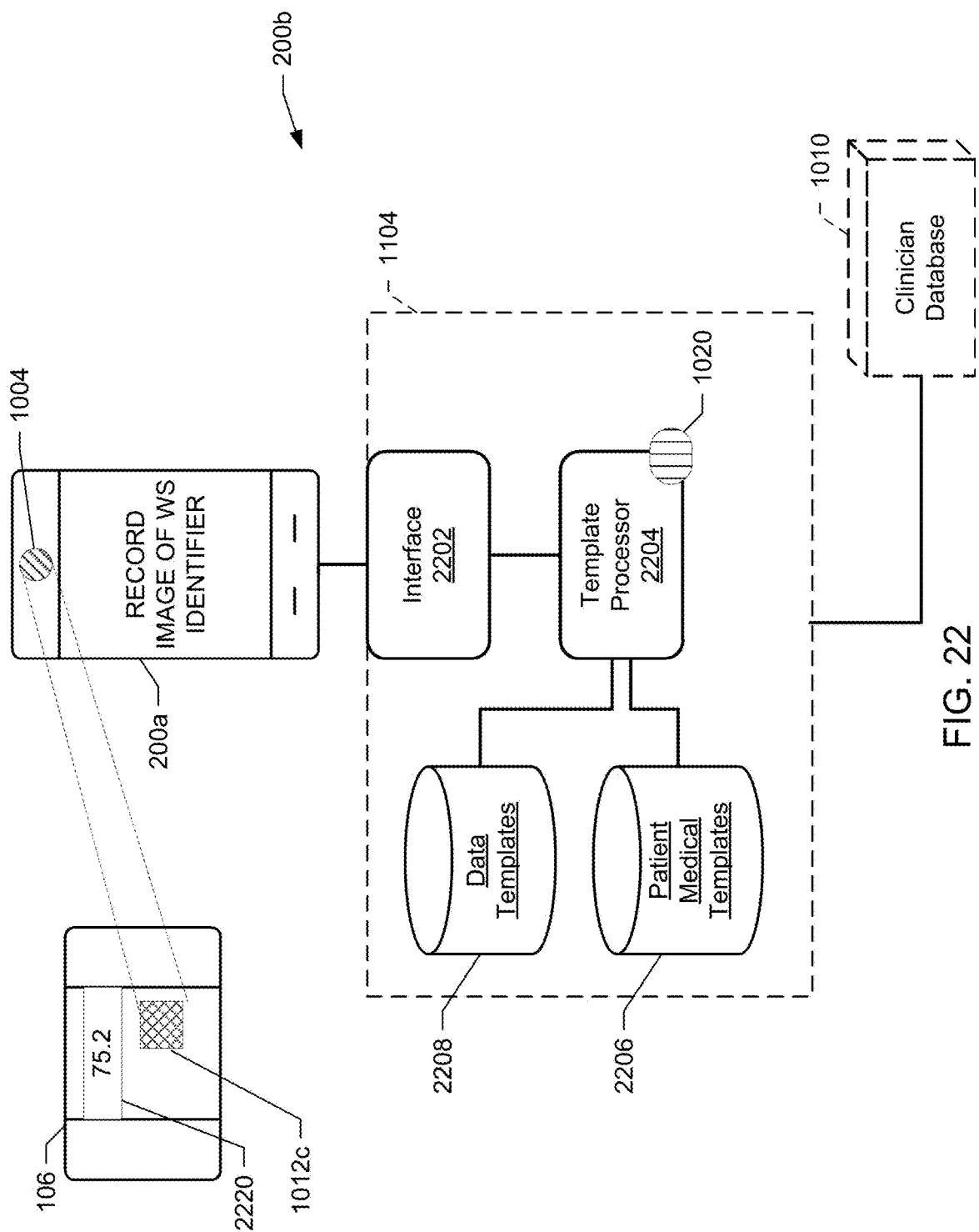
FIG. 22 is a schematic diagram of a data acquisition module of the clinician server of FIG. 11, according to an example embodiment of the present disclosure.

FIG. 22 is a schematic diagram of the data acquisition module 1104 of the clinician server 200b of FIG. 11, according to an example embodiment of the present disclosure. It should be appreciated that the illustration of the data acquisition module 1104 is exemplary and that some of the blocks may be combined, further partitioned, or removed. In addition, in some embodiments, the data acquisition module 1104 may include additional blocks, such as a block for a user interface.

The example data acquisition module 1104 (and more generally the clinician server 200*b*) includes an interface 2202 that provides connectivity with the personal mobile communication device 200*a*. The interface 2202 may include, for example, an Internet port or connection. The interface 2202 is configured, in one embodiment, to receive and convert messages from the personal mobile communication device 200*a* into a format compatible for internal processing. For example, the interface 2202 may convert SMS or text messages into an HL7 or ASCII format. The example interface 2202 is also configured to format or convert messages for transmission to the personal mobile communication device 200*a*. In some instances, the interface 2202 may encrypt messages for transmission and/or decrypt received messages.

The example data acquisition module 1104 includes a template processor 2204 configured to manage the writing or population of medical information from the personal mobile communication device 200*a* to a patient medical template 2100 or record. For example, upon request from a patient or clinician, or automatically, the template processor 2204 selects a template from a patient medical template database 2206. The selected template (e.g., the template 2100 of FIG. 21) is used by the template processor 2204 to operate a routine (e.g., the routine 2150), if available or configured, to acquire medical information from the personal mobile communication device 200*a*.

The example template processor 2204 is configured to identify messages from modules of a routine (e.g., the routine 2150) for transmission to the personal mobile communication device 200*a*. In some instances, the messages may be transmitted in a predetermined sequence to direct or guide a clinician or a patient through a process to populate a patient medical template. For example, the template processor 2204 may read module 2156 of routine 2150 of FIG. 21 and determine a message is to be transmitted that prompts a patient to record an image of the identifier 1012*c* of the scale 106. The template processor 2204 may be configured to wait until medical information related to the identifier 1012*c* is received (for populating the data field 2106 of FIG. 21) before identifying messages from routine module 2156 that are to be transmitted. In other instances, the template processor 2204 selects messages for transmission based on messages received from the personal mobile communication device 200*a*. For example, the processor 2204 may receive medical information associated with the identifier 1012*c* of the weight scale 106. In response to the received medical information, the template processor 2204 may determine that module 2154 corresponds to the received data and accordingly selects messages prompting a patient to record an image of a screen of the weight scale 104. As illustrated in FIG. 22, the personal mobile communication device 200*a* displays a text message from the template processor 2204 instructing a patient to record an image of a screen 2220 of the scale 106.

In addition to sending messages, the template processor 2204 may be configured to select data templates. The data templates are stored in a data template database 2208 in the illustrated embodiment. The template processor 2204 selects data templates based on a type or model of a medical device, which is indicated in medical information corresponding to identifier 1012. In some instances, a patient may specify the model and/or type of medical device type to the template processor 2204 via a message. Further, as discussed above, the template processor 2204 may receive image(s) from a personal mobile communication device 200*a*, extract text from the images, and select the appropriate data template from the database 2208 for identifying relevant medical information from the image(s), as described above.

In some embodiments, the template processor 2204 may receive a stream of messages from a personal mobile communication device 200*a* containing substantially all the medical information for the patient medical template 2100 or a patient's medical record. In these embodiments, the template processor 2204 reads labels, metadata, and/or device data field information provided with the data to determine a data field of the template 2100 to which the data is to be populated or written. The template processor 2204, for example, matches metadata or information of the modules (or data fields 2102 to 2120 themselves) to the labels, metadata, and/or device data field information provided with the medical information to determine the appropriate data field of template 2100.

After populating or otherwise completing a patient medical template, the template processor 2204 of FIG. 22 is configured to store the completed template to the clinician database 1010. This may include populating a patient's medical record using the template 2100, where fields in the template correspond to, are linked to, or reference fields in the patient's medical record. In other examples, the writing to a medical record may include storing a populated template to a patient's medical record or storing the template 2100 as a medical record itself.

Figure 23:
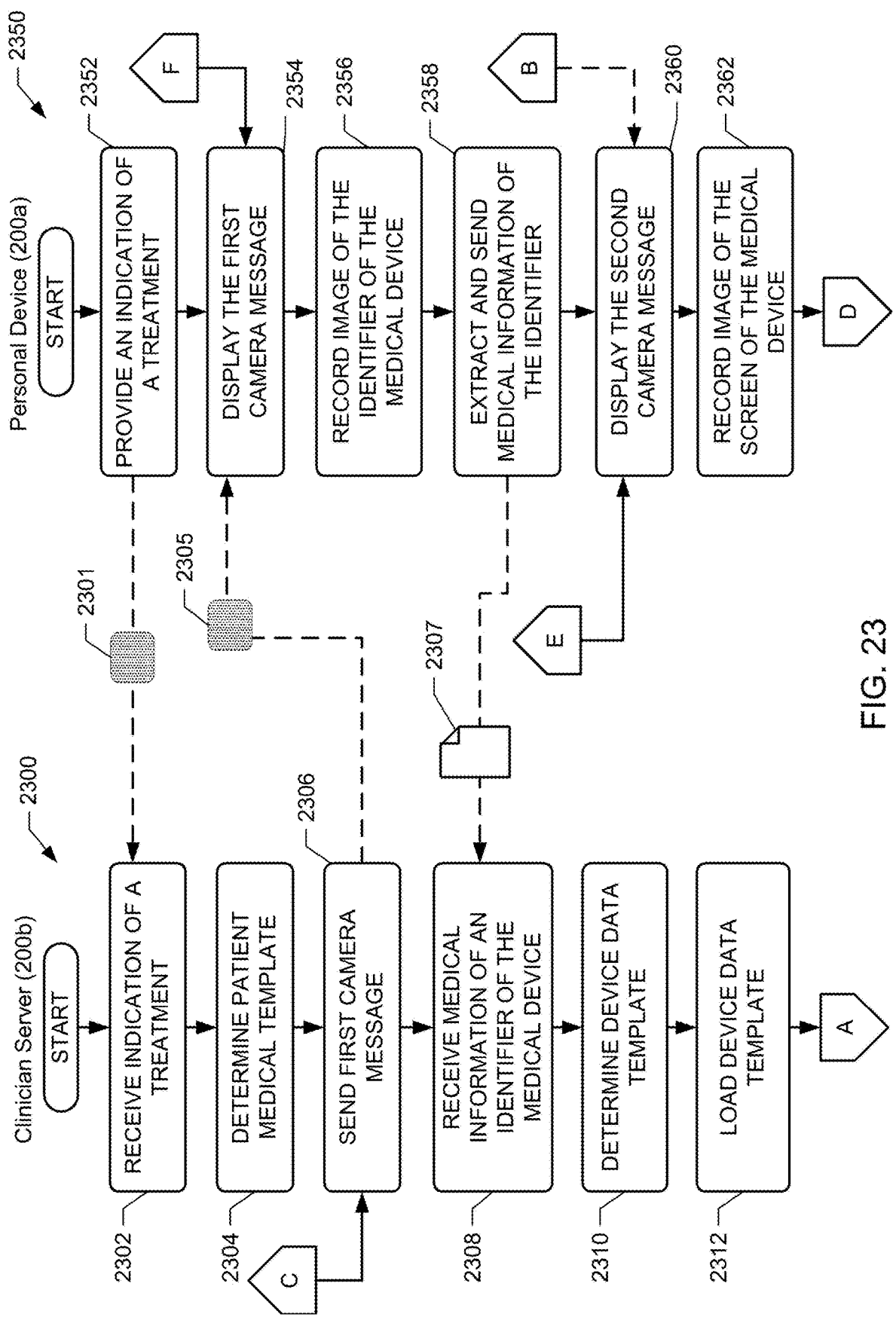
FIGS. 23 and 24 are flow diagrams of example procedures to populate the medical device template of FIG. 21 using images recorded by (and/or text messages received from) the personal mobile communication device of FIGS. 10 and 11, according to an example embodiment of the present disclosure.
Figure 24:
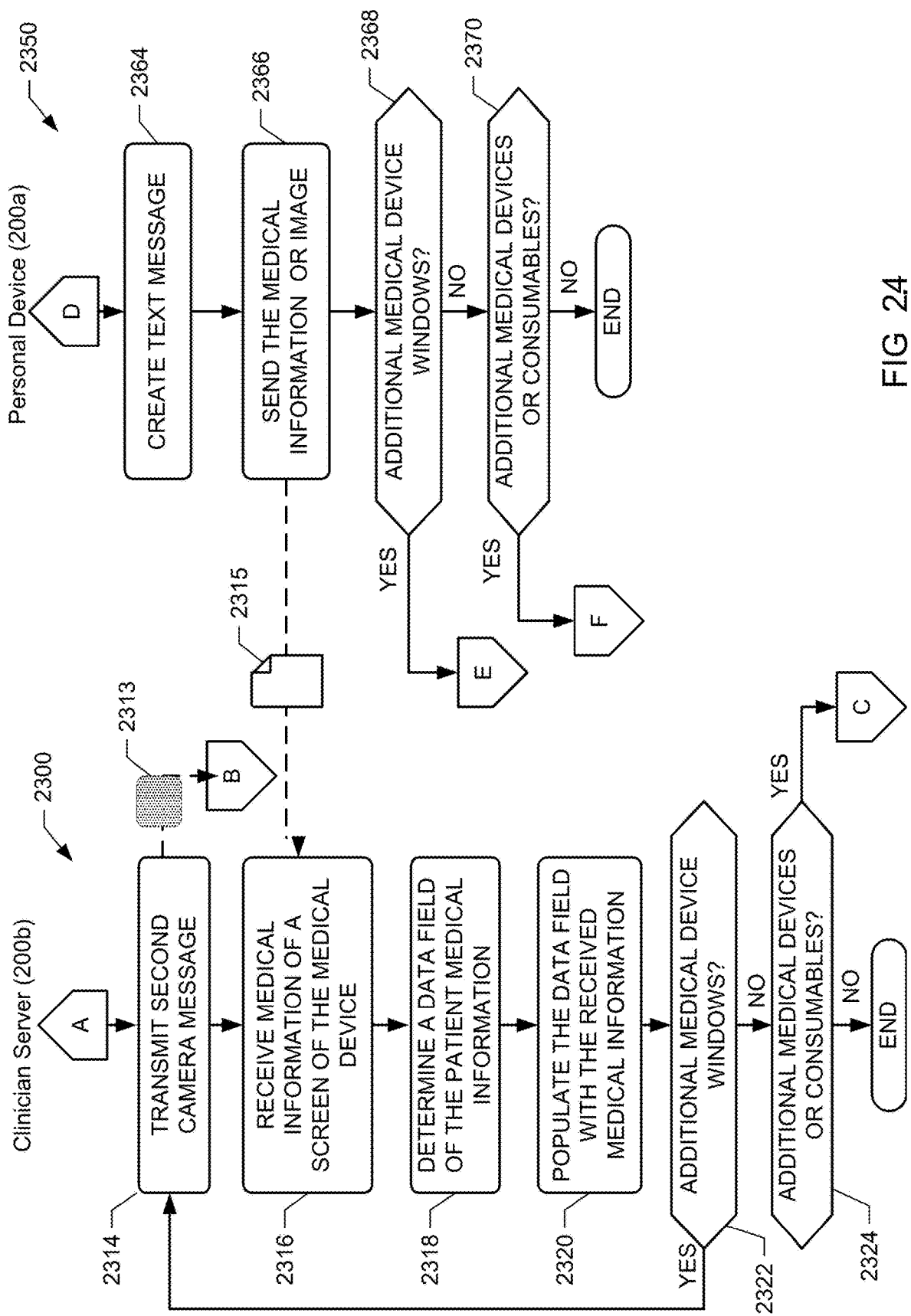

FIGS. 23 and 24 are flow diagrams of example procedures 2300 and 2350 to populate the medical device template 2100 of FIG. 21 using images recorded by (and/or text messages received from) the personal mobile communication device 200*a* of FIGS. 10 to 12 and 22, according to an example embodiment of the present disclosure. Although the procedures 2300 and 2350 are described with reference to the flow diagrams illustrated in FIGS. 23 and 24, it should be appreciated that many other methods of performing the steps associated with the procedures 2300 and 2350 may be used. For example, the order of many of the blocks may be changed, certain blocks may be combined with other blocks, and many of the blocks described may be optional. In an embodiment, the order of the blocks may be modified if a persistent connection does not exist between the clinician server 200*b* and the personal mobile communication device 200*a*. Instead, in the embodiment, the personal mobile communication device 200*a* may first acquire and queue substantially all relevant medical information for a patient medical template until a connection with the clinician server 200*b* is available (or by design). The actions described in the procedures 2300 and 2350 may be performed among multiple devices including, for example the personal mobile communication device 200*a* and the clinician server 200*b*.

The example procedure 2300 begins in FIG. 23 when the clinician server 200*b* of FIGS. 10 to 12 and 22 receives a message 2301 from the personal mobile communication device 200*a* (block 2302). The message 2301 is indicative of a treatment to be performed on a patient or a request to begin sending medical information. The clinician server 200*b* then determines a patient medical template (e.g., the patient medical template 2100 of FIG. 21) based on the treatment type specified in the message 2301 or a prescribed treatment specified in a patient's medical record (block 2304). In instances where the clinician server 200*b* only provides for the completion of one type of template (e.g., a template for a renal failure therapy), the message 2301 may indicate a request to start populating a blank template. In response to the message 2301, the clinician server 200b creates a copy of the patient medical template for population.

After providing a patient medical template for population, the clinician server 200b determines at least one medical device from which medical information is needed (using a routine associated with the template or reading the template itself) and accordingly transmits a first camera message 2305 to the personal mobile communication device 200a (block 2306). The first camera message 2305 includes instructions indicating that an image is to be recorded of, for example, an identifier 1012 of a medical device. Some time later, the clinician server 200b receives a message 2307 that includes medical information indicative of a type of medical device (e.g., medical information from an identifier 1012a) (block 2308). The clinician server 200b then determines a device data template (e.g., the device data template 1700 of FIG. 17) based on information included within the message 2307 or specified in a patient's medical record (block 2310). For example, after determining that the message 2307 identifies a blood pressure monitor 104 (type and/or model), the clinician server 200b determines or locates a device data template for the blood pressure monitor. The clinician server 200b loads the device data template for identifying relevant medical device data from an image received of a screen of the blood pressure monitor 104 (block 2312).

Example procedure 2300 continues in FIG. 24 where the clinician server 200b transmits a second camera message 2313 to the personal mobile communication device 200a (block 2314). The second camera message 2313 may be determined based on a type of medical device specified by the message 2307. Further, the second camera message 2313 may include information for displaying a certain window (or relevant medical information) on a medical device for recording an image. Some time later, the clinician server 200b receives a message 2315 that includes text from or an image of the window of the medical device (block 2316). The example clinician server 200b uses the identified data template to extract relevant medical information from an image and determines or otherwise identifies the data fields of the patient medical template that correspond to the relevant medical information (block 2318). If the message 2315 includes text, the clinician server 200b determines or otherwise identifies the data fields of the patient medical template that correspond to the relevant medical information. The clinician server 200b next populates the determined and/or identified data fields of the template with the relevant received medical information (block 2320).

After populating the relevant data fields, the example clinician server 200b determines if additional relevant medical information is needed from the medical device associated with the received relevant medical information (decision block 2322). For example, the clinician server 200b may determine that the current medical device may include additional windows or operating displays from which relevant medical information is still needed. If additional medical information is needed, the example clinician server 200b returns to block 2314 and transmits a camera message 2313 for another window for which relevant medical information is needed. However, if no additional medical information is needed for the current medical device, the clinician server 200b determines if medical information is needed from other medical devices (or consumable item 1006) (decision block 2324). If additional medical information is needed, the clinician server 200b returns to block 2306 and transmits a camera message 2305 identifying another medical device for imaging or from which to receive related medical information. If no additional medical information is needed for completion of the patient medical template 2100, the example clinician server 200b stores the completed patient medical template 2100 to the clinician database 1010 as a patient's medical record and procedure 2300 ends.

The example procedure 2350 begins on FIG. 23 by the personal mobile communication device 200a transmitting a message 2301 that is indicative of a treatment to be performed on a patient or a request to begin entering medical information (2352). The personal mobile communication device 200a next receives a camera message 2305 from the clinician server 200b. Information from the message 2305 is used by the personal mobile communication device 200a to display a prompt to a patient (block 2354). The prompt may specify, for example, that an identifier 1012 of a medical device is to be imaged. The personal mobile communication device 200a then records an image of identifier 1012 of a medical device (block 2356) based on input from the patient. In some embodiments, the patient may enter text specifying a medical device type/model or select from a drop-down menu if an identifier is not available or the patient does not want to (or cannot) record an image.

After recording an image of the identifier 1012, the personal mobile communication device 200a extracts or otherwise determines medical information encoded in the identifier (block 2358). The personal mobile communication device 200a sends the extracted medical information in a message 2307 to the clinician server 200b. In some embodiments, the personal mobile communication device 200a transmits instead the recorded image within the message 2307.

Afterwards, the personal mobile communication device 200a receives a camera message 2313 from the server 200b with information for displaying a prompt to a patient for recording an image of a screen (or other specified area) of a medical device (block 2360). The personal mobile communication device 200a accordingly displays a prompt to the patient with information needed for imaging a medical device. Responsive to the prompt, the patient uses the personal mobile communication device 200a to record an image of a screen (or other specified area) of medical device (block 2362).

In FIG. 24, the example procedure 2350 continues by the personal mobile communication device 200a creating a text message with the recorded image or text entered by the patient (block 2364). In some examples, the patient may modify or specify the medical information. The personal mobile communication device 200a then transmits a message 2315 that includes the medical information or image thereof (block 2366).

The example the personal mobile communication device 200a next determines if additional relevant medical information is needed from the medical device associated with the extracted relevant medical information (decision block 2368). The determination may include, for example, checking to see if additional camera messages related to the current medical device are received from the clinician server (block 2360). If additional medical information is needed, the example the personal mobile communication device 200a returns to block 2360 and processes a camera message 2313 for another window (or portion of the medical device/consumable item) for which relevant medical information is needed. However, if no additional medical information is needed for the current medical device, the personal mobile communication device 200a determines if medical information is needed from other medical devices (or consumable item 1006) (decision block 2370). If additional medical information is needed, the personal mobile communication device 200a returns to block 2354 and processes a camera message 2305 identifying another medical device for imaging. If no additional medical information is needed for completion of the patient medical template, the example personal mobile communication device 200a ends the session, thereby ending the procedure 2350.

6. Manual/Wireless/Image Medical Information Entry Via a Web Browser or File Transfer In some embodiments, the data acquisition module 1104 of FIG. 11 is configured to enable a patient to use their personal mobile communication device 200a to enter medical information or provide images via a web browser or file transfer program. The web browser or file transfer program enables the personal mobile communication device 200a to provide medical information and/or images without using the application 1002. In this embodiment, the clinician server 200b hosts a website, API(s), and/or a file transfer site that is assigned an address or Uniform Resource Locator ("URL"). A web browser or file transfer program on the personal mobile communication device 200a is configured to access the hosted website, API(s), and/or file transfer site to transmit medical information.

In some embodiments, the data acquisition module 1104 is configured to prompt a patient to enter a username and password to access the website or file transfer site. In other embodiments, the data acquisition module 1104 determines the personal mobile communication device 200a is previously registered and provides access. In yet other embodiments, the data acquisition module 1104 provides a mailbox or other interface (e.g., an API) to receive medical information or images without providing the personal mobile communication device 200a access to a more secure location.

Once a patient gains access via the personal mobile communication device 200a, the data acquisition module 1104, in some embodiments, provides a graphical user interface that prompts a patient for medical information and/or images. The user interface may be similar to the user interfaces 1400 and 1500 described in connection with FIGS. 14 and 15. Similar to the personal mobile communication device 200a containing the application 1002, the clinician server 200b provides the user interfaces and data fields to receive medical information. The data acquisition module 1104 may also enable a patient to select a data entry method, such as text or an image.

In some embodiments, the clinician server 200b may provide a menu to enable a patient to select the appropriate user interface. In other embodiments, the clinician server 200b may select the user interface(s) for which medical information is needed based on a prescribed treatment or treatment information provided by a patient. In yet other embodiments, the application 1020 of the clinician server 200b may operate a routine 2150 that provides graphical prompts for medical information.

Figure 25:
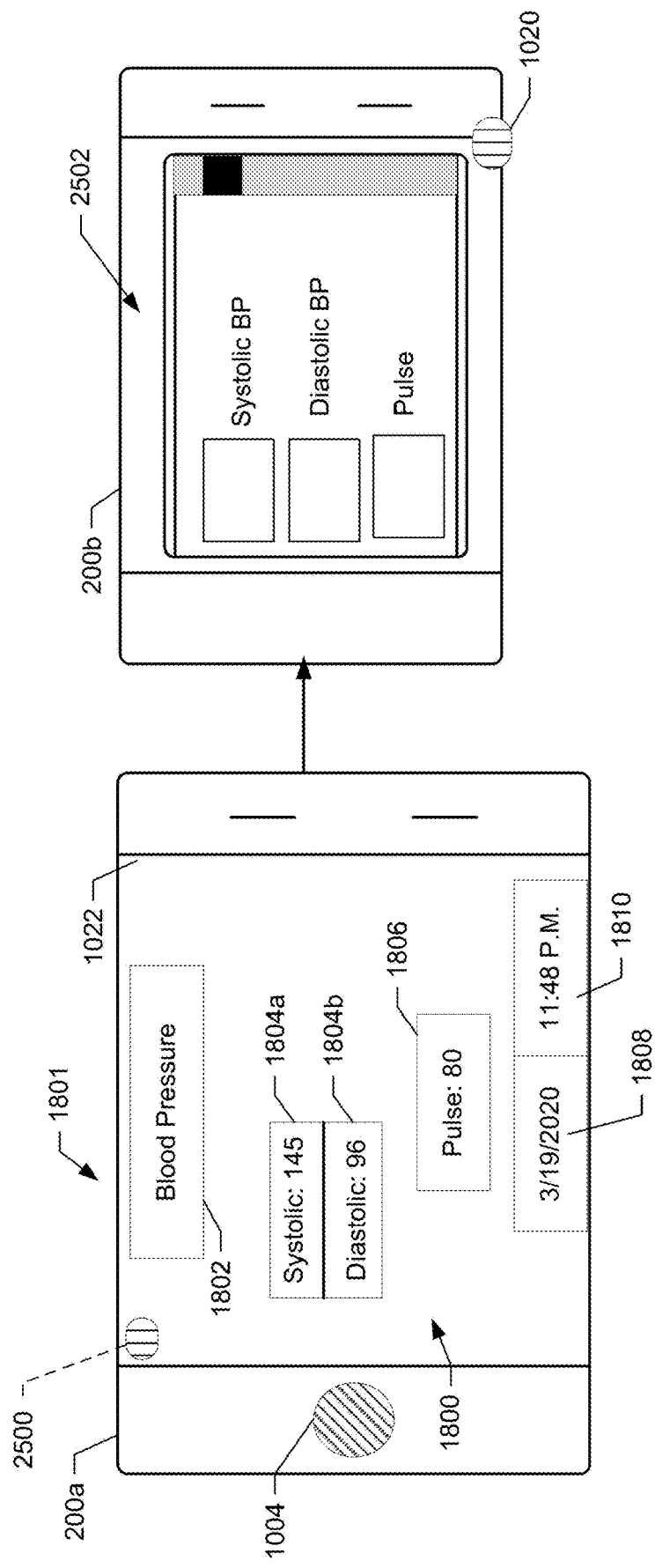
FIG. 25 shows a diagram of the clinician server hosting a website or file transfer site to receive medical information via an image from the personal mobile communication device of FIGS. 10 and 11, according to an example embodiment of the present disclosure.

FIG. 25 shows a diagram of the clinician server 200b hosting a website or file transfer site to receive medical information via an image from the personal mobile communication device 200a, according to an example embodiment of the present disclosure. In the illustrated example, the personal mobile communication device 200a is operating a web browser application 2500 that is directed to a website 2502 that is hosted by the clinician server 200b. The website 2502 includes a graphical user interface for entering medical information. In this example, the personal mobile communication device 200a records an image 1800 of a screen of the blood pressure monitor 104 of FIG. 10. The clinician server 200b applies a data template 1801 to the image to extract sets of text, as shown in fields 1802, 804, 1806, 1808, and 1810. The patient selects the field(s) 1802, 804, 1806, 1808, and 1810 for which text is to be populated into one or more selected data fields of the website 2502. In this manner, the clinician server 200b enables a patient to provide medical information via a website, file transfer program, or API(s).

C. Data Access Module Embodiment

Returning to FIG. 11, the example data access module 1106 is configured to provide patients and clinicians access to medical information stored in medical records at the clinician database 1010. As described above in connection with the data acquisition module 1104, there are different possible configurations of the personal mobile communication device 200a where the application 1002 may or may not be installed. The data access module 1106 is configured to provide access or otherwise display data based on the configurations. To determine which configuration is in use by a particular patient, the example data access module 1106 is configured to access a registration table or the patient's medical records to identify the registered personal mobile communication device 200a and/or whether the application 1002 is installed.

In some embodiments, the data access module 1106 is configured to provide the medical information differently based on an operating system of the personal mobile communication device 200a and/or a capability of the personal mobile communication device 200a. For example, a first subset of medical information may be specified for feature-rich personal mobile communication devices 200a while a second subset of medical information is provided for feature-lite personal mobile communication devices 200a. Based on registration information, the data access module 1104 determines if the application 1002 is operating on a feature-rich or feature-lite device and selects the corresponding first or second subset of medical information.

The example data access module 1106 may also determine if the medical and/or treatment information in a patient's medical record is to be converted to a different format prior to transmission. For example, medical information and/or treatment information may be stored in a medical record in an HL7 format. However, this format is not conducive for text messages and/or applications. The example data access module 1106 determines capabilities of the personal mobile communication device 200a to which the data is to be transmitted. The data access module 1106 determines capabilities based on registration information that indicates whether the application 1002 is installed and/or if the personal mobile communication device 200a is a feature-rich device. For viewing medical information on the application 1002, the data access module 1106 uses one or more APIs to convert the medical information and/or treatment information from an HL7 format to, for example, an HyperText Markup Language ("HTML") format, a JavaScript Object Notation ("JSON") format, or XML format (e.g., an application format). If the data access module 1106 determines that the application 1002 is not installed, the data access module 1106 converts the information from an HL7 format, to a text message or SMS message format via, for example, one or more APIs. The example data access module 1106 accordingly enables patient medical record information to be viewed by a patient regardless of the capabilities of their personal mobile communication devices 200a.

1. Information Display Via Application Embodiment

In some embodiments, the data access module 1106 is configured to display medical and/or treatment information via the application 1002 that is installed on the personal mobile communication device 200a. In these examples, the data access module 1106 provides medical information from one or more patient's records for display in specified fields, graphs, etc. of one or more user interfaces that are provided by the application 1002. In some instances, the fields from a medical record are referenced to fields of a user interface of the application 1002.

FIGS. 26 to 29 show diagrams of the application 1002 on the personal mobile communication device 200a displaying medical information provided by the access module 1006, according to example embodiments of the present disclosure. The application 1002 may be configured to display different user interfaces 2600, 2700, 2800, and 2900 upon selection by a patient. In some instances, the application 1002 provides a menu or other selectable graphical feature listing the different user interfaces available. The application 1002 may be configured to receive the medical information via one or more APIs linked to data fields of a patient's medical record(s). In other words, the medical information from a patient's records is plugged into blank templates that define a graphical user interface for displaying medical information.

Figures 26, 27:
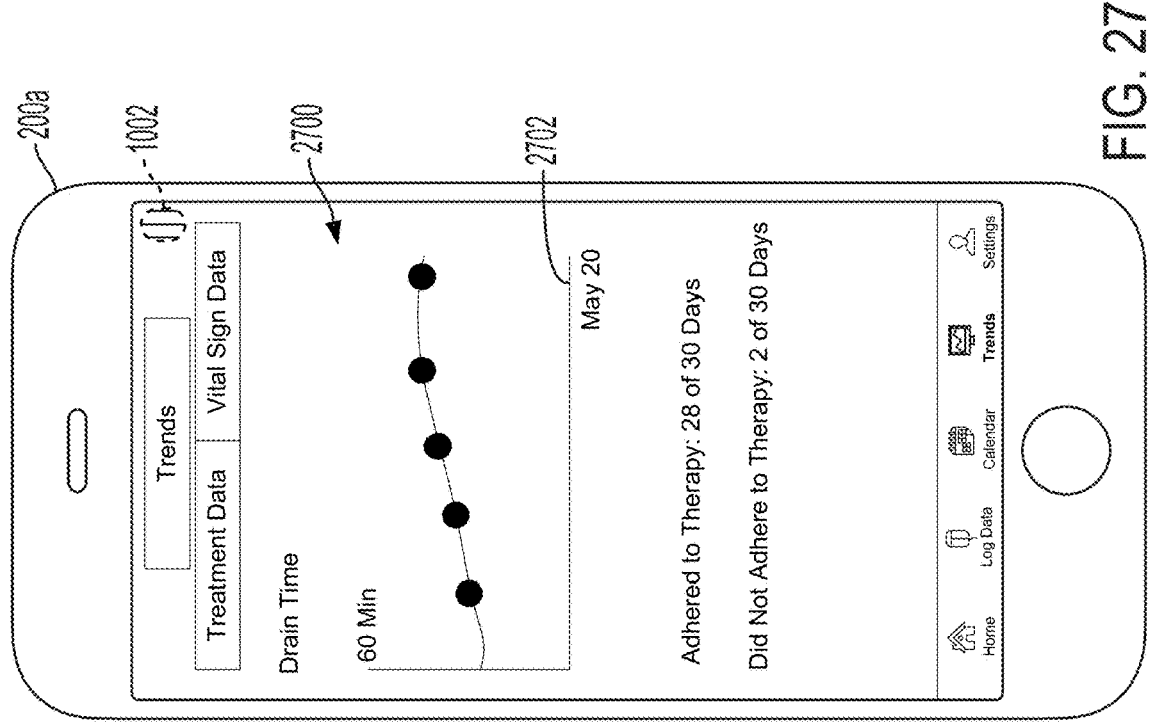
FIGS. 26 to 29 show diagrams of the personal mobile communication device displaying medical information provided by the clinician server of FIGS. 10 and 11, according to example embodiments of the present disclosure.
Figure 29:
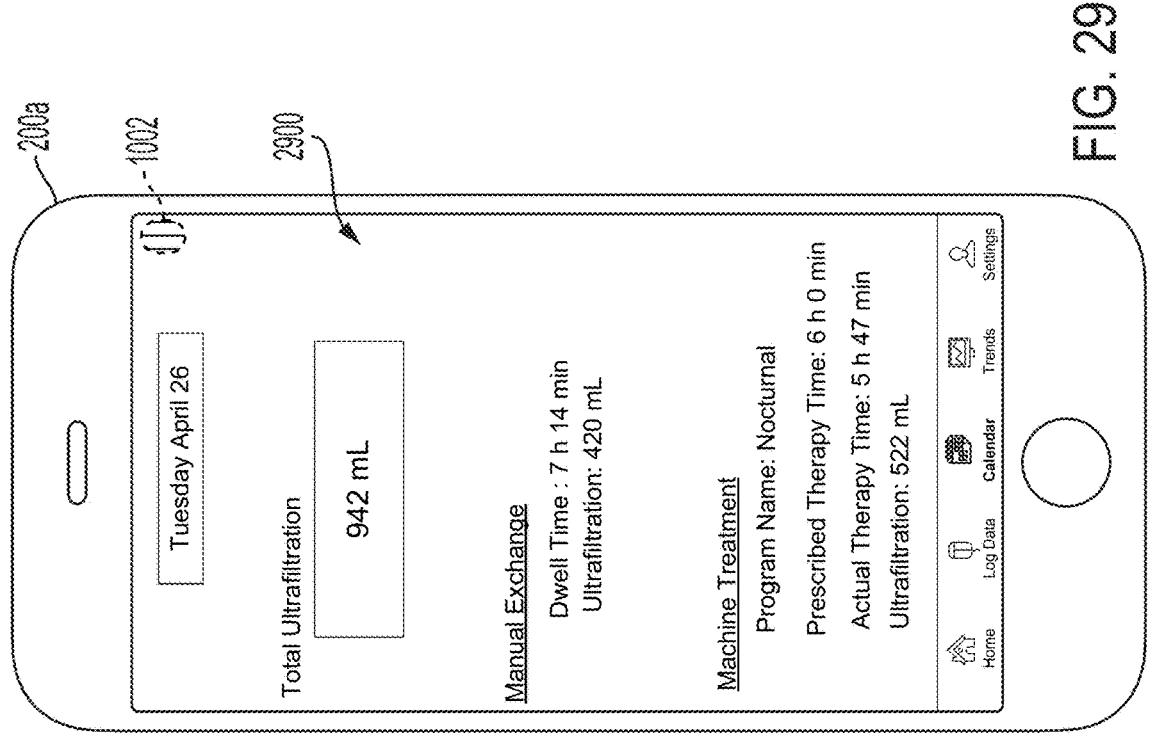
Figure 28:
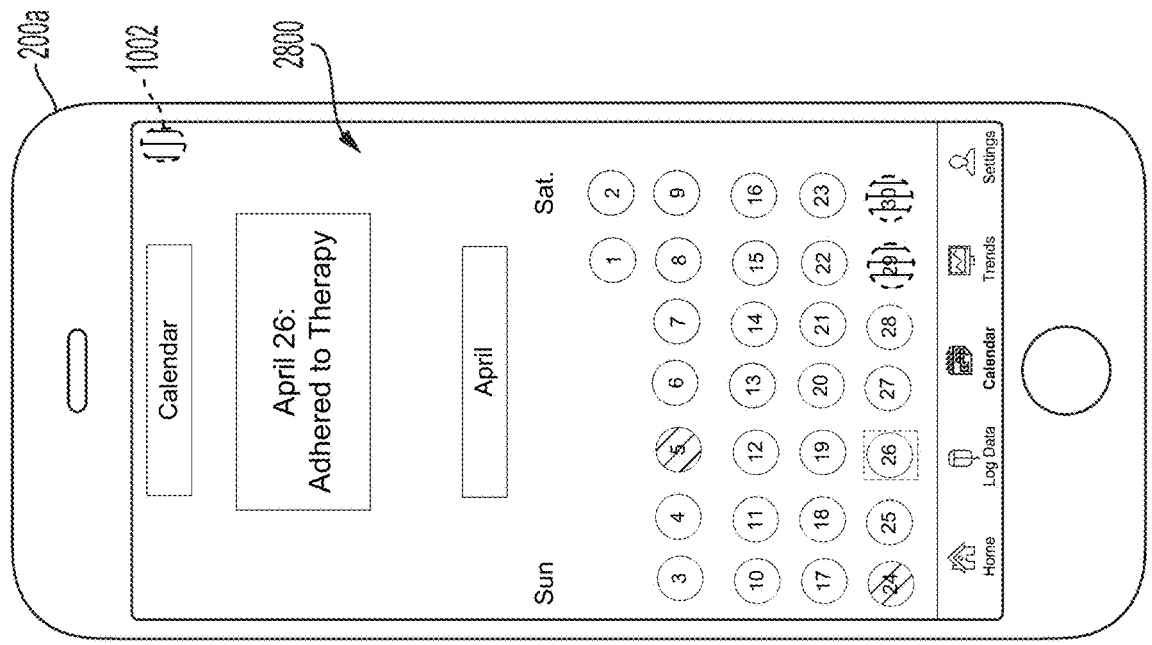

The user interface 2600 of FIG. 26 provides a first graph 2602 that illustrates a total UF removed per day and a second graph 2604 that illustrates an average UF removed per separate day/night exchanges. It should be appreciated that the medical information displayed within the graphs 2602 and 2604 may have originated from the home therapy machine 90 and/or one or more medical devices. The data access module 1106 of the clinician server 200b provides access to medical information from different sources as long as the information is already stored to a patient's medical record, thereby providing informational transparency to the patient.

The user interface 2600 is configured to enable a patient to select data points on the graphs 2602 and 2604 to provide additional treatment information. The user interface 2600 also enables a patient to select a time-range for the graphs 2602 and 2604. After receiving a selection, the application 1002 transmits a message to the data access module 1106 indicative of the selection. In return, the data access module 1106 provides the requested medical information.

The example user interface 2700 of FIG. 27 illustrates an average drain time for each UF exchange. The drain time is provided in a graph 2702. Between the user interfaces 2600 and 2700, a patient can gauge how a treatment is progressing over time. Any deviations in treatment should be readily apparent and help convince the patient to adhere to the prescribed therapy.

The example user interface 2800 includes a calendar that indicates the days in which a patient adhered to a treatment or therapy compared to days in which a patient did not adhere to a therapy. A patient may select one of the days to view additional medical information. For example, the user interface 2900 shows treatment or medical information for April 26. The information includes a total amount of UF removed during the day, in addition to a breakdown of UF removed during a manual exchange compared to UF removed via the home therapy machine 90. In the illustrated embodiment, the machine treatment information includes a program name, a prescribed therapy time, an actual therapy time, and an amount of UF removed. The data access module 1106 may determine if a treatment was adhered to based on the actual treatment time being within a threshold of the prescribed treatment time. In some embodiments, the data access module 1106 and/or the data acquisition module 1104 may determine adherence at a time when the medical or treatment information is received and set a corresponding flag or other indication in the patient's medical record to reflect adherence or lack thereof.

In some examples, the treatment information for the manual exchange is entered by the patient via the application 1002 on the personal mobile communication device 200a while the machine treatment information is separately received from the home therapy machine 90. In other examples, the user interface 2900 may display treatments that occurred at a patient's home and treatments that occurred at a clinic. The information may be organized based on which machine the information was received from, a program name, treatment type, prescription, etc. The user interface 2900 in the illustrated example accordingly provides for a single display of UF removed for different exchanges, thereby providing patient information regarding an effectiveness of a manual exchange compared to a machine-operated exchange. The example system 100 of FIG. 10 enables information from both exchanges to be stored together (based on a day of treatment) for subsequent display and/or analysis.

2. Information Display Via Web Browser Embodiment

In some embodiments, the personal mobile communication device 200a may not have the application 1002 installed. Instead, a patient may use a web browsing application to access a website or interface hosted by the clinician server 200b. In these embodiments, the data access module 1006 is configured to display the medical information and/or treatment information in one or more webpage, similar to the user interfaces 2600 to 2900 of FIGS. 26 to 29. In this embodiment, the personal mobile communication device 200a accesses the data access module 1106 via a website. Selection of a user interface or feature via the personal mobile communication device 200a causes the data access module 1106 to display the medical information within the webpage. The data access module 1106 may be configured to format or render the medical information and/or treatment information based on a web browser type and/or operating system of the personal mobile communication device 200a. In some instances, the data access module 1106 may request a username and password from a patient prior to providing access to the website.

3. Information Display Via Text Embodiment

In some embodiments, the data access module 1106 is configured to provide medical information and/or treatment information to the personal mobile communication device 200a via text messages. In these examples, the data access module 1106 may provide the information in response to a text received from the personal mobile communication device 200a. In other examples, the data access module 1106 may transmit the medical and/or treatment information periodically (e.g., daily, weekly, etc.) to a patient's personal mobile communication device 200a.

In an example, the data access module 1106 may receive a text message including text of "send 7 day UF data". In response, the data access module 1106 identifies a patient record that corresponds to the phone number of the personal mobile communication device 200a from which the text message was received. The data access module 1106 may then use a look-up table or keyword search to identify fields in a patient's medical record that includes matching sets of characters or text related to UF data (e.g., "7 day UF"). The data access module 1106 copies the matching text and creates a reply message with a value of UF for the previous seven days, which is transmitted to the personal mobile communication device 200a. Additionally or alternatively, the data access module 1106 creates and renders a seven-day graph, similar to the graph 2602 in FIG. 26. The data access module 1106 creates an image of the graph, which is transmitted to the personal mobile communication device 200a as an image in a text message. The image may be stored a .jpeg, .gif, .png, etc. file. A patient of the personal mobile communication device 200a may view the graph via the text message. In this manner, the example data access module 1106 is configured to provide patient access to medical and treatment information regardless of the capabilities and/or operating system of their personal mobile communication device 200a. In addition, the data access module 1106 determines how data is to be transmitted based on registration information provided by a patient and/or an indication of whether the application 1002 is installed on the patient's personal mobile communication device 200a.

4. Alarm/Alert Embodiments

In addition to providing a display of medical and/or treatment information, the example data access module 1106 of FIG. 11 is configured to determine and/or generate alarms and/or alerts for patients and/or clinicians. The data access module 1106 may send the alarms and/or alerts to a personal mobile communication device 200a of a patient or a clinician device 152. In some embodiments, the data access module 1106 may include a rules table that specifies to which devices certain alarms/alerts are to be transmitted. A clinician may use the clinician device 152 to subscribe to certain alarms/alerts and/or patients.

The data access module 1106 is configured to provide alarms/alerts based on how the personal mobile communication device 200a is configured to display medical and/or treatment information. For instance, if the application 1002 is installed, the data access module 1106 provides the alarms/alerts through the appropriate user interface of the application 1002. In some instances, the application 1002 is configured to display a notification indicative of the alarm/alert. If the application 1002 is not installed, the data access module 1106 determines that an alarm and/or alert is to be transmitted via an SMS or other text message to the personal mobile communication device 200a.

In some embodiments, the data access module 1106 includes or has access to a data structure or list that specifies certain conditions under which an alarm or alert is to be generated. In an example, a condition may compare a single data value or a trend (e.g., a 30-day moving average) to a range of acceptable values and/or a threshold (which may comprise hard and/or soft limits). In other examples, alarms or alerts may be generated based on multiple conditions based on comparing different types of information to respective limits. In some instances, the data access module 1106 determines derived information calculated from treatment and/or medical information, which is then compared to an acceptable range. The following provides examples of alarms/alerts that may be transmitted by the data access module 1106 via text message and/or displayed within the application 1002.

In an example, the data access module 1106 may generate an alarm or alert if it is detected that a patient is beginning to deviate from a prescribed treatment. For example, after detecting that two days have passed since treatment information has been received, the data access module 1106 (operating according to an alert rule) transmits an alert message to the personal mobile communication device 200a. The alert message specifies, for example, that the patient should perform a treatment. The alert message may also include information (or a link to information) that describes why the treatment is important or describes to the patient what happens to their body if a treatment is not performed in a timely manner. If the data access module 1106 detects, for example, four days without treatment information being received, the data access module 1106 promotes the alert to an alarm (operating according to an alarm rule). The data access module 1106 transmits the alarm to the personal mobile communication device 200a and/or the clinician device 152 to provide an indication of the severity of not adhering to a treatment. As mentioned above, the alarms and/or alerts may be transmitted by the data access module 1106 based on whether the application 1002 is installed. Even if the application 1002 is installed, the data access module 1106 is configured to transmit a text message to the personal mobile communication device 200a to flag the attention of the patient.

In some examples, a patient is prescribed a manual exchange. Accordingly, the patient has to provide treatment information indicative of the manual exchange. The data acquisition module 1106 is configured to transmit an alarm or alert if the manual exchange information is not received within a predetermined time period (e.g., within 2 days after a scheduled treatment). Further, if a manual exchange was not completed properly (e.g., a short fill or dwell time), the data access module 1106 sends an alert and/or an alarm regarding the insufficient exchange. To determine an insufficient exchange, the data access module 1106 may compare fill, dwell, and/or drain times to pre-established acceptable ranges and/or thresholds. In some instances, the data access module 1106 may request that the patient perform a full exchange.

In an example, an alarm and/or alert may be generated to indicate that a patient should select a different treatment program from a plurality of prescribed treatment programs or make an adjustment to a treatment program. In this example, an alarm or alert rule may specify that the data access module 1106 is to compare a patient's blood pressure or weight to respective change thresholds while calculating and comparing an accumulated fluid value to a threshold. The accumulated fluid value may be determined from individual fluid fill and drain volumes, which is indicative of fluid left in a patient's peritoneal cavity. If the blood pressure or weight, and accumulated fluid values (or trends) are outside of acceptable ranges, the data access module 1106 generates an alarm. The alarm may indicate that the patient has accumulated fluid and that a treatment program with a longer drain duration (or a shorter fill duration) should be selected (or a treatment program should be adjusted to provide a longer drain duration or shorter fill duration). The data access module 1106 transmits the alarm for display on the personal mobile communication device 200a. A patient may respond via the application 1002 or a text message, causing the clinician server 200*b* to make the appropriate change to the patient's prescription or therapy program.

Figure 30:
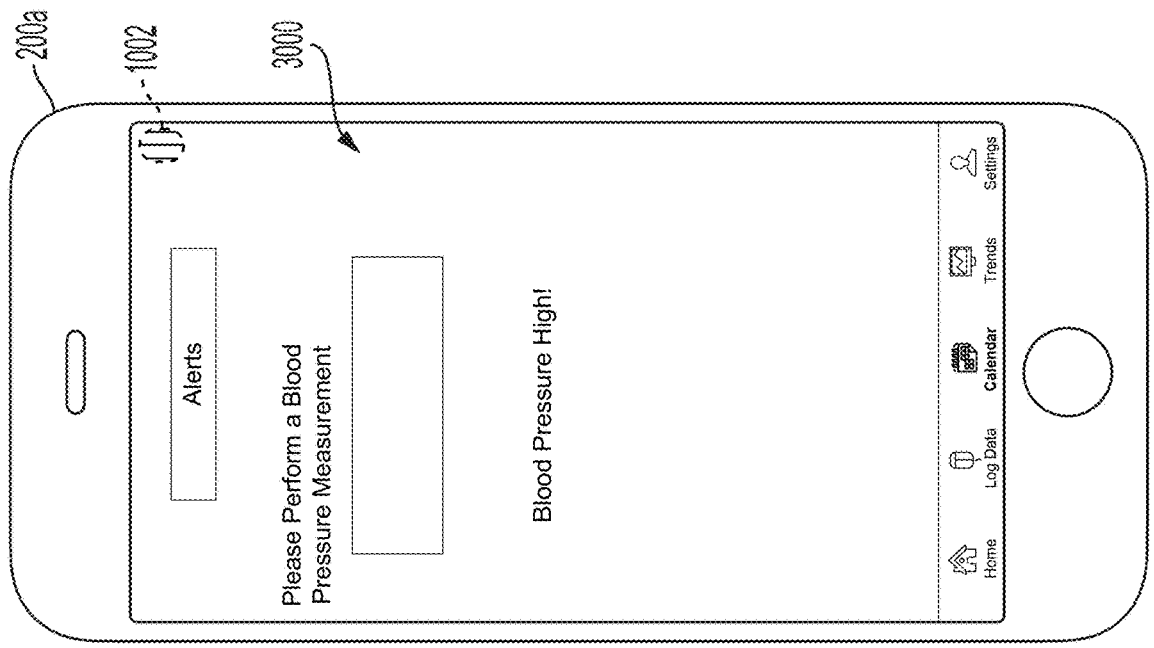
FIG. 30 shows a diagram of the personal mobile communication device of FIGS. 10 and 11 prompting a patient for medical information, according to an example embodiment of the present disclosure.

In some embodiments, alarms and/or alerts may specify conditions under which additional information is to be prompted from a patient. In these embodiments, the data access module 1106 uses treatment information from the home therapy machine 90 as a basis for determining if a patient is to provide medical information via the personal mobile communication device 200*a*. In an example, the data acquisition module 1106 may access alarm and/or alert rules that specify conditions under which a prompt or text message is sent to the personal mobile communication device 200*a* of the patient prompting for an additional weight or blood pressure measurement. For example, an alarm or alert may specify that a prompt for a new blood pressure measurement is needed if a blood pressure value (or trend) exceeds a predetermined threshold. In other examples, an alarm or alert may specify that a prompt for a new blood pressure measurement is needed if an accumulated fluid value or UF removed value (or trend) is outside of an acceptable range. In response, the data access module 1106 transmits a text message or a notification via the application 1002 for the patient to perform and record a blood pressure measurement. In some instances, the application 1002 may open a user interface (e.g., the user interface 3000 of FIG. 30) prompting the patient to enter blood pressure information. If the additional data received from the personal mobile communication device 200*a* is not within an acceptable range, the data access module 1106 may promote an alert to an alarm that is transmitted to the clinician device 152 and/or the personal mobile communication device 200*a*. Thus, the data access module 1106 is configured to operate rules that determine borderline patient conditions, which seek additional information from a patient before deciding whether further attention or action is required from a clinician or the patient.

In further embodiments, rules of the data access module 1106 may instruct a patient to inspect and/or make a change to the home therapy machine 90. In an example, a rule may specify that the data access module 1106 is to transmit an alert to a patient if treatment information has not been received from the home therapy machine 90 within a defined time period (e.g., two days). Under this situation, a patient may have provided medical information indicative that a treatment occurred, which the data access module 1106 uses to determine that an alert regarding adhering to a treatment is not necessary. Instead, the data access nodule 1106 determines that an alert is to be transmitted to the patient to check a network connection of the home therapy machine 90 so that the treatment information stored on the machine 90 can be retrieved. A patient may respond to the alert using the personal mobile communication device 200*a* to indicate that the connection was checked. After the response from the patient is received, the data acquisition module 1104 may send a ping message to the home therapy machine 90 for the missing treatment information. If a connection still cannot be made, the data access module 1106 may send an alert to the patient, a clinician, and/or a network administrator with more specific instructions for activating the home therapy machine 90 and/or overcoming the network connectivity issue.

In another example, the data access module 1106 may include one or more rules that specify an alert is to be generated responsive to treatment information being out of range. For example, a large difference between fluid fill and drain volumes may be indicative of a leak in dialysis tubing or a connection to a patient. In response, the data access module 1106 transmits an alert to the patient prompting the patient to verify fluid connections. A patient may provide a response indicating whether a leak was detected. In response, the data access module 1106 determines if the leak was corrected in a subsequent treatment cycle (or prime sequence) or if tubing should be replaced. The data access module 1106 may determine similar consumable issues for cassettes, cartridges, etc. based on treatment and/or medical information. For example, a low volume of UF removed may prompt the data access module 1106 to transmit an alert for a patient to verify a concentration of dialysis fluid and/or concentrate being connected to the home therapy machine 90.

D. Treatment Control Module Embodiment

The example treatment control module 1110 of FIG. 11 is configured to enable a patient and/or clinician to change a prescription and/or program on a home therapy machine 90. To operate, the home therapy machine 90 is assigned one or more prescriptions for a patient. A prescription may specify a treatment type (e.g., automated peritoneal dialysis treatment, manual exchange treatment, hemodialysis treatment, etc.) a time period in which a patient is to receive treatments, a dextrose level or other concentrate level of treatment fluid, a daily amount of UF to remove, and/or a number of times per day or duration range for each treatment. Each prescription may include one or more programs. A program may specify a treatment duration, a total volume of fluid to be provided to a patient, a number of fill, dwell, drain cycles to be repeated, and/or an indication whether the treatment comprises a tidal therapy. The differences in programs within a prescription enable a patient or clinician to change certain treatment parameters based on a condition or activity of a patient.

A prescription and associated programs are stored to an electronic prescription in the clinician database 1010. In some embodiments, the prescription may be stored to a patient's medical record. The home therapy machine 90 is programmed with one or more prescriptions. The programming may be performed locally via a clinician or patient, or remotely from the clinician server 200*b*. For example, the clinician server 200*b* (e.g., the treatment control module 1110) may send a copy of a prescription from the clinician database 1010 to the home therapy machine 90 after registration.

Figure 31:
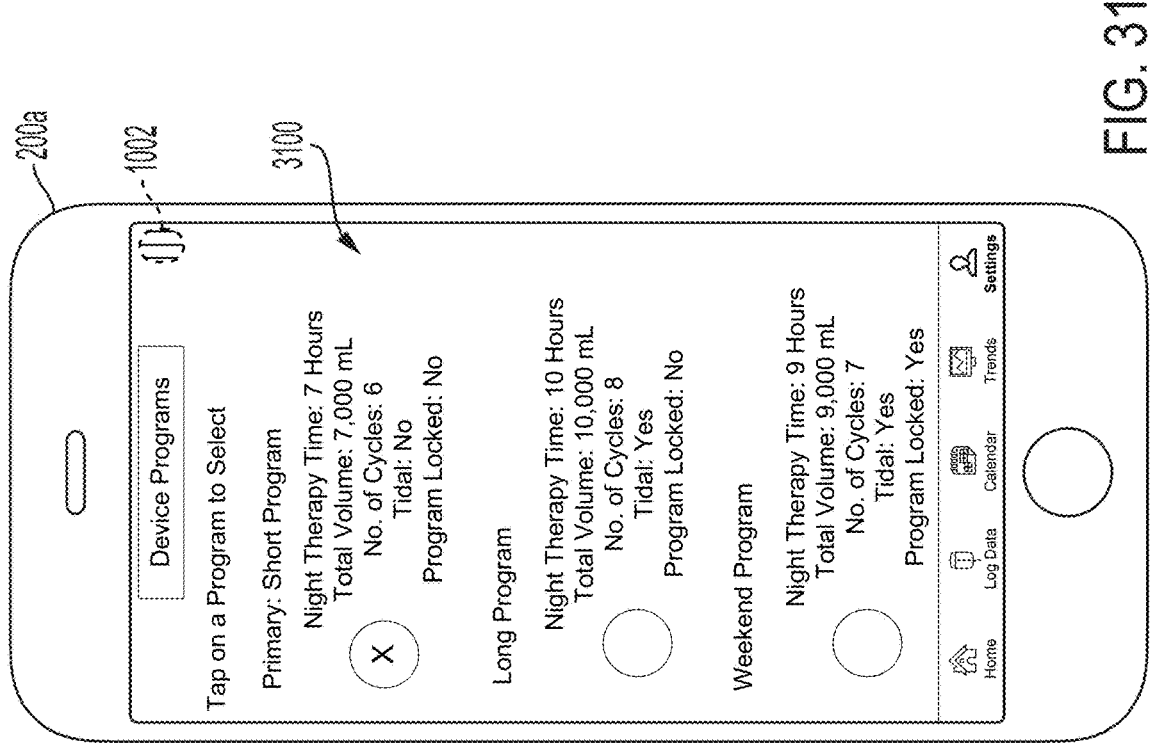
FIG. 31 shows a diagram of the personal mobile communication device of FIGS. 10 and 11 providing a patient to select a program for a medical treatment, according to an example embodiment of the present disclosure.

In some embodiments, the example treatment control module 1110 is configured to operate in connection with the application 1002 on the personal mobile communication device 200*a* and/or an application on the clinician device 152 to enable a patient and/or clinician to select a different prescription program and/or prescription. FIG. 31 shows a diagram of a user interface 3100 of the application 1002 that enables a patient to select between three different programs: a Short Program, a Long Program, and a Weekend Program. A patient may select a program based on their activity and/or circumstances. In some embodiments, the application 1002 may display an alert from the data access module 1106 that provides a recommendation to change a program based on a detected accumulation of fluid, weight gain, or higher blood pressure.

After a patient selects a different program via the user interface 3100, the application 1002 sends a message to the treatment control module 1110 indicative of the selection. In response, the treatment control module 1110 updates the patient's medical record to reflect the changed program, including a time/date of the change. Further, the treatment control module 1110 transmits a message to the home therapy machine 90 providing an instruction to change to the selected program. In some instances, the message may include treatment parameters for the newly selected program. The home therapy machine 90 accordingly performs a next treatment based on the newly selected program. In some instances, the home therapy machine 90 may display a prompt for a patient to confirm the new program before operating according to the program.

In some embodiments, the treatment control module 1110 may perform a check to verify that the patient is authorized to make a change to a program and/or whether the change is permitted. For example, the treatment control module 1110 receives an indication that a patient desires to change from the Short Program to the Long Program. The treatment control module 1110 compares to patient's medical information to one or more thresholds to ensure the change will not negatively affect the patient. For instance, the treatment control module 1110 may not approve the change from the Short to the Long Program if the patient has already accumulated a relatively large volume of fluid. If a change cannot be made, the treatment control module 1110 sends a message to the personal mobile communication device 200*a* indicative as to why the change cannot be made.

In an embodiment, the treatment control module 1110 may send a notification to the clinician device 152 indicative that the patient desires to change a program. The treatment control module 1110 may not communicate the change to the home therapy machine 90 until a confirmation is received from the clinician device 152. In some embodiments, a clinician may change a program and/or prescription via the treatment control module 1110 using their clinician device 152. In these embodiments, the treatment control module 1110 may send a message for display in the application 1002 of the personal mobile communication device 200*a* indicative of the change in program and/or indicative that a clinician made the change.

In instances where the personal mobile communication device 200*a* does not include the application 1002, the treatment control module 1110 is configured to permit changes to a prescription. For example, the treatment control module 1110 may host a website accessible by a web browser on the personal mobile communication device 200*a*. The web site may include features similar to the user interface 3100 of FIG. 31 to enable a patient to remotely select a different program and/or prescription.

Additionally or alternatively, the treatment control module 1110 is configured to enable treatment changes via text messages. In an example, a patient may send a message from the personal mobile communication device 200*a* including text of "change treatment". In response, the treatment control module 1110 is configured to send a reply message with different treatment program options and a corresponding code or designator next to each option. A patient may enter the designator or code in a response message to select a desired program. In another example, a patient may send a message with text consisting of, for example, "Long Program" to cause the treatment control module 1110 to change programs to the Long Program.

E. Education Module Embodiment

The example education module 1108 of FIG. 11 is configured to provide educational material and/or encouragement to a patient via the personal mobile communication device 200*a*. Similar to the other modules 1102 to 1106 and 1110 of FIG. 11, the education module 1108 is configured to provide content/information based on a configuration of the personal mobile communication device 200*a*. For example, if the application 1002 is installed, the education module 1108 is configured to select and provide educational material through the application 1002. If the application is not installed, the education module 1108 is configured to provide educational material via a website and/or text messages. In instances of text messages, the education module 1108 may be configured to structure educational material to fit within a text message or provide a link to educational material at the clinician database 1010 or hosted by a third-party server.

As described herein, educational material may include text-based articles, audio, video, multimedia presentations, etc. The educational material may provide general information about a patient's condition, information about the application 1002, and/or information regarding the home therapy machine 90. The educational material may also be targeted based on detected patient conditions (determined from their medical record) and/or feedback regarding a patient's use of the application 1002 and/or the home therapy machine 90.

Also, as described herein, encouragement includes text, audio, video, or multimedia presentations designed to improve a patient's mood or help a patient adhere to a program. Encouragement may also include rewards or badges. In some embodiments, the education module 1108 may be configured to provide encouragement based on detected conditions. In some instances, the encouragement may be provided in combination with an alert generated by the data access module 1106. In an example of encouragement, a different status level may be provided to a patient based on a rate of adherence (e.g., "Dialysis SuperStar" for near-perfect adherence).

The educational material and/or encouragement may be stored in the clinician database 1010. In addition, the education module 1108 may have access to third-party material, such as from the National Institute of Health or the Cleveland Clinic®. The education module 1108 may include a rules data structure that specifies conditions under which certain educational material and/or encouragement is to be provided to the personal mobile communication device 200*a*.

Figure 32:
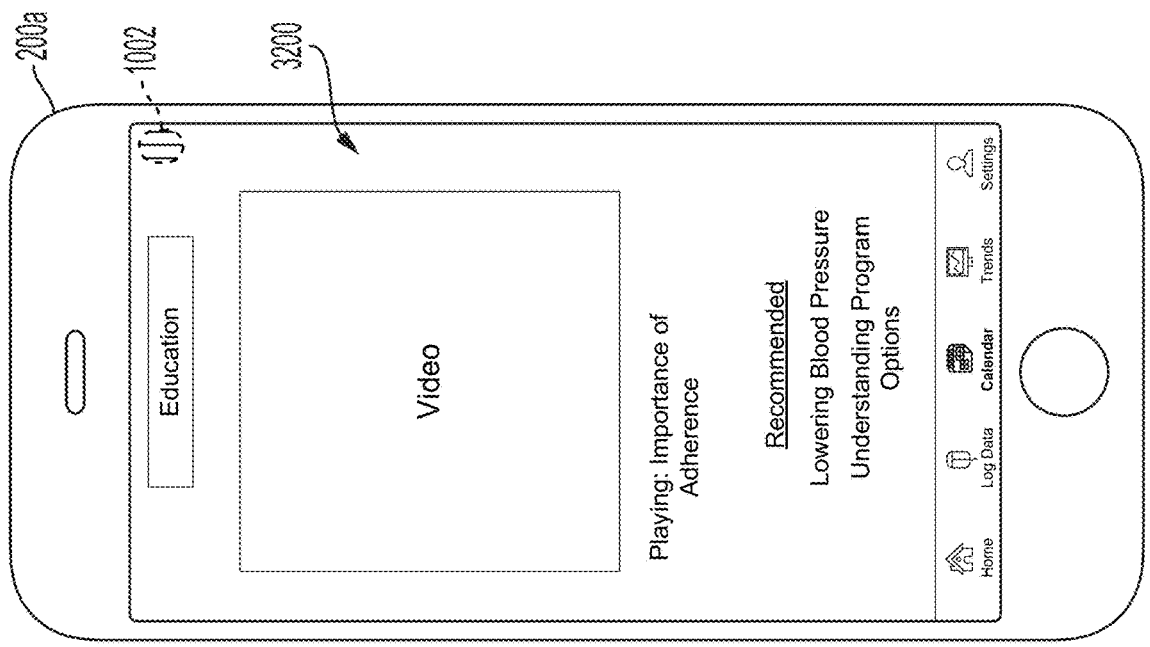
FIG. 32 shows a diagram of the personal mobile communication device of FIGS. 10 and 11 providing educational content a patient, according to an example embodiment of the present disclosure.

In an example, the data access module 1106 determines a patient is not adhering to a treatment. In addition to the data access module 1106 sending an alert, the education module 1108 may recommend or provide a link to a video regarding the importance of adherence. FIG. 32 shows an example user interface 3200 of the application 1002 displaying an educational video related to adherence provided by the education module 1108. The example user interface 3200 also provides a list of recommended educational material based on detected conditions of the patient. For example, after detecting the patient has high blood pressure from a medical record or received as medical information, the education module 1108 is configured to recommend educational content about lowing blood pressure. Further, after detecting that a patient has not changed programs of a prescription, the education module 1108 determines that educational content explaining the program options should be recommended.

The example education module 1108 may also detect how a patient interacts with the application 1002 and recommend educational content. For example, the education module 1108 receives feedback from the application 1002 indicative that a patient has made multiple attempts in populating a data field of a user interface (e.g., the user interface 14 of FIG. 14) using a recorded image. In response, the education module 1108 may provide a notification via the application 1002 recommending that the patient view a tutorial regarding information entry using a recorded image.

The example education module 1108 may store to a patient's medical record an indication of any educational content or encouragement displayed by the personal mobile communication device 200a. Such information may be useful to a clinician to determine how engaged a patient is with a treatment. The stored information may also provide an indication of a patient's awareness of a treatment.

F. Assistance Module Embodiment

The example assistance module 1112 of FIG. 12 is configured to create a communication session between a patient and a clinician. Specifically, the assistance module 1112 is configured to create a communication session between a clinician device 152 and the personal mobile communication device 200a. The assistance module 1112 may use a capability of the personal mobile communication device 200a to determine an appropriate communication session.

A communication session may include a video session, an audio call, a conference call, an SMS session, or a web-messaging session. If the application 1002 is installed, the assistance module 1112 may access an option for selecting a video session, a conference session, or a web-messaging session for connecting a patient to a clinician through the application 1002. If the application 1002 is not installed, the assistance module 1112 may be limited to options related to the native communication capabilities of the personal mobile communication device 200a, such as text messaging and audio calls.

Figure 33:
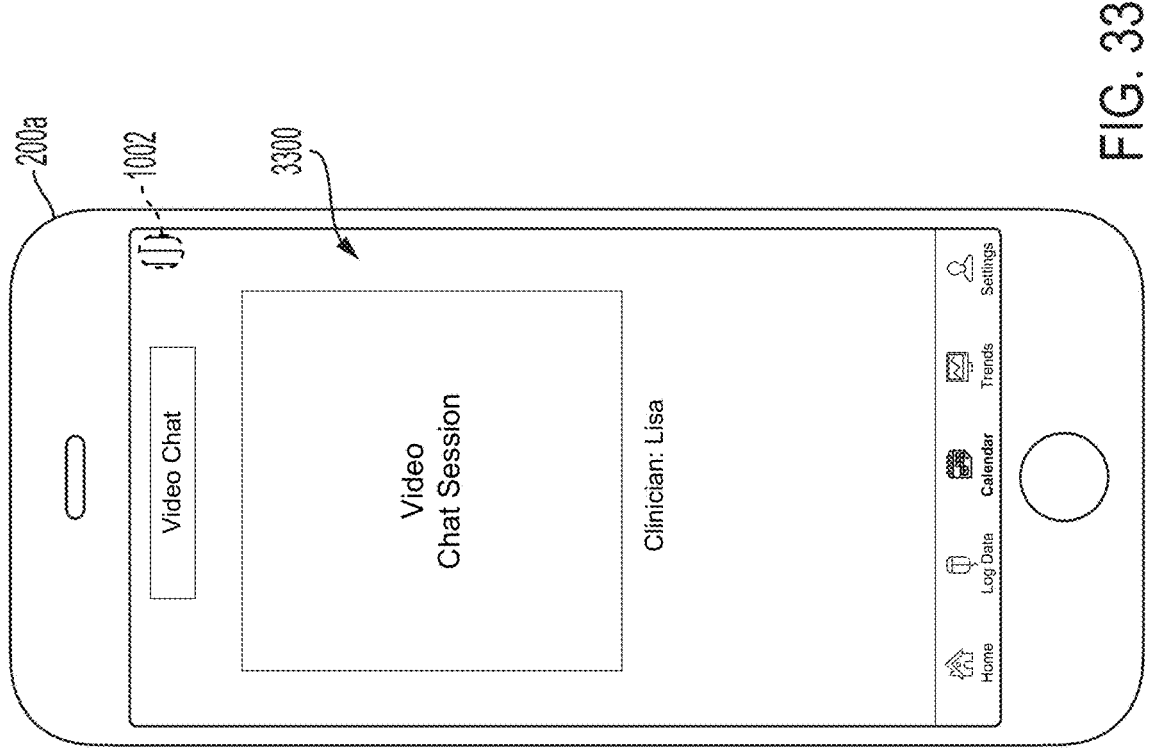
FIG. 33 shows a diagram of the personal mobile communication device of FIGS. 10 and 11 providing a video chat session between a patient and a clinician, according to an example embodiment of the present disclosure.

In some embodiments, a patient may initiate a session. The application 1002 is configured to enable a patient to request to contact a clinician, including specifying a preferred communication method. Using a text feature of the application 1002, a patient may send a text message including text of "help" to the assistance module 1112 to begin a session. After a patient requests to begin a session, the assistance module 1112 is configured to identify an available clinician. In some embodiments, the assistance module 1112 may locate a record of clinicians associated with the patient and send a ping/request message to their devices. A received response from one of the devices 152 provides an indication that the clinician is available and willing to communicate with the patient. In some instances, the response may indicate the clinician's method of communication. In response to a received message, the assistance module 1112 begins a communication session. This may include establishing a web call, a messaging session, or audio call between a personal mobile communication device 200a and a clinician device 152. In some embodiments, instead of broadcasting a ping message to a group of clinicians, the assistance module 1112 may sequentially send ping/request messages to clinicians according to a predetermined order (e.g., primacy clinician: first, on-call clinicians of the same office: second, on-call clinicians of a different office: third, etc.). FIG. 33 shows a diagram of a user interface 3300 of the application 1002 providing a video session within a clinician. The video session enables a patient to address their concerns regarding their treatment. The video session also enables a clinician to view a real-time setup of the treatment or assist a patient setting up a treatment.

In some embodiments, the assistance module 1112 may determine that a communication session is to be opened or recommends opening a communication session. The assistance module 1112 may provide a recommendation in conjunction with the data access module 1106 generating an alarm and/or alert. The assistance module 1112 may, after detecting conditions for an alert and/or alarm, identify a clinician device 152 that is available to participate in a session and then initiate a call to the personal mobile communication device 200a to address an alert and/or alarm. In an example, the assistance module 1112 may attempt to create a communication session after detecting a patient's blood pressure, weight, accumulated fluid, etc. is above a predetermined threshold or has changed significantly within a predetermined period of time.

The example assistance module 1112 may determine a type of assistance being sought to identify the correct individual for connection. In addition to a clinician, the assistance module 1112 may be able to connect to information technology specialists and home therapy machine specialists. Before initiating a session, the application 1002 may prompt a patient to identify an assistance type (e.g., application help, machine help, clinical help, etc.). In other instances, the assistance module 1112 may determine an assistance type based on a context in which a request for a session was received. For example, after reviewing an educational training program about the home therapy machine 90, the assistance module 1112 determines that a subsequent request for assistance is in regards to operating the home therapy machine 90. In another example, while the application 1002 is displaying a user interface regarding UF trending, the assistance module 1112 determines that a subsequent request for assistance is in regards to a clinical matter.

The example assistance module 1112 may be configured to record a log of a communication session to a patient's medical record. The assistance module 1112 may record a date/time of a communication session and an indication of how the session was initiated. The record may also include participants of the communication session as well as a transcript of the communications. For text messages, this may include a copy of the messages. For audio or video, this may include a recording of the call or a transcription of the call.

III. CONCLUSION

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A system for transmitting information to a patient, the system comprising:
    a home therapy machine of the patient configured to transmit treatment information;
    a clinician database configured to store a medical record and a registration file identifying (i) the home therapy machine and a personal device of the patient as registered devices, and (ii) whether the personal device installed an application for viewing the treatment information; and
    a clinician server communicatively coupled to the clinician database, the home therapy machine, and the personal device, the clinician server configured to store the treatment information to the medical record,
receive an indication that at least some of the treatment information is to be displayed at the personal device,
determine from the registration file if the application is installed on the personal device,
if the application is installed
convert the at least some of the treatment information to an application format for display within the application, and
transmit the converted at least some of the treatment information to the personal device, and
if the application is not installed
convert the at least some of the treatment information to a text message format or a Short Messaging Service ("SMS") format, and
transmit the converted at least some of the treatment information to the personal device via one or more text message or SMS message.

2. The system of claim 1, wherein the application format includes at least one of an Extensible Markup Language ("XML") format or a HyperText Markup Language ("HTML") format.

3. The system of claim 1, wherein the indication that at least some of the treatment information is to be displayed at the personal device includes at least one of a message from the application or a text/SMS message from the personal device.

4. The system of claim 1, wherein the registration file is included within the medical record.

5. The system of claim 1, wherein the home therapy machine is configured to store a prescription with two programs, each of the programs providing parameters to operate the home therapy machine to perform a treatment, and wherein the clinician server is configured to:
receive a program message from the personal device indicative of a change to a second program from a first program; and
transmit a program instruction to the home therapy machine to change to the second program from the first program.

6. The system of claim 1, wherein the home therapy machine includes at least one of a renal failure therapy machine, an infusion pump, an oxygen sensor, a respiratory monitor, a glucose meter, a blood pressure monitor, an ECG monitor, a weight scale, and a heart rate monitor.

7. The system of claim 1, wherein the treatment information includes at least one of blood pressure measurement data, pulse data, weight data, glucose data, temperature data, renal failure manual exchange data, subjective data, or consumable data regarding a consumable item.

8. The system of claim 7, wherein the consumable item includes at least one of a filter, a blood line set, a dialysate concentrate container, a blood anticoagulant container, a medication container, a disposable cassette, a sorbent cartridge, and a water purification container.

9. The system of claim 1, wherein the personal device is a personal mobile communication apparatus.

10. A method for transmitting information to a patient, the method comprising:
storing, in a clinician database, a registration file identifying (i) a home therapy machine and a personal device of the patient as registered devices, and (ii) whether the personal device installed an application for viewing the treatment information;
receiving, in the clinician database from the home therapy machine of the patient, treatment information;
storing, in the clinician database via a server, the treatment information to a medical record of the patient;
receiving, in the server, an indication that at least some of the treatment information is to be displayed at the personal device;
determining, via the server, from the registration file if the application is installed on the personal device;
if the application is installed
converting, via the server, the at least some of the treatment information to an application format for display within the application, and
transmitting, via the server, the converted at least some of the treatment information to the personal device; and
if the application is not installed
converting, via the server, the at least some of the treatment information to a text message format or a Short Messaging Service ("SMS") format, and
transmitting, via the server, the converted at least some of the treatment information to the personal device via one or more text message or SMS message.

11. The method of claim 10, wherein the application format includes at least one of an Extensible Markup Language ("XML") format or a HyperText Markup Language ("HTML") format.

12. The method of claim 10, wherein the indication that at least some of the treatment information is to be displayed at the personal device includes at least one of a message from the application or a text/SMS message from the personal device.

13. The method of claim 10, further comprising converting, via the server, the treatment information to a Health-Level-7 ("HL7") format before storing to the medical record.

14. The method of claim 10, wherein the home therapy machine is configured to store a prescription with two programs, each of the programs providing parameters to operate the home therapy machine to perform a treatment, the method further comprising:
receiving, in the server, a program message from the personal device indicative of a change to a second program from a first program; and
transmitting, via the server, a program instruction to the home therapy machine to change to the second program from the first program.

15. The method of claim 10, wherein the treatment information includes at least one of blood pressure measurement data, pulse data, weight data, glucose data, temperature data, renal failure manual exchange data, subjective data, or consumable data regarding a consumable item.

16. A system for transmitting information to a patient, the system comprising:
a clinician database configured to store a medical record and a registration file identifying (i) a home therapy machine and a personal device of the patient as registered devices, and (ii) whether the personal device installed an application for viewing treatment information from the home therapy machine; and
a clinician server communicatively coupled to the clinician database, the home therapy machine, and the personal device, the clinician server configured to
convert treatment information received from the home therapy machine to a Health-Level-7 ("HL7") format, store the converted treatment information to the medical record, receive an indication that at least some of the converted treatment information is to be displayed at the personal device, determine from the registration file if the application is installed on the personal device, if the application is installed convert the at least some of the converted treatment information to an application format for display within the application, and transmit the converted at least some of the treatment information to the personal device, and if the application is not installed convert the at least some of the converted treatment information to a text message format or a Short Messaging Service ("SMS") format, and transmit the converted at least some of the treatment information to the personal device via one or more text message or SMS message.

17. The system of claim 16, wherein the application format includes at least one of an Extensible Markup Language ("XML") format or a HyperText Markup Language ("HTML") format.

18. The system of claim 16, wherein the indication that at least some of the treatment information is to be displayed at the personal device includes at least one of a message from the application or a text/SMS message from the personal device.

19. The system of claim 16, wherein the personal device is a personal mobile communication apparatus, and wherein the home therapy machine includes at least one of a renal failure therapy machine, an infusion pump, an oxygen sensor, a respiratory monitor, a glucose meter, a blood pressure monitor, an ECG monitor, a weight scale, and a heart rate monitor.

20. The system of claim 16, wherein the treatment information includes at least one of blood pressure measurement data, pulse data, weight data, glucose data, temperature data, renal failure manual exchange data, subjective data, or consumable data regarding a consumable item.

* * * * *